(12) United States Patent
Riley et al.

(10) Patent No.: US 6,507,391 B2
(45) Date of Patent: Jan. 14, 2003

(54) MEASURING THE VELOCITY OF SMALL MOVING OBJECTS SUCH AS CELLS

(75) Inventors: James K. Riley, Redmond, WA (US); David A. Basiji, Seattle, WA (US); Richard A. Bauer, Kirkland, WA (US); Keith L. Frost, Seattle, WA (US); William E. Ortyn, Bainbridge Island, WA (US); David J. Perry, Woodinville, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 09/939,049

(22) Filed: Aug. 24, 2001

(65) Prior Publication Data

US 2002/0122167 A1 Sep. 5, 2002

Related U.S. Application Data

(60) Provisional application No. 60/228,076, filed on Aug. 25, 2000.

(51) Int. Cl.[7] .................................................. G01P 3/36
(52) U.S. Cl. ........................ 356/28; 356/28.5; 356/39
(58) Field of Search ............................ 356/28, 28.5, 39

(56) References Cited

U.S. PATENT DOCUMENTS

| | | | |
|---|---|---|---|
| 2,772,479 A | * 12/1956 | Doyle | |
| 3,432,237 A | 3/1969 | Flower et al. ................. 356/28 |
| 3,489,495 A | * 1/1970 | Blau et al. ...................... 356/28 |
| 3,525,569 A | * 8/1970 | Gamertsfelder et al. | |
| 3,677,647 A | * 7/1972 | Misek ........................... 356/28 |
| 3,706,494 A | * 12/1972 | Gardner ........................ 356/28 |
| 3,711,200 A | * 1/1973 | Maughmer .................... 356/28 |
| 3,832,059 A | 8/1974 | Iten ............................... 356/28 |
| 3,856,403 A | 12/1974 | Maughmer et al. ............ 356/28 |
| 3,953,126 A | 4/1976 | Kim et al. ..................... 356/28 |
| 4,148,585 A | 4/1979 | Bargeron et al. .......... 356/28.5 |
| 4,729,109 A | 3/1988 | Adrian et al. ............... 364/560 |
| 4,786,165 A | 11/1988 | Yamamoto et al. ........... 356/23 |
| 5,014,131 A | * 5/1991 | Reed et al. .................... 356/28 |
| 5,054,913 A | * 10/1991 | Ishikawa et al. ........... 356/28.5 |
| 5,159,397 A | 10/1992 | Kosaka et al. ................ 356/73 |
| 5,159,398 A | 10/1992 | Maekawa et al. ............. 356/73 |

(List continued on next page.)

FOREIGN PATENT DOCUMENTS

WO    WO 00/42412    7/2000

OTHER PUBLICATIONS

Ong, S.–H.; Horne, D.; Yeung, C.–K.; Nickolls, P.; Cole, T. "Development of an Image Flow Cytometer." Analytical and Quantitative Cytology and Histology. XIVth International Conference on Medical and Biological Engineering and the VIIth International Conference on Medical Physics, Espoo, Finland. Aug. 11–15, 1985, Pp. 375–382.

Ong, Sim Heng. "Development of a System for Imaging and Classifying Biological Cells in a Flow Cytomer." Doctor of Philosophy Thesis. University of Sydney, School of Electrical Engineering. Aug. 1985.

Primary Examiner—Stephen C. Buczinski
(74) Attorney, Agent, or Firm—Ronald M. Anderson

(57) ABSTRACT

Frequency domain velocity measurements and time domain velocity measurements are made using light from cells or other objects. An optical grating is used to modulate the light from an object so that it has a frequency proportional to the velocity of the object. Depending upon the embodiment, the pitch of the optical grating is uniform or varying. The modulated light is detected, producing an analog signal that is then digitally sampled. Time domain signal processing techniques are used to determine the velocity of the object from the digital samples. Preferably, the velocity measured is applied in determining a timing signal employed for synchronization of an image of the object and an detector signal in an optical analysis system that uses a time delay integration (TDI) detector to determine characteristics of the object in response to light from the object.

88 Claims, 48 Drawing Sheets

U.S. PATENT DOCUMENTS

| | | | |
|---|---|---|---|
| 5,159,642 A | 10/1992 | Kosaka | 382/6 |
| 5,160,976 A | 11/1992 | Carr et al. | 356/349 |
| 5,229,830 A | 7/1993 | Ishida et al. | 356/28.5 |
| 5,247,339 A | 9/1993 | Ogino | 356/73 |
| 5,272,354 A | 12/1993 | Kosaka | 250/574 |
| 5,333,044 A | 7/1994 | Shaffer | 356/28 |
| 5,422,712 A * | 6/1995 | Ogino | 356/73 |
| 5,444,527 A | 8/1995 | Kosaka | 356/73 |
| 5,471,294 A | 11/1995 | Ogino | 356/73 |
| 5,548,395 A | 8/1996 | Kosaka | 356/73 |
| 5,596,401 A | 1/1997 | Kusuzawa | 356/23 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,754,291 A | 5/1998 | Kain | 356/338 |
| 5,760,899 A | 6/1998 | Eismann | 356/326 |
| RE35,868 E | 8/1998 | Kosaka | 250/574 |
| 5,831,723 A | 11/1998 | Kubota et al. | 356/73 |
| 5,859,694 A | 1/1999 | Galtier et al. | 356/28.5 |
| 6,256,096 B1 | 7/2001 | Johnson | 356/335 |

* cited by examiner

INTEGRATION OF VELOCITY DETECTOR WITH IMAGE FORMATION SYSTEM

PROCESSING A SIGNAL SEGMENT

FIG. 43  DUAL DETECTOR SYSTEM FOR CROSSCORRELATION METHOD

MEASURING THE VELOCITY OF SMALL MOVING OBJECTS SUCH AS CELLS

RELATED APPLICATION

This application is based on a prior provisional application Ser. No. 60/228,076,1 filed on Aug. 25, 2000, the benefit of the filing date of which is hereby claimed under 35 U.S.C. §119(e).

FIELD OF THE INVENTION

The present invention generally relates to a method and apparatus for measuring the velocity of an object, and more specifically, to sensing light from an object with a light sensitive detector, the amplitude of that light signal having been modulated by an optical grating, and measuring the velocity of the object by analysis of the modulated light signal.

BACKGROUND OF THE INVENTION

Cells and cell groupings are three-dimensional (3D) objects containing rich spatial information. The distribution of a tremendous variety of bio-molecules can be identified within a cell using an ever-increasing number of probes. In the post-genome era there is mounting interest in understanding the cell, not only as a static structure, but as a dynamic combination of numerous interacting feedback control systems. This understanding can lead to new drugs, better diagnostics, more effective therapies, and better health care management strategies. However, this understanding will require the ability to extract a far greater amount of information from cells than is currently possible.

The principal technologies for cellular analysis are automated microscopy and flow cytometry. The information generated by these mature technologies, although useful, is often not as detailed as desired. Automated microscopy allows two-dimensional (2D) imaging of from one to three colors of cells on slides. Typical video frame rates limit kinetic studies to time intervals of 30 ms.

Instruments known as flow cytometers currently provide vital information for clinical medicine and biomedical research by performing optical measurements on cells in liquid suspension. Whole blood, fractionated components of blood, suspensions of cells from biopsy specimens and from cell cultures, and suspensions of proteins and nucleic acid chains are some of the candidates suitable for analysis by flow cytometry. In flow cytometers specialized for routine blood sample analysis, cell type classification is performed by measuring the angular distribution of light scattered by the cells and the absorption of light by specially treated and stained cells. The approximate numbers of red blood cells, white blood cells of several types, and platelets are reported as the differential blood count. Some blood-related disorders can be detected as shifts in optical characteristics, as compared to baseline optical characteristics, such shifts being indicative of morphological and histochemical cell abnormalities. Flow cytometers have been adapted for use with fluorescent antibody probes, which attach themselves to specific protein targets, and for use with fluorescent nucleic acid probes, which bind to specific DNA and RNA base sequences by hybridization. Such probes find application in medicine for the detection and categorization of leukemia, for example, in biomedical research, and drug discovery. By employing such prior art techniques, flow cytometry can measure four to ten colors from living cells. However, such prior art flow cytometry offers little spatial resolution, and no ability to study a cell over time. There is clearly a motivation to address the limitations of existing cell analysis technologies with a novel platform for high speed, high sensitivity cell imaging.

A key issue that arises in cell analysis carried out with imaging systems is the measurement of the velocity of a cell or other object through the imaging system. In a conventional time-domain methodology, cell velocity is measured using time-of-flight (TOF). Two detectors are spaced a known distance apart and a clock measures the time it takes a cell to traverse the two detectors. The accuracy of a TOF measurement is enhanced by increasing detector spacing. However, this increases the likelihood that multiple cells will occupy the measurement region, requiring multiple timers to simultaneously track all cells in view. Initially, the region between the detectors is cleared before starting sample flow. As cells enter the measurement region, each entry signal is timed separately. The system is synchronized with the sample by noting the number of entry signals that occur before the first exit signal.

TOF velocity measurement systems are prone to desynchronization when the entry and exit signals are near threshold, noise is present, or expected waveform characteristics change due to the presence of different cell types and orientations. Desynchronization causes errors in velocity measurement which can lead to degraded signals and misdiagnosed cells until the desynchronized condition is detected and corrected. Resynchronization may require that all cells be cleared from the region between the detectors before restarting sample flow, causing the loss of sample.

Significant advancements in the art of flow cytometry are described in commonly assigned U.S. Pat. No. 6,249,341, issued on Jun. 19, 2001, and entitled IMAGING AND ANALYZING PARAMETERS OF SMALL MOVING OBJECTS SUCH AS CELLS, as well as in commonly assigned U.S. Pat. No. 6,211,955, issued on Apr. 3, 2001, also entitled IMAGING AND ANALYZING PARAMETERS OF SMALL MOVING OBJECTS SUCH AS CELLS. The specifications and drawings of each of these patents are hereby specifically incorporated herein by reference.

The inventions disclosed in the above noted patents perform high resolution, high-sensitivity 2D and 3D imaging using time delay integration (TDI) electronic image acquisition with cells in flow. These instruments are designed to expand the analysis of biological specimens in fluid suspensions beyond the limits of conventional flow cytometers. TDI sensors utilize solid-state photon detectors such as charge-coupled device (CCD) arrays and shift lines of photon-induced charge in synchronization with the flow of the specimen. The method allows a long exposure time to increase a signal-to-noise ratio (SNR) in the image while avoiding blurring. However, precise synchronization of the TDI detector timing with the motion of the moving targets is required. For example, if a target is to traverse 100 lines of a TDI sensor to build an image, and the blurring is expected to be less than a single line width, then the velocity of the target must be known to less than one percent of its actual value. It would thus be desirable to provide method and apparatus capable of producing highly accurate flow velocity for such moving targets.

Several methods have been suggested in the prior art to address the limitations of TOF velocity measurements, and to achieve highly accurate flow velocity for moving targets such as cells. One such technique is laser Doppler anemometry (LDA), in which one or more laser beams are used to interrogate a moving target. The Doppler frequency shift is detected as modulation from the interference of multiple beams that have traversed different paths in the apparatus. An example of such an apparatus is disclosed in U.S. Pat. No. 3,832,059, issued on Aug. 27, 1974, and entitled FLOW VELOCITY MEASURING ARRANGEMENT UTILIZING LASER DOPPLER PROBE. That apparatus employs two laser beams that are directed toward a moving target at converging angles. The back-scattered light from both beams is collected and focused on a common photodetector. Coherent interference at the detector generates modulation with frequency equal to twice the Doppler shift frequency, allowing the detection of the target velocity. While LDA is a functional technique, the LDA systems described in U.S. Pat. No. 3,832,059 are elaborate, expensive, and prone to instability.

In an attempt to overcome the problem of instabilities in the laser wavelength, an improved LDA apparatus is disclosed in U.S. Pat. No. 5,229,830, issued on Jul. 20, 1993, and entitled DOPPLER VELOCIMETER. In this improved apparatus, a rotating grating is added for the purpose of extracting diffraction side lobes for use in interrogating the target. This approach eliminates the wavelength dependency in the velocity measurement, but adds even more cost and complexity to the velocimeter.

An alternative approach to measuring object velocity by coherent light interference is found in LDA instruments that generate fringe patterns in the measurement field. Multiple laser beams create either stationary or propagating fringe patterns with known periods. Objects crossing the fringes modulate the light collected by the instruments. The modulation frequency is equal to the velocity divided by the fringe pattern period. LDA instruments of this type are disclosed in U.S. Pat. No. 4,148,585, issued on Apr. 10, 1979, and entitled THREE DIMENSIONAL LASER DOPPLER VELOCIMETER; and in U.S. Pat. No. 5,160,976, issued on Nov. 3, 1992, and entitled OPTICAL DETERMINATION OF VELOCITY USING CROSSED INTERFERENCE FRINGE PATTERNS. The apparatus disclosed in the first of these two patents uses a rotating diffraction grating and a beam splitter to generate four interrogation beams, which are then crossed in various combinations to measure velocity as a 3D vector. The apparatus disclosed in U.S. Pat. No. 5,160,976 uses specially constructed optical fiber bundles and two lasers of differing wavelength to generate two fringe patterns at the target, such that the patterns are oriented perpendicular to one another, in order to measure velocity as a 2D vector. Such fringe pattern velocimeters have been adapted for use in mapping complex flow fields. However, the cost, complexity, and instability inherent in delivering multiple coherent beams to the sample volume, with tightly constrained wavelengths and alignments, is a deterrent to their use. It would be desirable to provide an alternative method and apparatus to measure the velocity of an object entrained in a flow of fluid which is less costly, and more forgiving than these prior solutions to this problem.

The LDA systems described above rely on the mechanisms of Doppler shift and wave interference for the measurement of velocity. An alternative approach to measuring the velocity of objects in fluids is to collect data in short bursts at carefully timed intervals, i.e., to collect stroboscopic snapshots of the objects. This approach, which is related to but more complicated than the TOF method described above, is called object imaging velocimetry (PIV). One such system is disclosed in U.S. Pat. No. 4,729,109, issued on Mar. 1, 1988, and entitled METHOD AND APPARATUS FOR MEASURING THE DISPLACEMENTS OF PARTICLE IMAGES FOR MULTIPLE EXPOSURE VELOCIMETRY. In this patent, a strobe light source illuminates the target field. Cylindrical lenses collapse the image of the field into two orthogonal linear projections which are captured by linear arrays of photodetectors. Signals are collected from the detector arrays for every flash of the strobe light. For each axis, the signal from a first exposure is correlated with the signal from the subsequent exposure to measure target displacement. The displacement is converted to velocity by dividing the displacement by the time between exposures. The apparatus forms images in which contrast is created by light absorption by the target.

A PIV instrument utilizing target fluorescence is disclosed in U.S. Pat. No. 5,333,044, issued on Jul. 26, 1994, and entitled FLUORESCENT IMAGE TRACKING VELOCIMETER. In the apparatus described in this patent, a planar region in the field of flow is illuminated using a strobe-coherent light source. A detector forms 2D images of the fluorescent emission of objects stained with a fluorescent dye. Computer analysis of the sequence of captured images is used to track the motion of objects in the plane of illumination.

It should be noted that the stabilization and alignment of PIV systems are less problematic than in LDA systems, but the PIV systems require pulsed illumination or gated data acquisition to establish timing. The PIV systems also require arrays of detectors and elaborate data analysis to yield velocity measurements.

A technology that provides a simple, cost-effective alternative to LDA and PIV for measuring object velocity in fluids is based on the insertion of a grating with alternating opaque and transparent parallel bars in the light path of the photosensor. Light from moving objects is modulated by the optical grating pattern to create a signal with frequency directly proportional to the component of velocity perpendicular to the optical grating bars. If object motion is constrained to this perpendicular direction, then the frequency is equal to the true velocity divided by the period, or pitch, of the optical grating. A laser velocimeter based on this principle for measuring the velocity of a reflective surface moving relative to the instrument is disclosed in U.S. Pat. No. 3,432,237, issued on Mar. 11, 1969, and entitled VELOCITY MEASURING DEVICE. In the disclosed system of this patent, the target surface is illuminated with a continuous wave laser and light scattered by the moving surface is collected by a lens and then delivered to a photosensitive detector through a grating. The bars of the optical grating are oriented perpendicular to the axis of motion. An electronic frequency measuring circuit is used to determine the frequency of the photosensitive detector. The frequency is conveyed directly to a display device for viewing and conversion to velocity.

The application of this method to objects suspended in fluid is disclosed in U.S. Pat. No. 3,953,126, issued on Apr. 27, 1976, and entitled OPTICAL CONVOLUTION VELOCIMETER. In the disclosed apparatus of this patent, light collimated by a lens passes through the flow of fluid and is reflected by a mirror with alternating bars of reflective and absorptive material. The reflective bars return light through the flow of fluid to be collected by the lens. The lens focuses the reflected light on a photosensitive detector. An electronic circuit is used to estimate the frequency of the detector signal and to deliver the frequency to a display device for viewing.

It should be noted that the hardware signal processors used in early implementations of laser velocimeters have largely been displaced by computation-based digital signal processors. The demands on the photosensor signal processors vary with the nature of the application, but the most stringent applications demand high speed and high accuracy, under conditions of low SNR and rapidly varying flow velocity.

An example of an effective method for extracting velocity from the photosensor signal of a grating-based laser velocimeter is disclosed in U.S. Pat. No. 5,859,694, issued on Jan. 12, 1999, and entitled OPTICAL VELOCIMETER PROBE. In this patent, the digitized photosensor signal is captured in blocks of samples for processing. For each block, the signal processor executes the steps of generating a complex signal using the Hilbert transform, autocorrelating the complex signal, and extracting the phase for each time sample of the autocorrelogram. The autocorrelation is performed using the steps of a complex Fourier transformation, squaring the magnitude of the spectrum, and then applying an inverse Fourier transformation. Finally, an optimization routine finds a best-fit velocity value for the phase samples. The method described in this patent has the advantage of building SNR and delivering accurate velocity estimates, given long signal segments. However, the method is computation intensive, limiting the rate at which the velocity estimate is updated.

It would be desirable to utilize the principal of modulation of light from moving objects by the insertion of a periodic grating into the detector path for the purpose of measuring object velocity, and to further employ improved signal processing, superior control system design, and/or a unique grating design to achieve high precision velocity measurements in an imaging flow cytometer.

SUMMARY OF THE INVENTION

The present invention is directed to a system and method for determining a velocity of an object. This method will preferably be employed in conjunction with an imaging or optical system that is adapted to determine one or more characteristics of an object from an image of the object or light from the object. There is relative movement between the object and the imaging system, and although it is contemplated that either, or both, the object and imaging system may be in motion, the object will preferably be in motion and the imaging system will be fixed. When used in conjunction with an imaging system that incorporates a TDI detector, the velocity determined according to the present invention is used to provide a clocking signal to synchronize the TDI detector with the movement of the image over the TDI detector.

It should be understood that while portions of the following description, and the claims that follow, refer to "an object," it is clearly contemplated that the present invention is intended to be used with a plurality of objects, and is particularly useful in connection with imaging a stream of objects. In at least one embodiment, the stream of objects comprises moving cells or cell clusters. Furthermore, while the examples cited herein primarily relate to measuring the velocity of objects such as cells flowing in a stream of liquid, the present invention applies as well to objects attached to a solid substrate moving relative to the imaging system and to particles or liquid droplets flowing in a stream of gas.

Fundamental to the present invention are the illumination of an object, and the detection of light from the object. For the purpose of velocity measurement, the detected light must carry information about the change of position of the object over time. The object may modify the illumination light by scattering, refraction, diffraction, or absorption so that its wavelength is the same as that of the light received by the detector. Alternatively, fluorescence or phosphorescence at the object caused by the illumination light may result in light of different wavelengths than the illumination light to be received at the detector. Furthermore, the object may emit light used to determine the velocity of the object, without requiring prior illumination of the object by another light source.

The basic velocity measuring system includes "a sensitive volume," through which objects, preferably entrained in a fluid, are illuminated. Light from the objects is directed along a collection path. The collected light is first converted into an electrical signal, and then the electrical signal is digitized. The digitized signal is analyzed to extract the velocity of an object. Thus, the velocity measuring system will preferably include a light source that illuminates the objects in motion (unless the object self-emit light without any need for illumination by a light source), a light sensitive detector for receiving light from the objects, and electronic components to manipulate the signal from the light sensitive detector to determine a velocity. The light source may be a laser, a light emitting diode, a filament lamp, or a gas discharge arc lamp, for example, combined with optical conditioning elements such as lenses, apertures, and filters to deliver the desired wavelength(s) of light to the object at an intensity required for determination of the velocity of the object. The detector may be a photomultiplier tube or a solid-state photodetector and may be combined with optical conditioning elements such as lenses, apertures, and filters to deliver the desired wavelengths of light from the object to the detector.

Light from the object is received as the object passes through the sensitive volume. Because the sensitive volume is bounded by a profile of an illumination field and by an acceptance window of the light sensitive detector, it would be possible to estimate the velocity of the object from the time required for the object to pass through the sensitive volume. However, the sensitive volume is bounded by gradients rather than distinct edges, and it may be impractical to maintain the dimensions of the sensitive volume with a high degree of accuracy.

To address the above-noted problem, one or more optical gratings is used to establish a distance measurement scale for computing velocity, eliminating the concern for maintaining the dimensions of the sensitive volume with a high degree of accuracy. The optical gratings are preferably fabricated using high precision methods, such as photolithographic etching, to create patterns of alternating bars of opaque and transparent material. The accuracy required for the fabrication of the optical gratings is a function of the accuracy required in the velocity measurement. Preferably the optical grating includes alternating sequences of opaque strips and transparent strips of substantially equal width.

As noted above, when the velocity measurement system is used in conjunction with an imaging system that preferably employs a TDI detector. In TDI imaging, the charge in a TDI detector is moved in synchrony with an image that is incident on the TDI detector, enabling a thousand-fold increase in integration times over conventional frame imaging. TDI imaging is conventionally performed by clocking a pixel output from the detector using an encoder that directly measures sample movement, keeping the charge on the detector synchronized with the image. Since the transport of objects by a fluid stream prevents the use of an encoder, systems imaging objects in flow require an alternative means of synchronizing the TDI detector with the moving object and thus, with the moving image of the object across the TDI detector. The present invention provides an acceptable approach for measuring the velocity of moving objects (such as cells) for use in such TDI based imaging systems.

The present invention encompasses two different configurations of optical gratings, and two different signal processing methods, which are used to analyze the modulated signal produced by a detector in response to the modulated light produced by an optical grating, thereby enabling the velocity of an object to be determined. Preferably, each signal processing embodiment is executed under the control of a supervisory program appropriate to the particular method employed.

In one embodiment, the signal is homodyned to a baseband and the passband is limited to improve the SNR. The frequency of the modulated light is extracted in the time domain from signal packets selected for low phase interference. This method is well suited for execution in a fast pipeline processor and delivers relatively high accuracy and relatively high sensitivity. Another embodiment employs two optical gratings displaced from one another along the flow axis to modulate light from the object, so that the modulated light is incident on two different detectors. Cross-correlation of the two signals from the detectors rapidly delivers a highly accurate estimate of velocity of the object. The performance of these two embodiments is preferably optimized by the inclusion of supervisor programs, which rapidly adapt to changing flow velocity and varying signal strength from the detector(s). The choice of the embodiment that is employed will depend on the particular demands of an application for determining the velocity of an object.

More specifically, a velocity measurement system in accord with the present invention includes an optical element disposed so that light traveling from an object passing through a sensitive volume is directed by an optical element along a collection path. At least one optical grating is disposed in the collection path and modulates the light, producing modulated light having a modulation frequency corresponding to a velocity of the object. At least one light sensitive detector is disposed in the collection path and converts the modulated light into an electrical signal. The velocity measurement system also includes means for converting the electrical signal into a sequence of digital samples, and means for processing the sequence of digital samples to determine a velocity of the object corresponding to the electrical signal.

Preferably, the means for converting the electrical signal into the sequence of digital samples comprises at least one analog-to-digital converter. It is likely that most such systems will include at least one amplifier electrically coupled each light sensitive detector, for amplifying the electrical signal before conversion of the electrical signal into a sequence of digital samples. In several embodiments, bandpass filters are employed to filter the electrical signal before conversion into a sequence of digital samples. Alternatively, the electrical signal may be converted into a sequence of digital samples immediately after amplification, and a digital bypass filter may be utilized. The means for processing the sequence of digital samples can comprise a computer, an application specific integrated circuit (ASIC), or a digital oscilloscope.

Preferably, a velocity measurement system in accord with the present invention will further include a system controller for controlling the acquisition of the electrical signal, for controlling the means for converting the electrical signal into a sequence of digital samples, and for controlling the means for processing the sequence of digital samples. The system controller is preferably a computer or other programmed computing device, however, it should be understood that an ASIC can also be beneficially employed as a system controller. Preferably the system controller will regulate a gain of an amplifier that amplifies the electrical signal, regulate a threshold applied to frequency measurements so that measurements made under the condition of inadequate SNR are rejected, and/or regulate a frequency of a pair of baseband converter local oscillators in response to variations in a velocity of the object.

The light from an object passing through the sensitive volume can include light scattered by that object, an unstimulated emission from the object, or a stimulated emission from the object. While it is contemplated that the velocity measuring system and method of the present invention can use ambient light, at least one light source is preferably incorporated into such a system for illuminating the sensitive volume (unless the object self-emits light without requiring prior illumination from another source). Such a light source can also stimulate a fluorescent emission from an object passing through the sensitive volume. Incident light can be at least partially absorbed by an object passing through the sensitive volume, so that the light directed by the optical element will have been affected by the absorption of light by the object. Alternatively, incident light is reflected from an object passing through the sensitive volume toward the optical element. The light source can be one or more of a coherent light source, a non-coherent light source, a pulsed light source, a continuous light source, a continuous wave laser, a pulsed laser, a continuous wave incandescent lamp, a strobe arc lamp, and may include an optical filter for selecting a limited spectrum for illumination.

Velocity measurement systems in accord with the present invention preferably enable a flow of fluid, in which objects are entrained, to pass through the sensitive volume, such that a velocity of an object so entrained can be measured. In other embodiments, velocity measurement systems in accord with the present invention enable a support, on which objects are disposed, to pass through the sensitive volume, such that a velocity of the objects are disposed, to pass through the sensitive volume can be measured. At least one embodiment will comprise a stage-based motion system with a high-resolution linear encoder.

It is anticipated that velocity measuring systems, or combined velocity measurement and imaging systems can beneficially include a mechanism for sorting objects disposed downstream of the sensitive volume(s).

In one embodiment in which the optical grating has a uniform pitch, the means for converting the electrical signal into a sequence of digital samples includes an amplifier that produces an amplified electrical signal based on the electrical signal received from the detector. The means also includes a bandpass filter for filtering the amplified electrical signal to produce a passband signal. The means further includes a baseband converter for converting the passband signal into a pair of signals that represent the passband signal with two components, a real component and an imaginary component. Each of the two baseband signals is converted to a sequence of digital samples by an analog-to-digital converter.

For embodiments wherein the at least one optical grating has a uniform pitch, the means for processing the sequence of digital samples preferably determines the velocity from a first derivative of a time series of phase samples of the electrical signal, after calculating those phase samples from a baseband complex representation of the electrical signal. This processing of the electrical signal can be executed by a programmed computer, an ASIC, other hardwire logic circuits, or a digital oscilloscope.

In another embodiment, two substantially identical optical gratings, each having a non-uniform pattern of opaque bar and transparent gap widths, are disposed along an axis of motion of an object such that the object sequentially traverses the sections.

In one preferred embodiment that incorporates non uniform optical gratings, a beam splitter is disposed in the collection path, such that a portion of the light traveling from an object along the collection path is diverted along a second collection path. A second non uniform optical grating is disposed in the second collection path, such that the second optical grating also modulates the light, producing modulated light have a modulation frequency corresponding to a velocity of an object passing through the sensitive volume. A second light sensitive detector is disposed in the second collection path, and converts the light modulated by the second optical grating into an electrical signal.

In an embodiment incorporating two optical gratings with a non uniform pitch, the means for converting the electrical signal into a sequence of digital samples includes a first amplifier coupled to the detector that is disposed in the collection path. The first amplifier amplifies the electrical signal from a first light sensitive detector, producing an amplified electrical, and a first bandpass filter filters the amplified electrical signal to produce a first passband signal. A first analog-to-digital converter converts the passband signal to a first sequence of digital samples. The means for converting the electrical signal into a sequence of digital samples also includes a second amplifier disposed in a second collection path. The second amplifier amplifies the second electrical signal, producing a second amplified electrical signal that is filtered by a second bandpass filter, producing a second passband signal. The second passband signal is input to a second analog-to-digital converter, which converts the second passband signal to a second sequence of digital samples. Alternatively, the bandpass filter operation can be accomplished using digital bandpass filters following the analog-to-digital converters.

Preferably when two non uniform optical gratings are employed, each optical grating is aligned in series along an axis of motion corresponding to an object that the light is collected from, and the means for processing the sequence of digital samples to determine a velocity of an object calculates an amplitude peak of a cross-correlogram generated by a convolution of the electrical signal from the first light sensitive detector disposed in the collection path and the second electrical signal from the second light sensitive detector disposed in the second collection path.

Embodiments with optical gratings of non uniform pitch also preferably include a control system controllably connected to the means for converting the electrical signal into a sequence of digital samples and the means for processing the sequence of digital samples. The control system preferably regulates the gain of each amplifier in response to varying electrical signal levels, and regulates an upper and a lower limit for time shifting the cross-correlation step in response to variations in the velocity of an object.

As noted above, velocity measurement systems in accord with the present invention can be incorporated into imaging systems that also determine non-velocity characteristics of an object passing through the sensitive volume, by employing at least one TDI detector that using the velocity for a clocking function. Such combination velocity measurement and imaging systems preferably include a second optical element disposed so that light traveling from an object passing through a second sensitive volume passes through the second optical element and travels along yet another collection path, and at least one additional detector that determines a non-velocity related characteristic of an object passing through the second sensitive volume. Preferably, the second sensitive volume, the second optical element, and the at least one additional detector are disposed downstream from the sensitive volume, optical element, and light sensitive detector of the velocity measuring portion of the combined system.

It is anticipated that when the objects in question are cells, the accurate determination of cell velocity for use in a TDI-based imaging system for cell analysis, in accord with the present invention, will greatly expand the amount of information that can be extracted from cells. It is expected that the present invention will enable systems to process sample sizes of about 100 million cells, and analyze the samples with high spectral and spatial resolution, at very high speeds. Such a system will have clinical applications that include non-invasive prenatal diagnosis via maternal peripheral blood, routine cancer screening and eventually, therapeutic applications involving the isolation, modification and re-implantation of rare cells. In addition, the present invention is directed to a general purpose velocity detection method that can be applied to other applications where an accurate determination of the velocity of an object or the velocity of a flow is required.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 26:
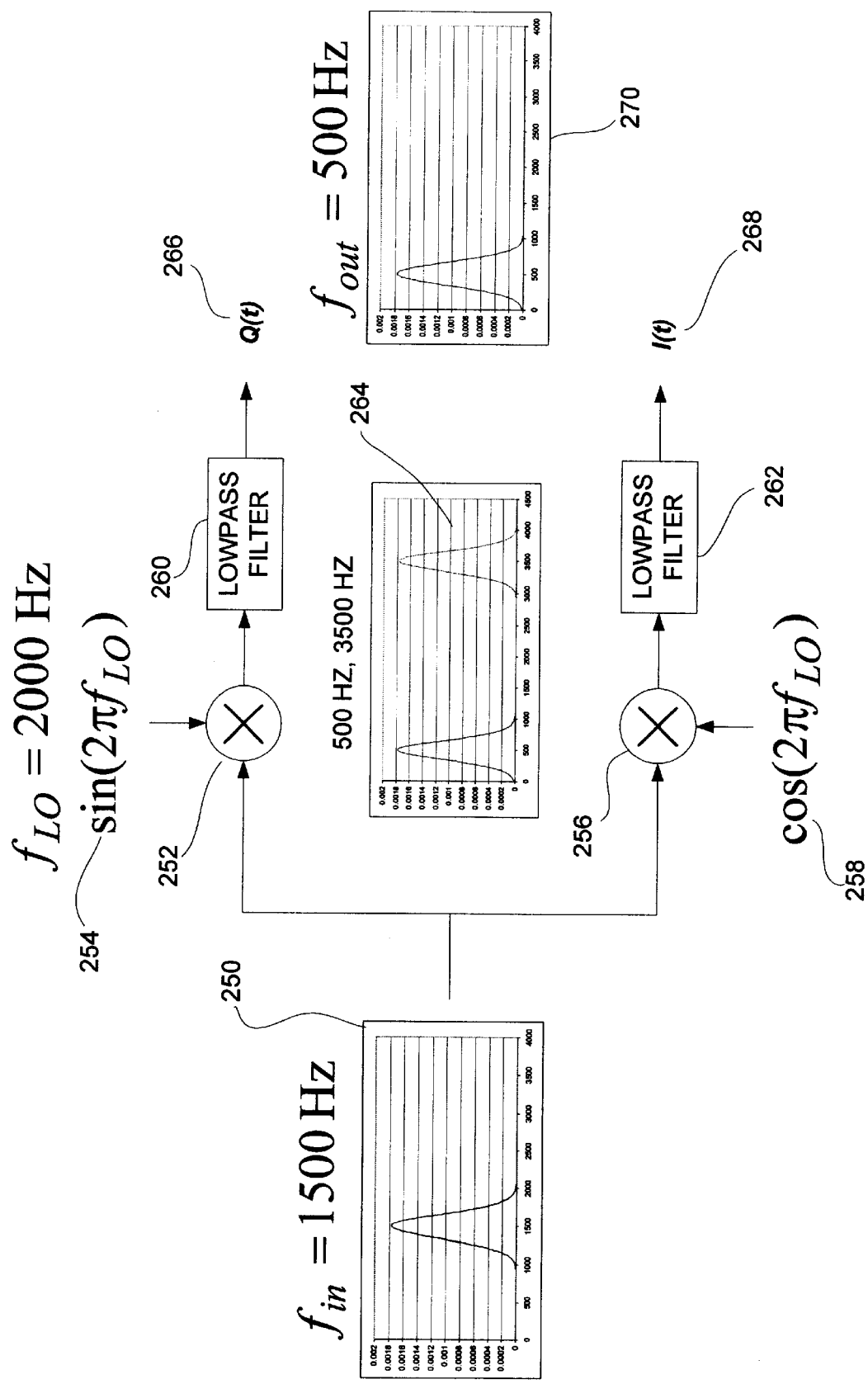
Figure 27:
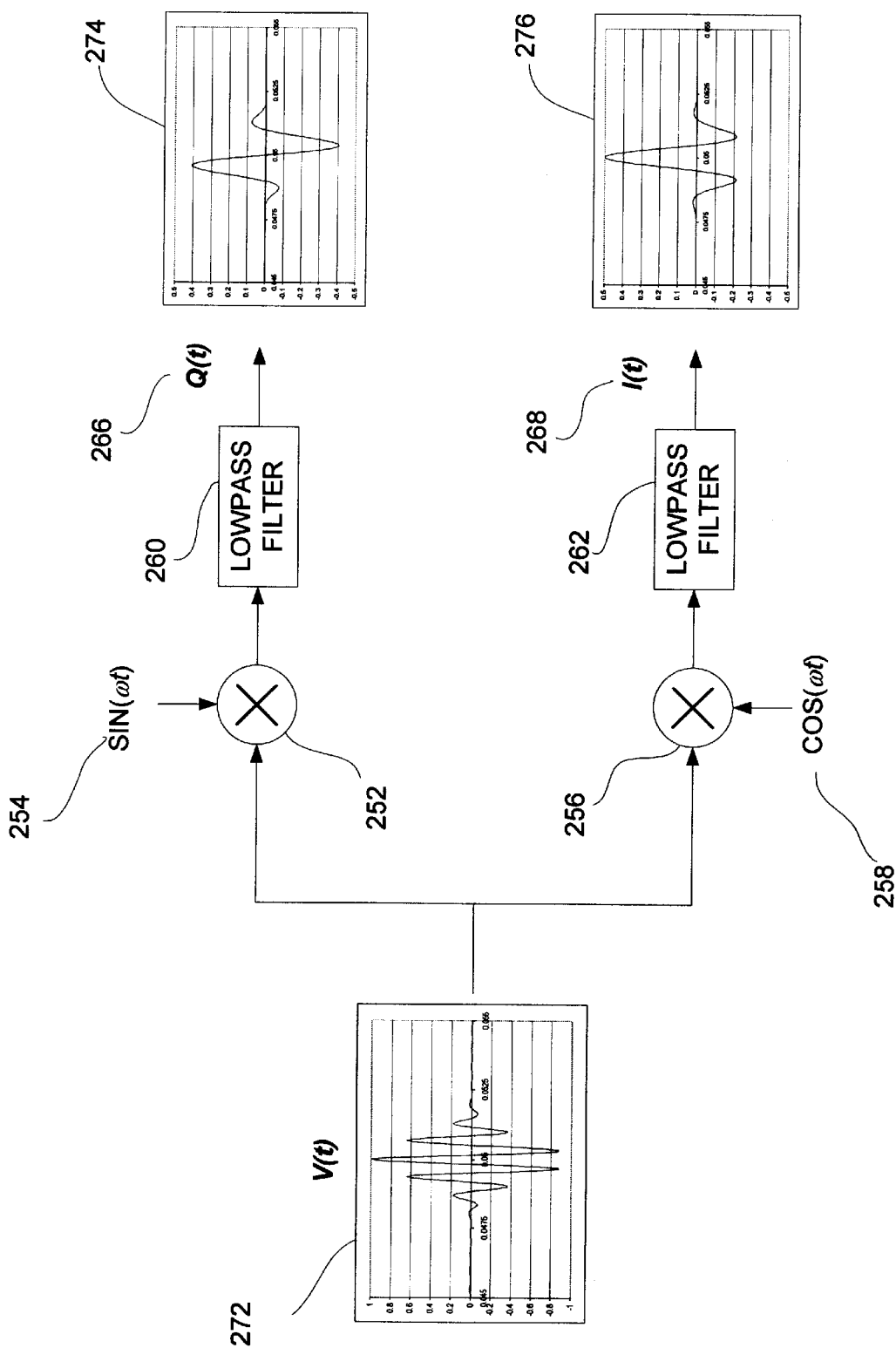
Figure 28:
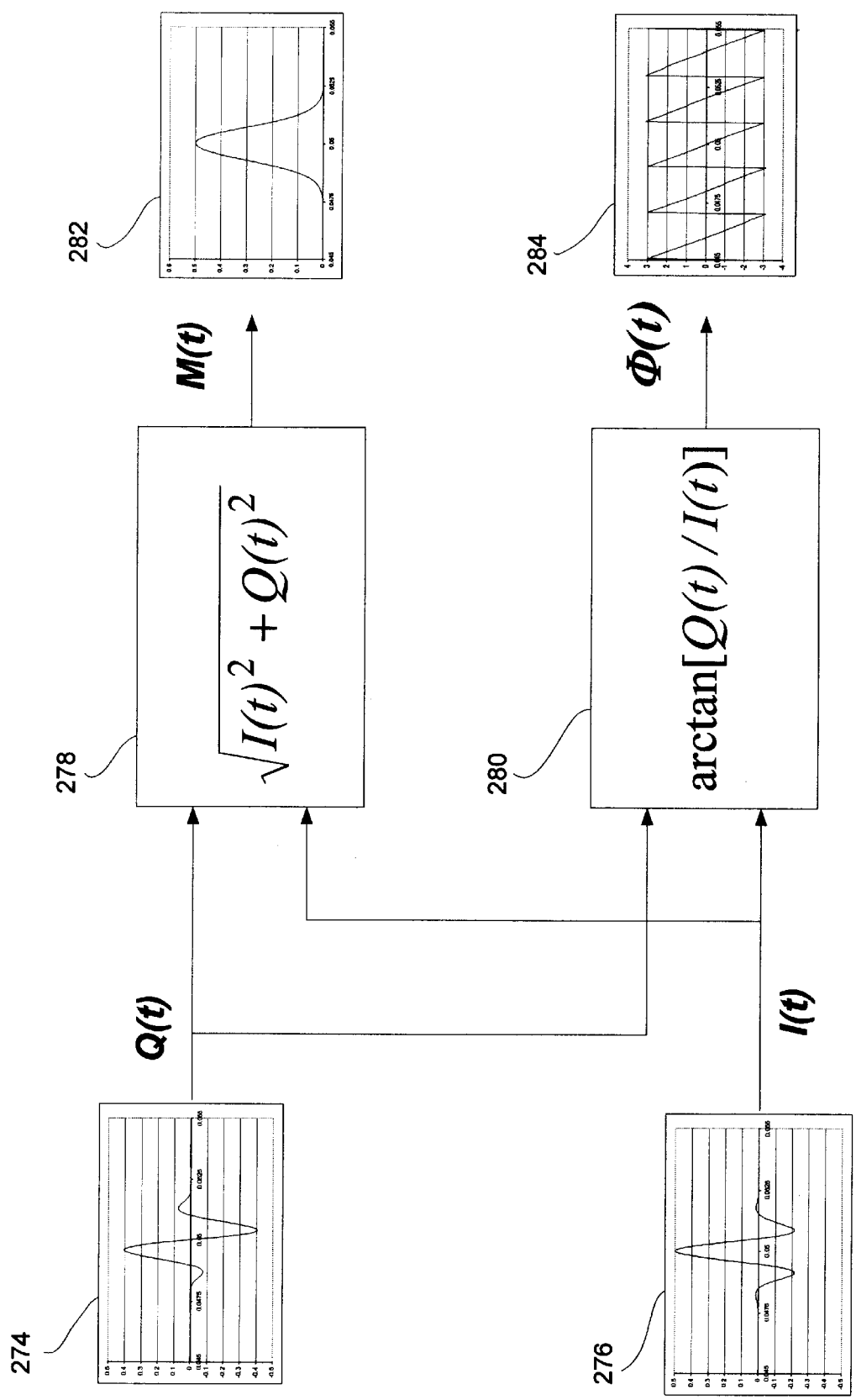
Figure 29:
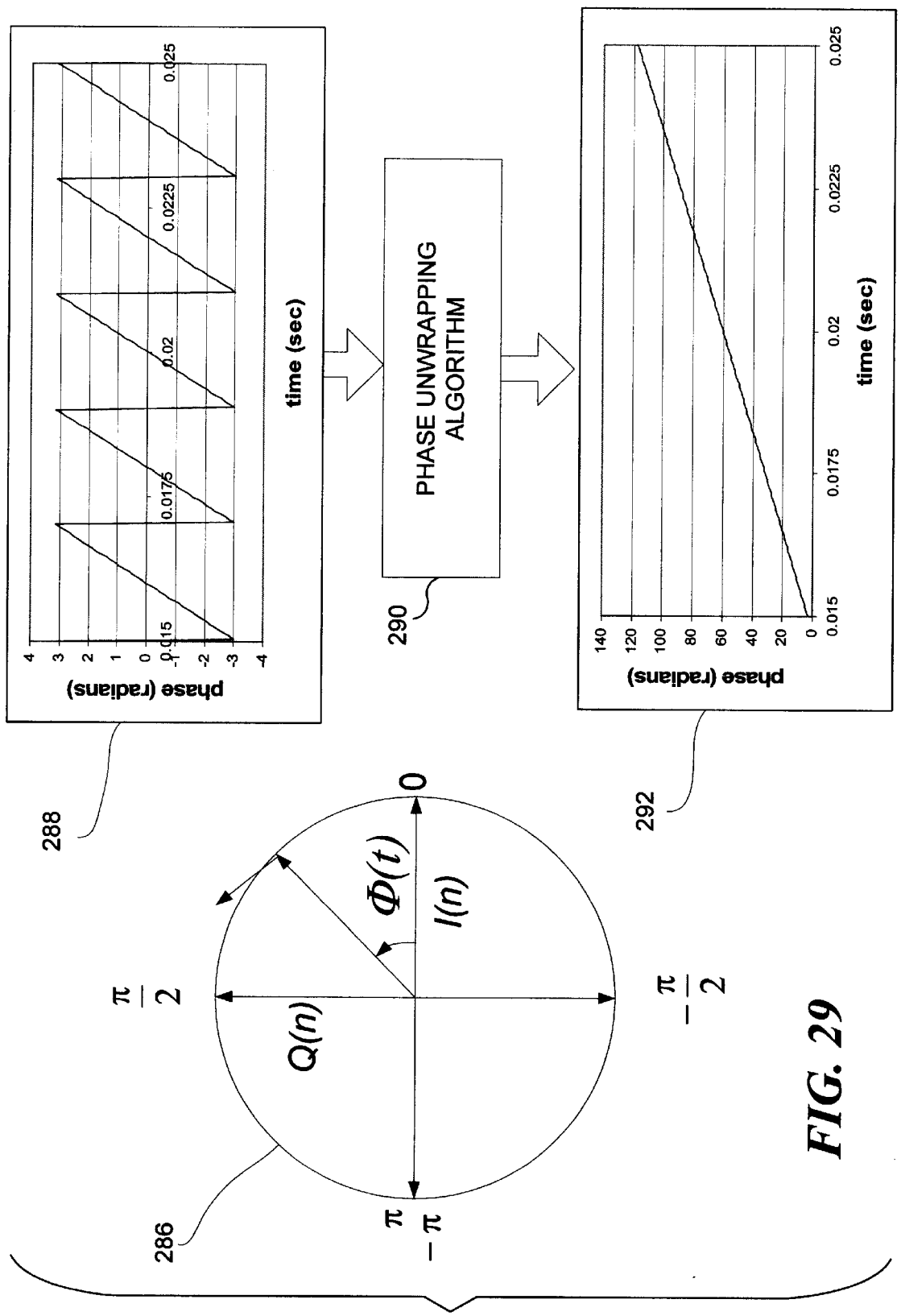
Figure 30:
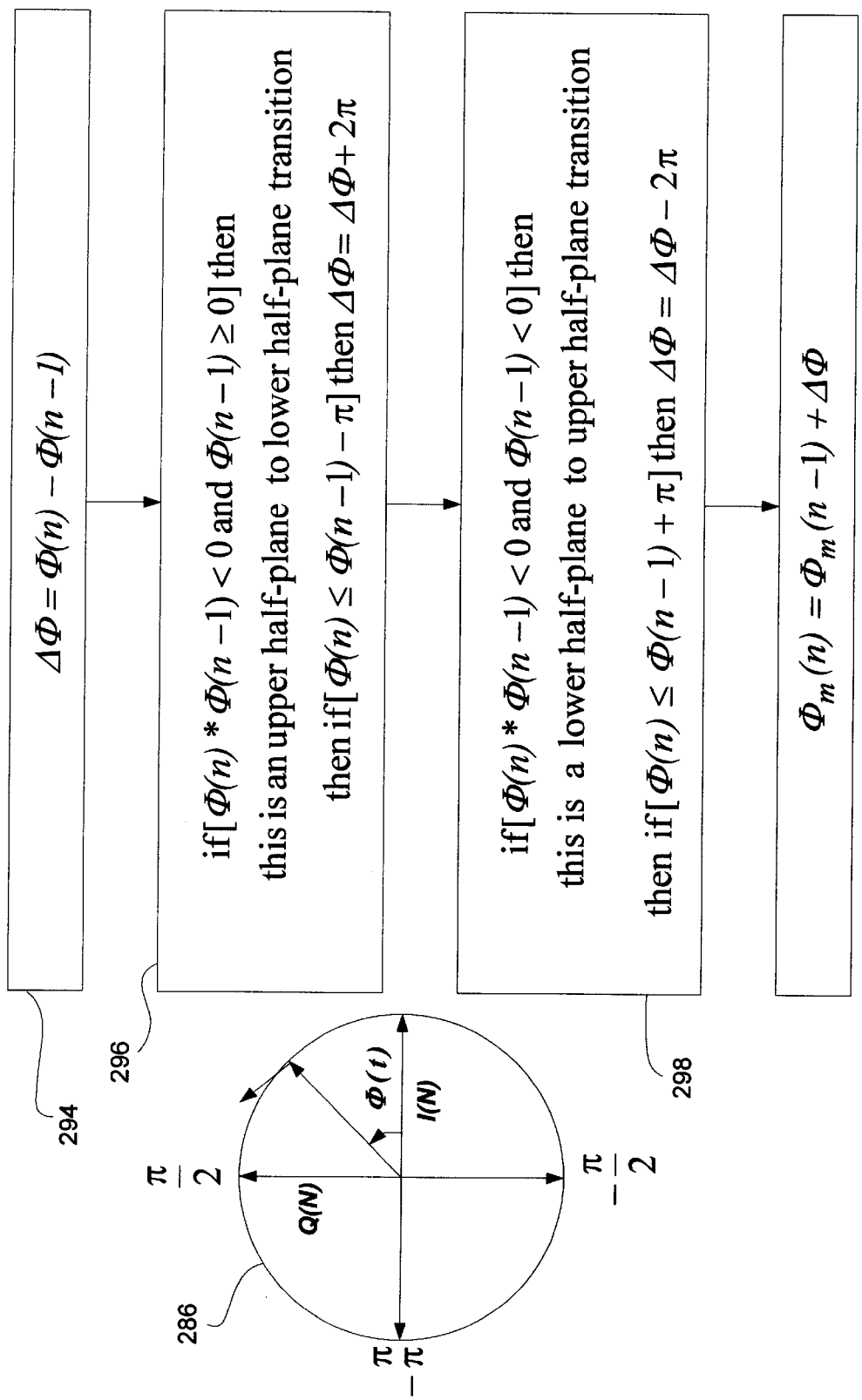
Figure 31A:
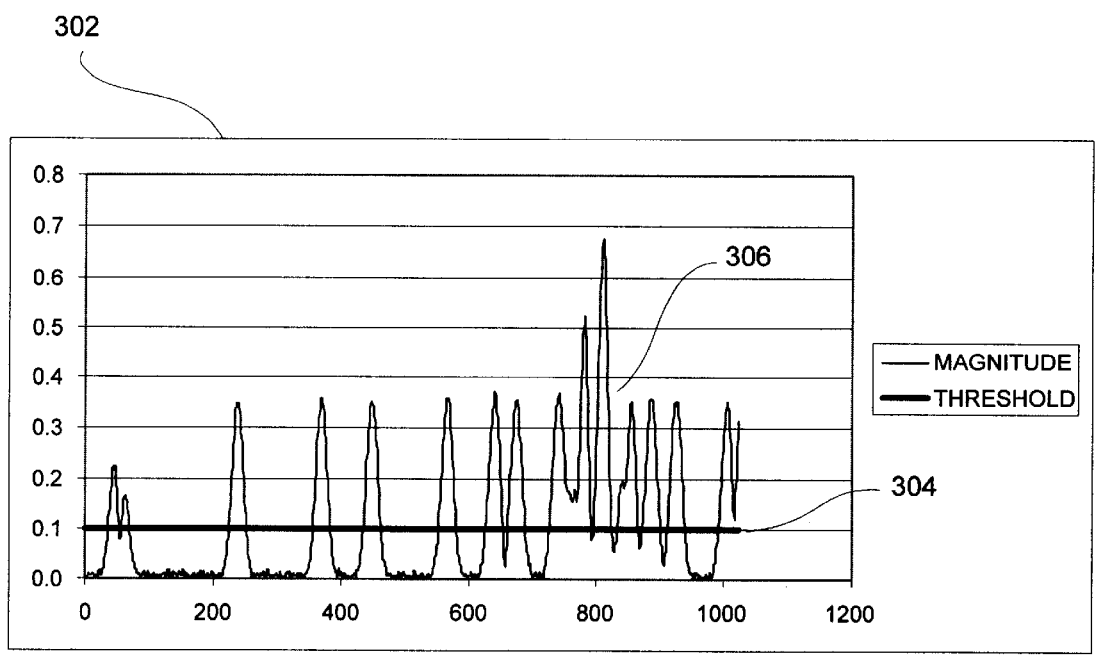
Figure 31B:
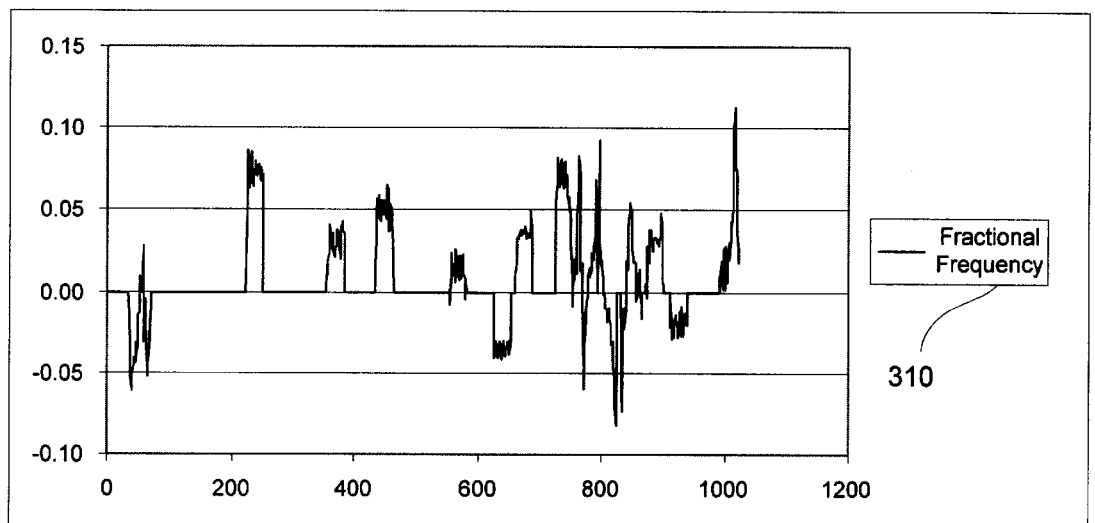
Figure 32:
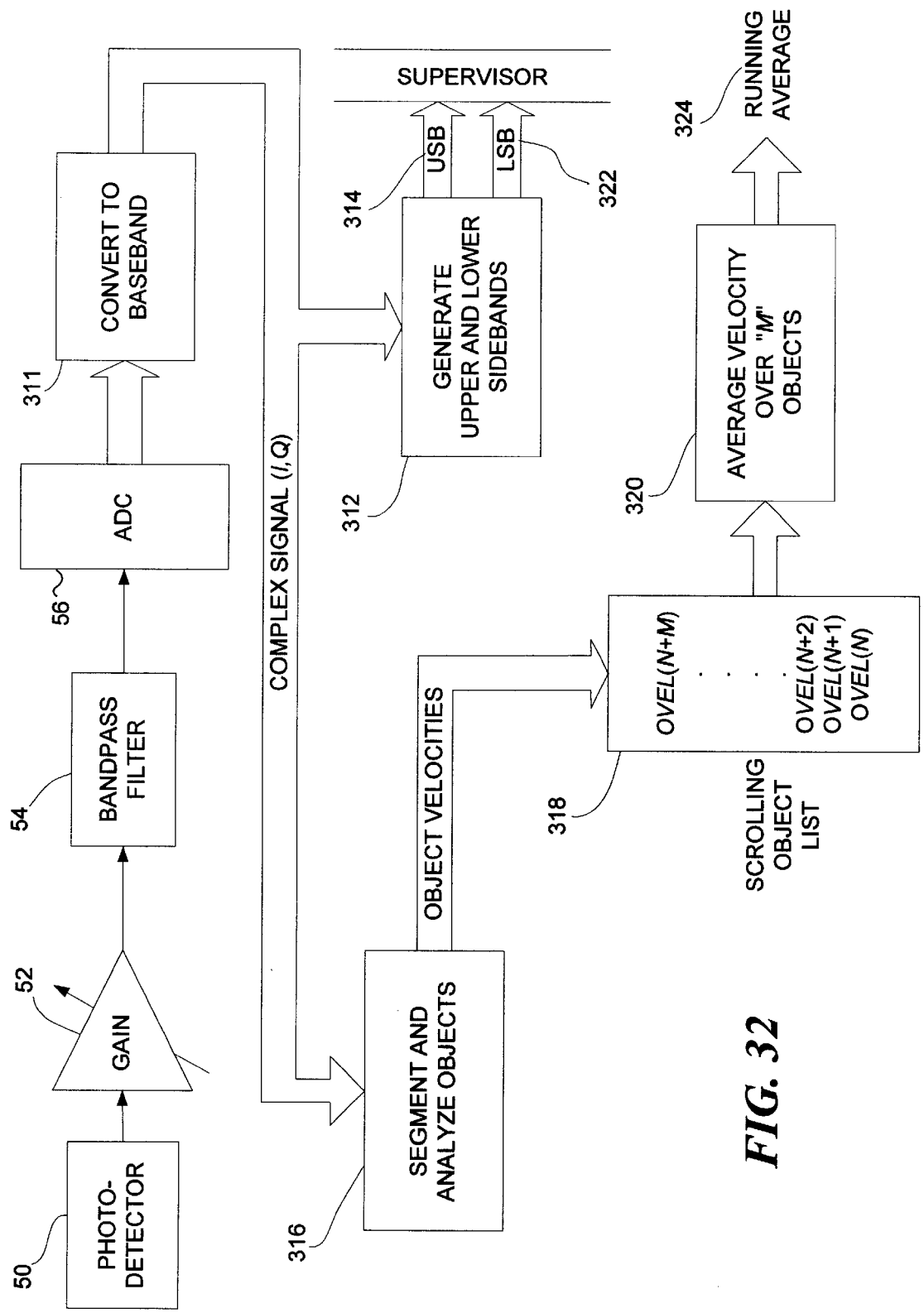
Figure 33:
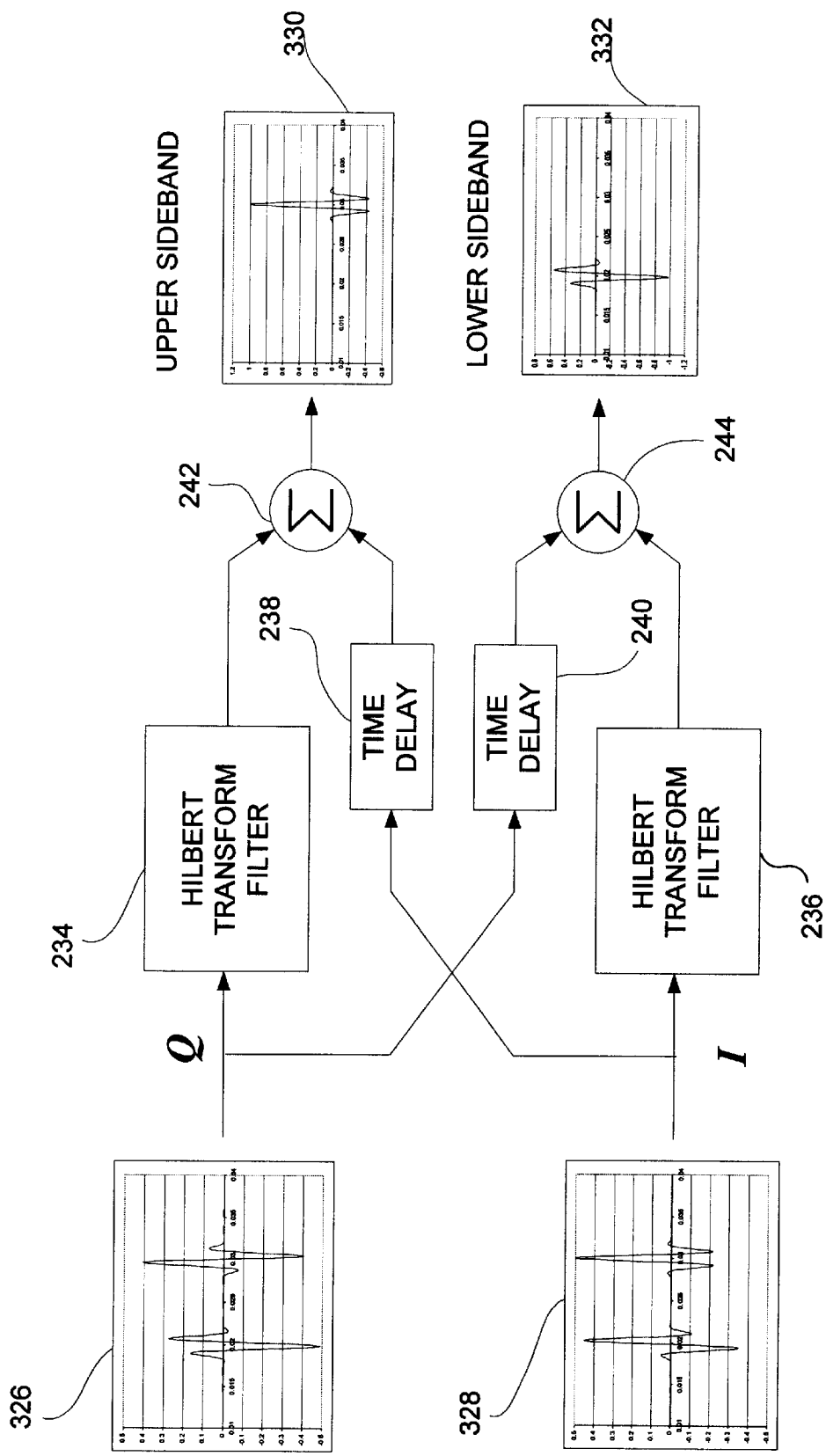
Figure 34:
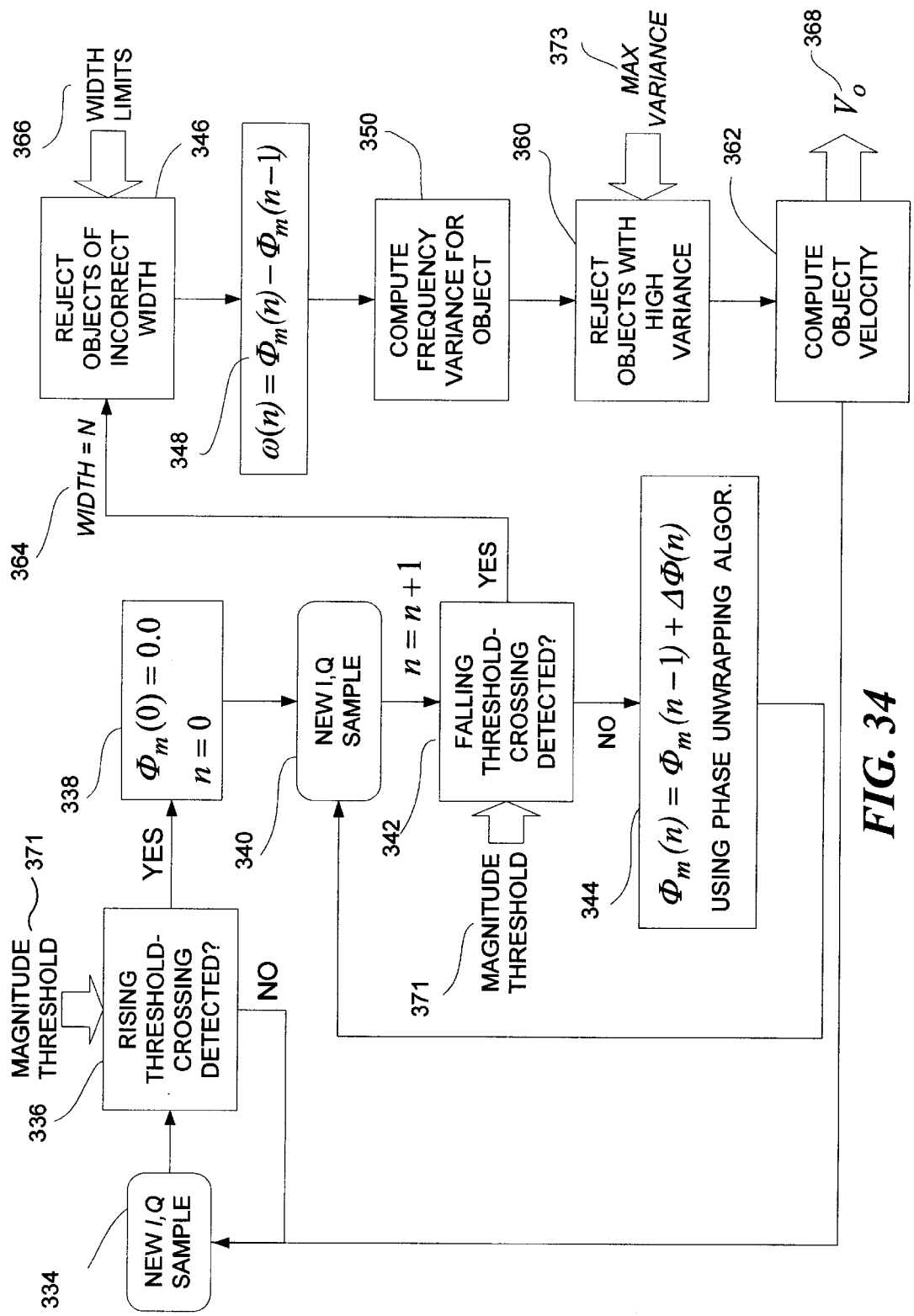
Figure 35A:
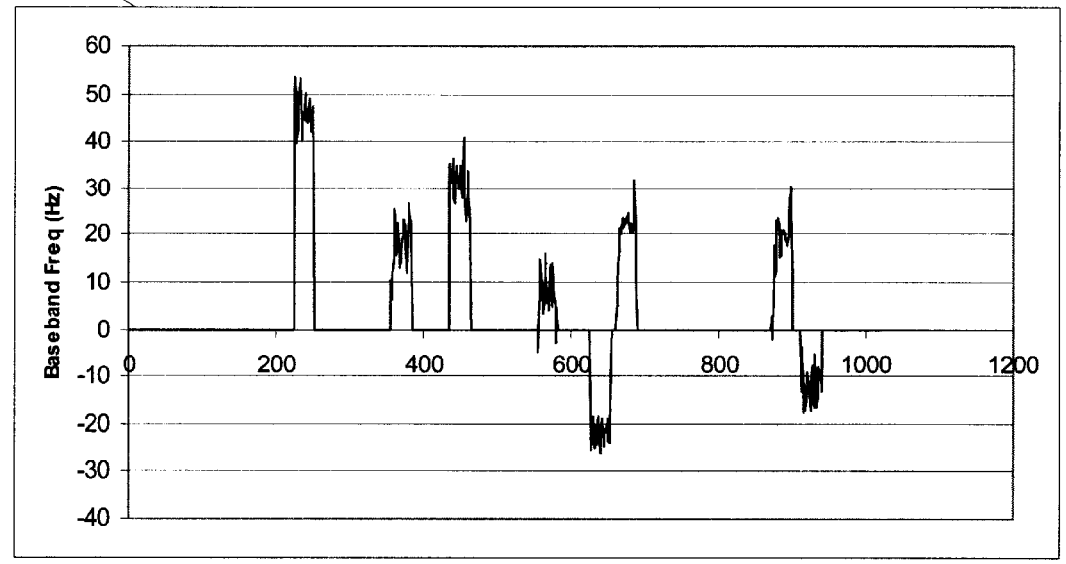
Figure 35B:
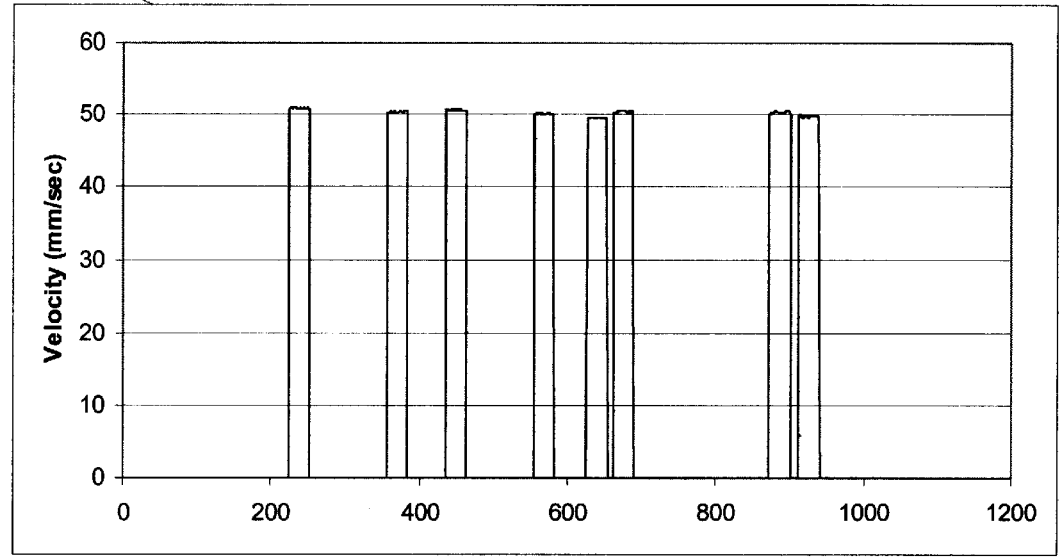
Figure 36:
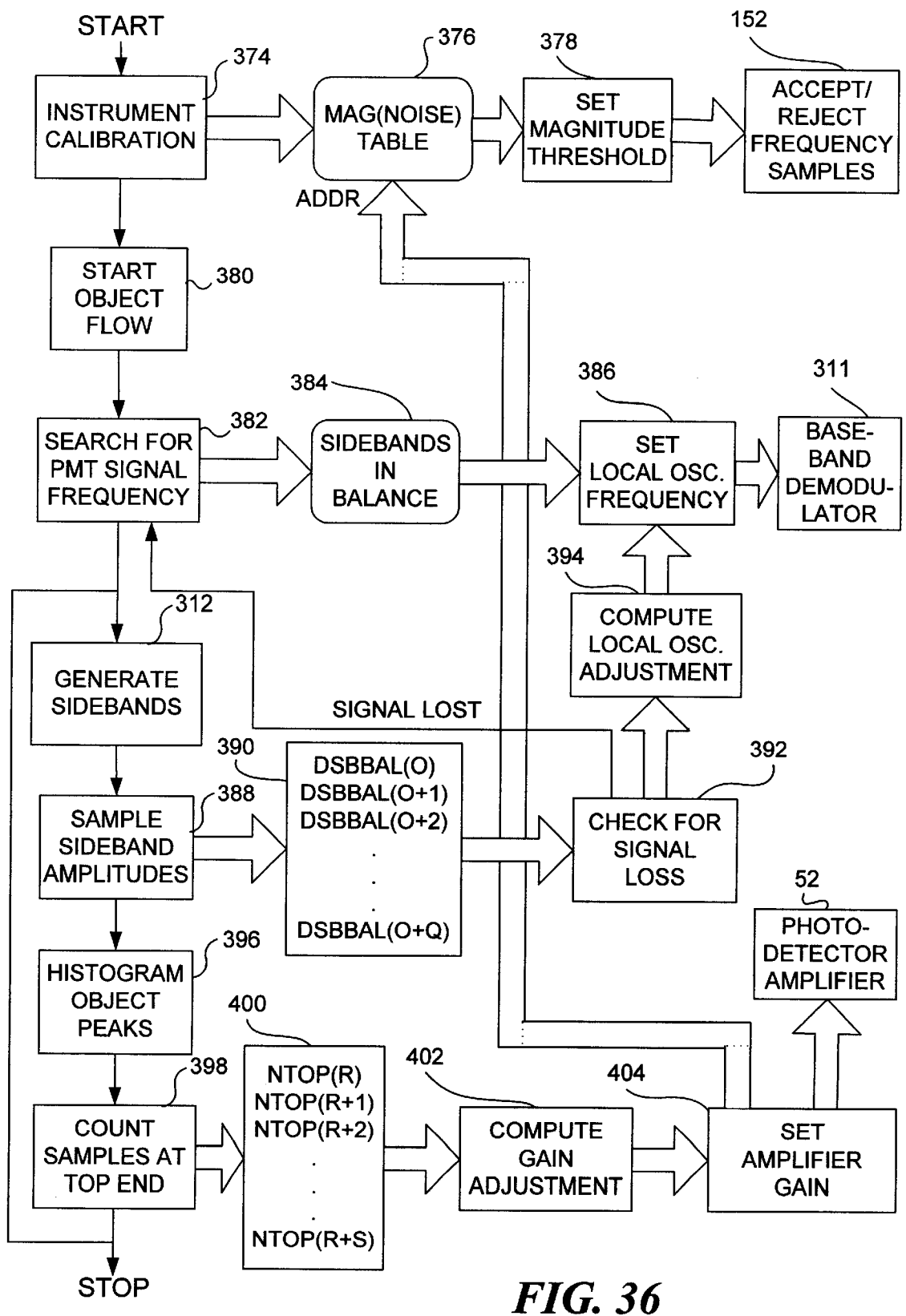
Figure 37:
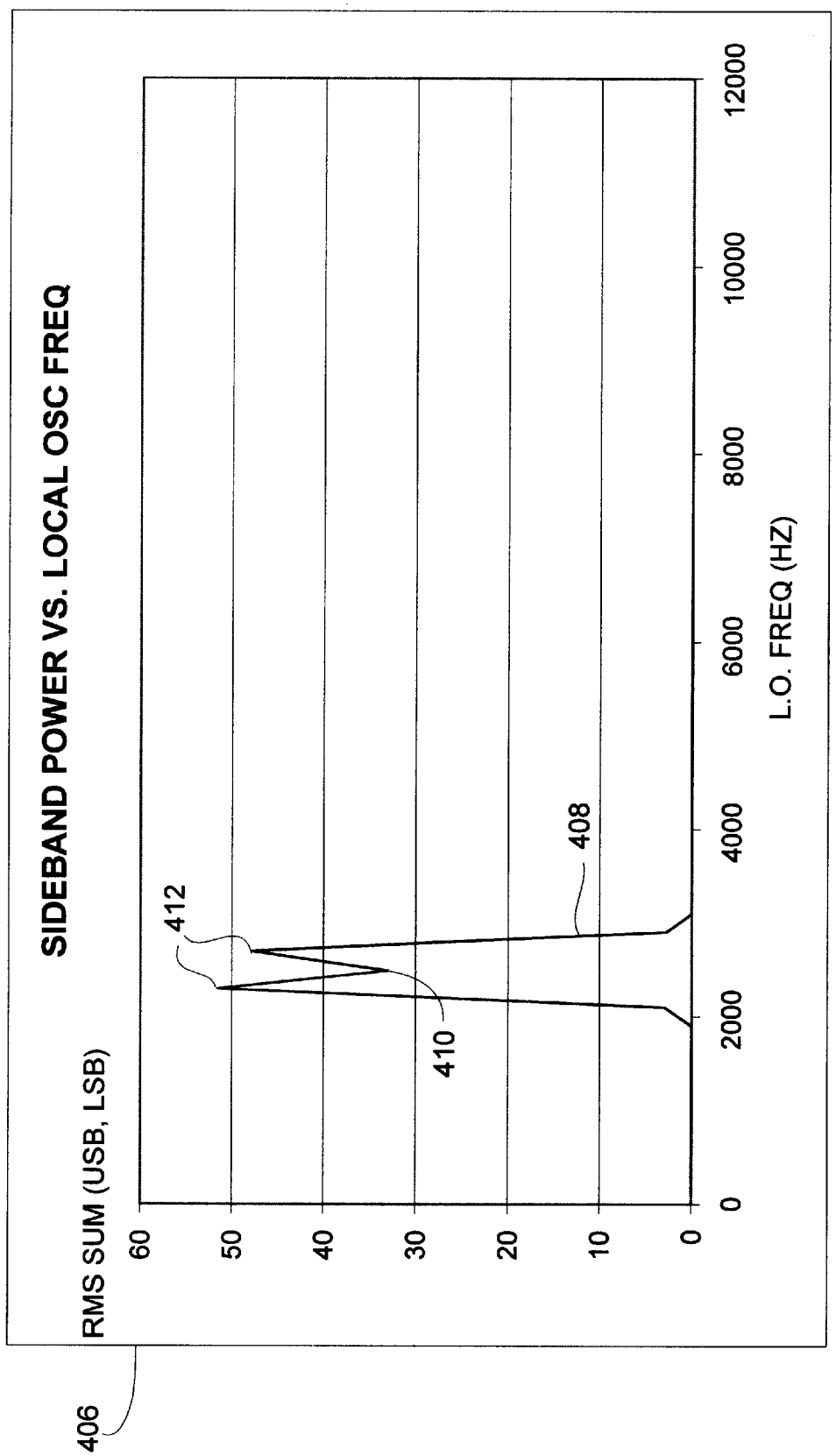
Figure 38:
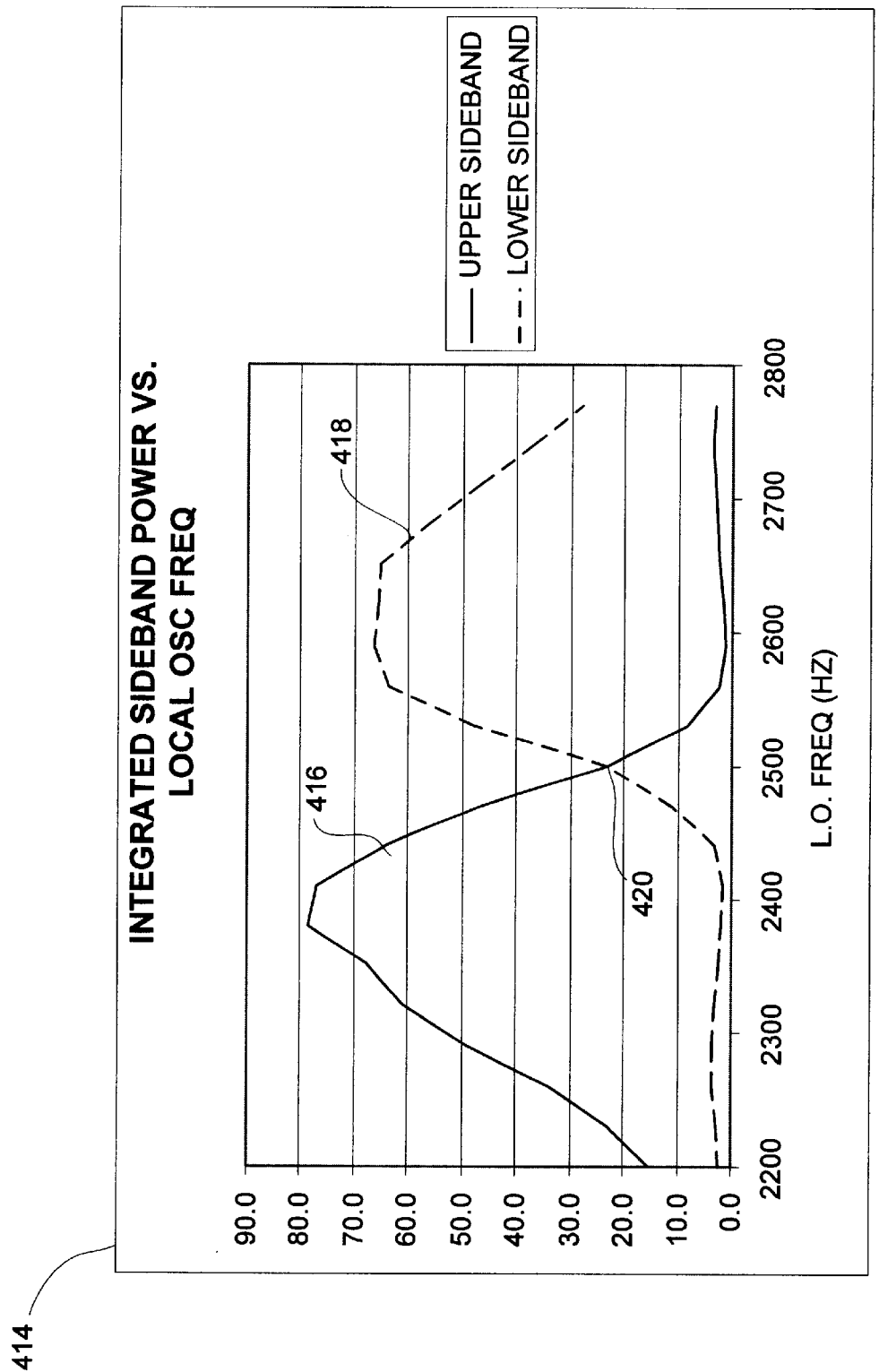
Figure 39:
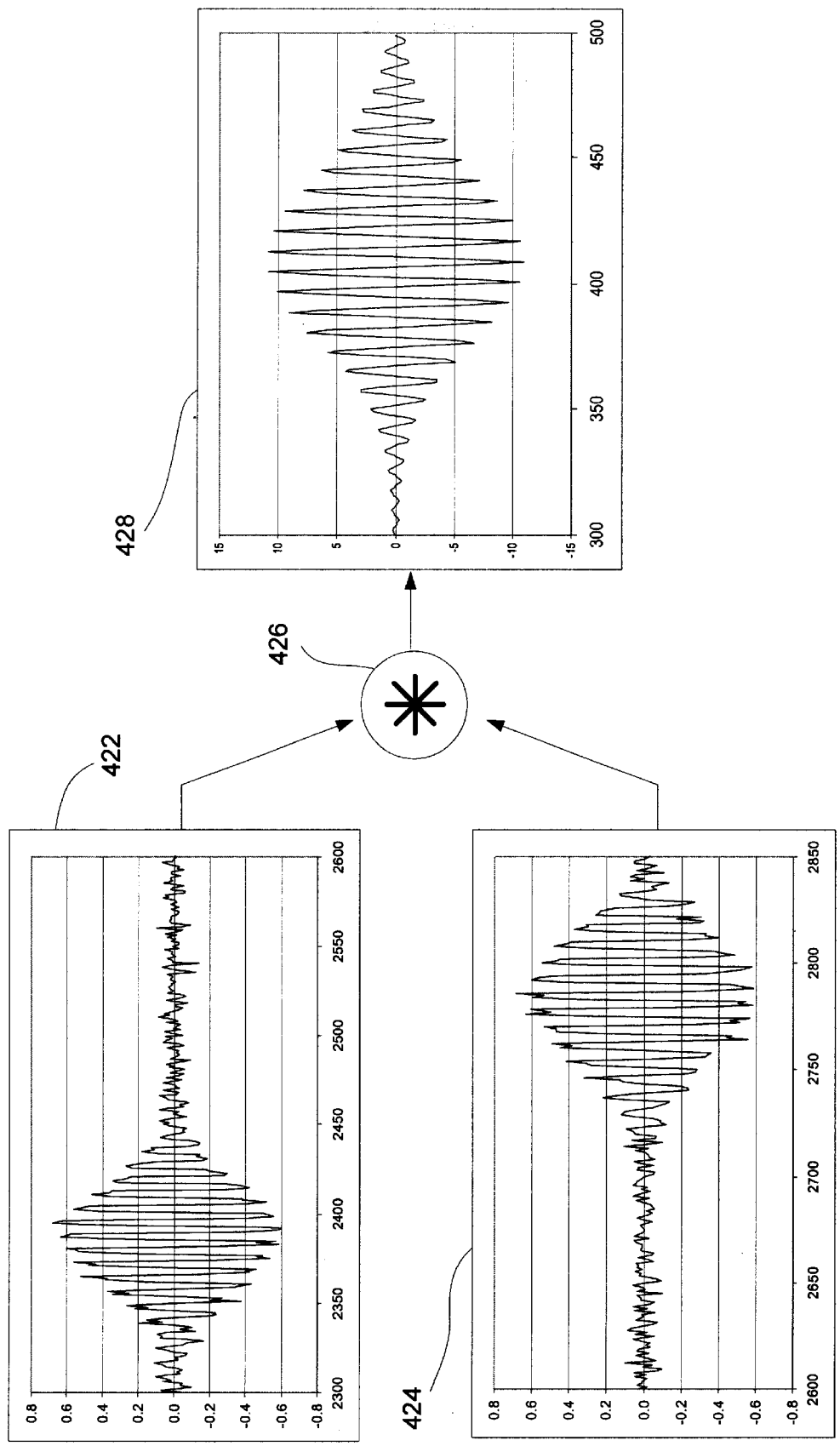
Figure 40:
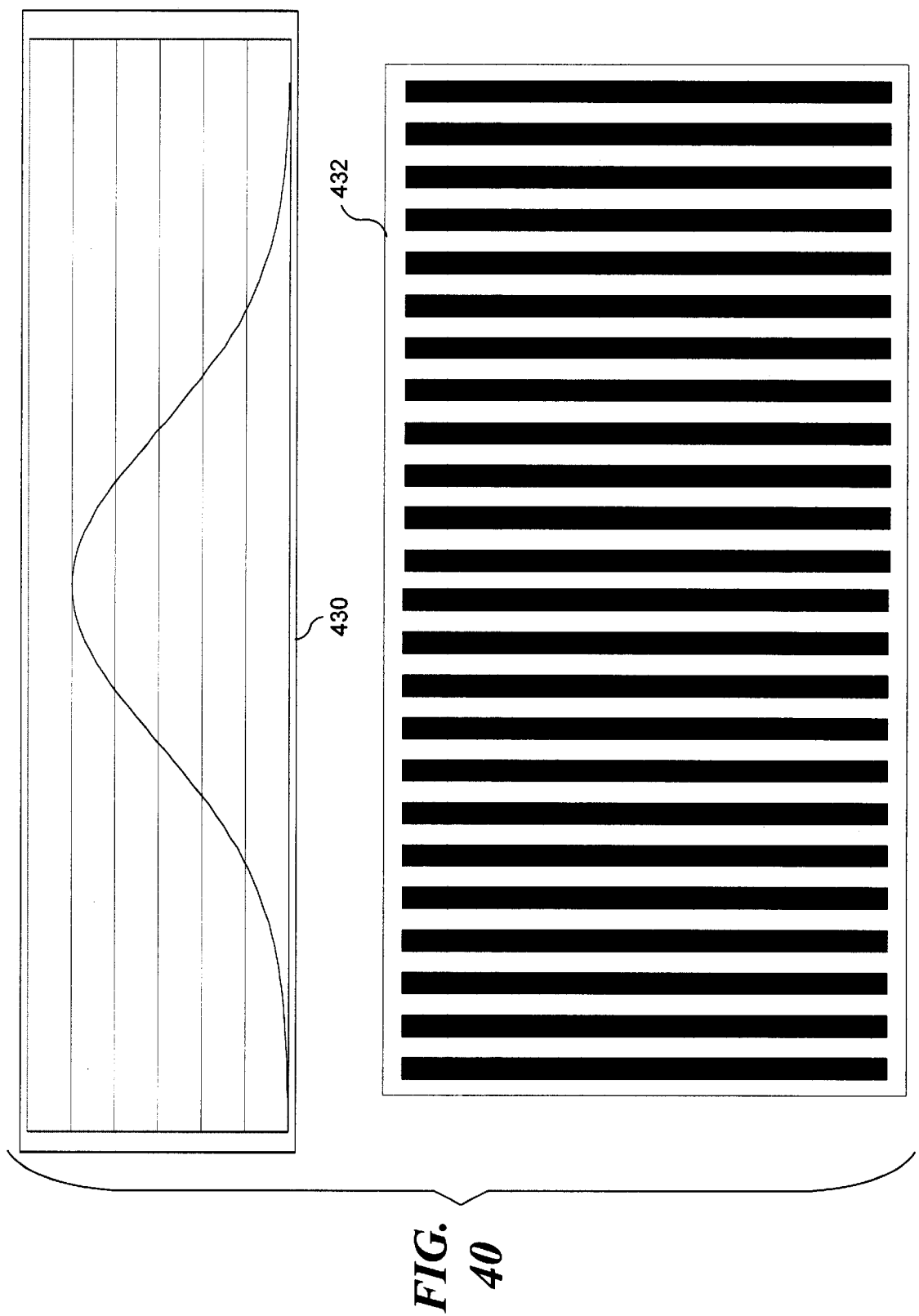
Figure 41:
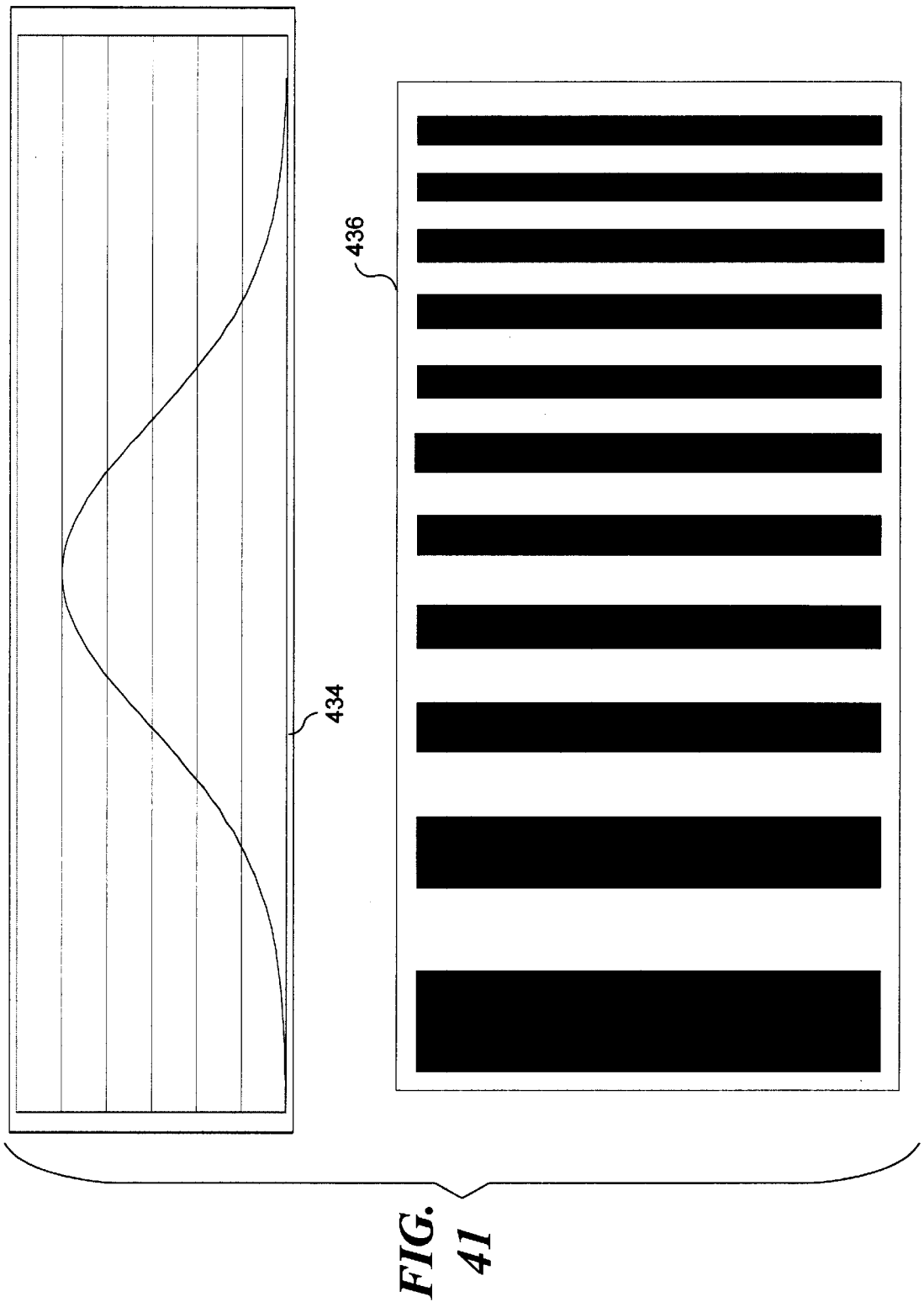
Figure 42:
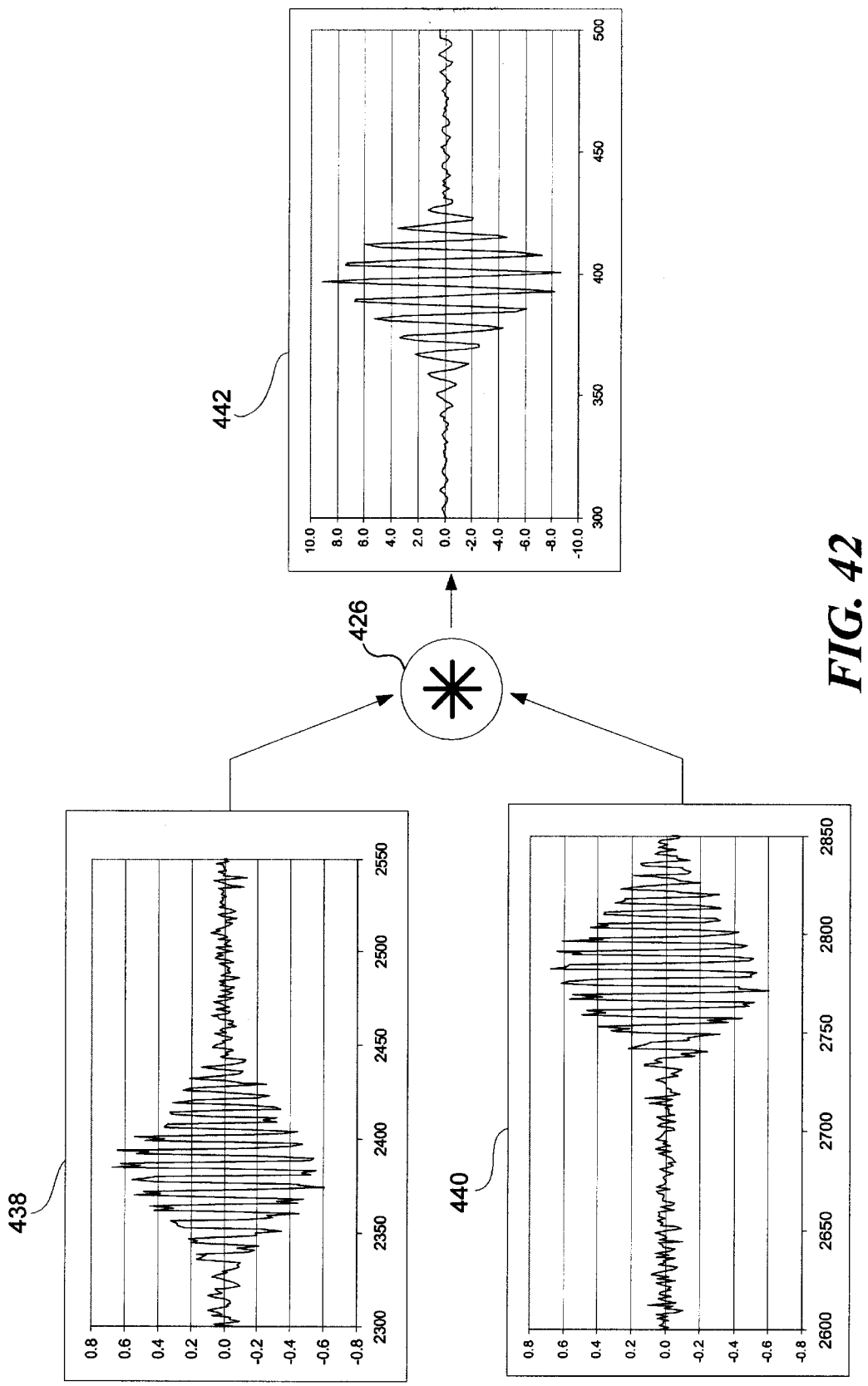
Figure 43:
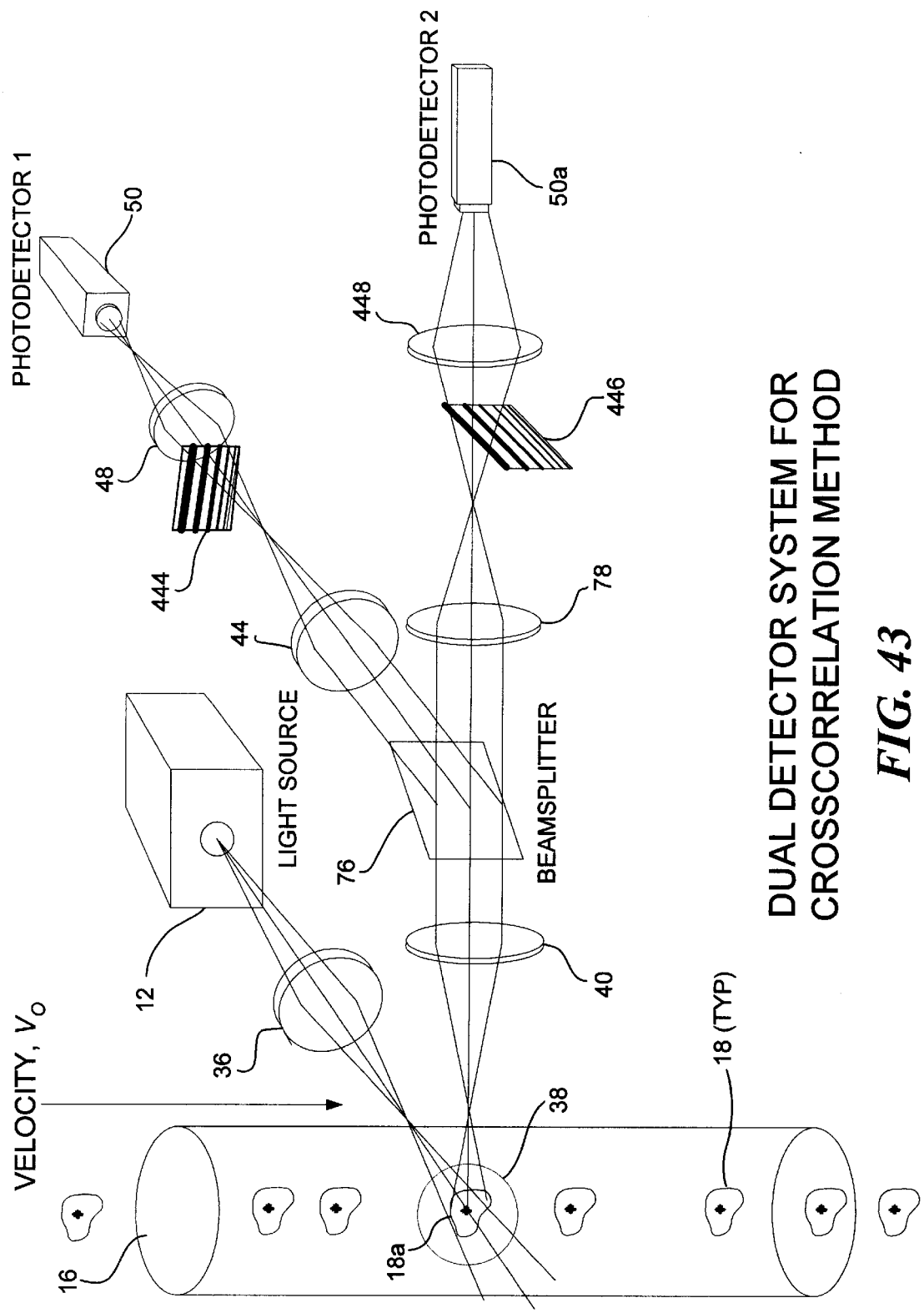
Figure 44:
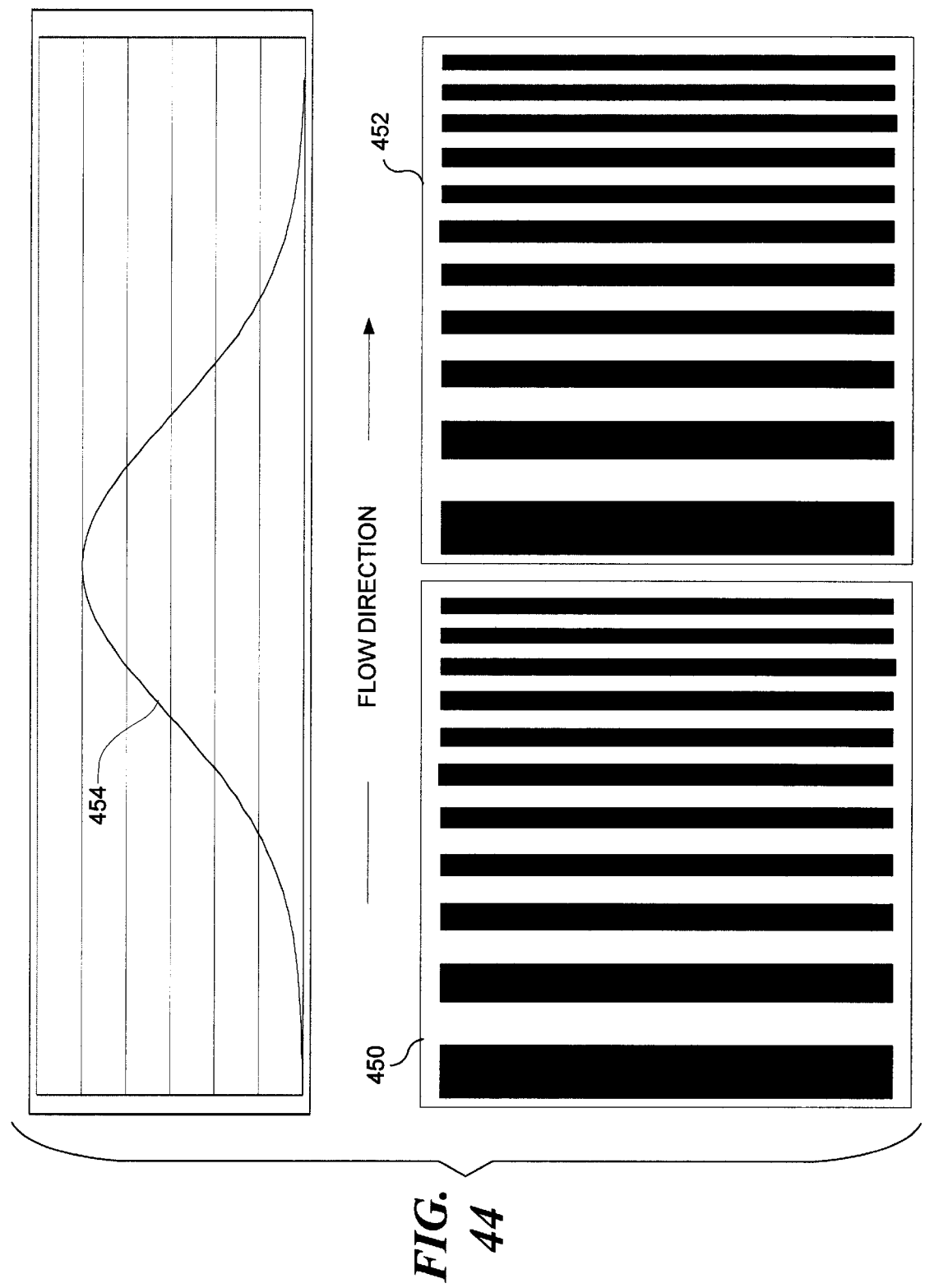
Figure 45:
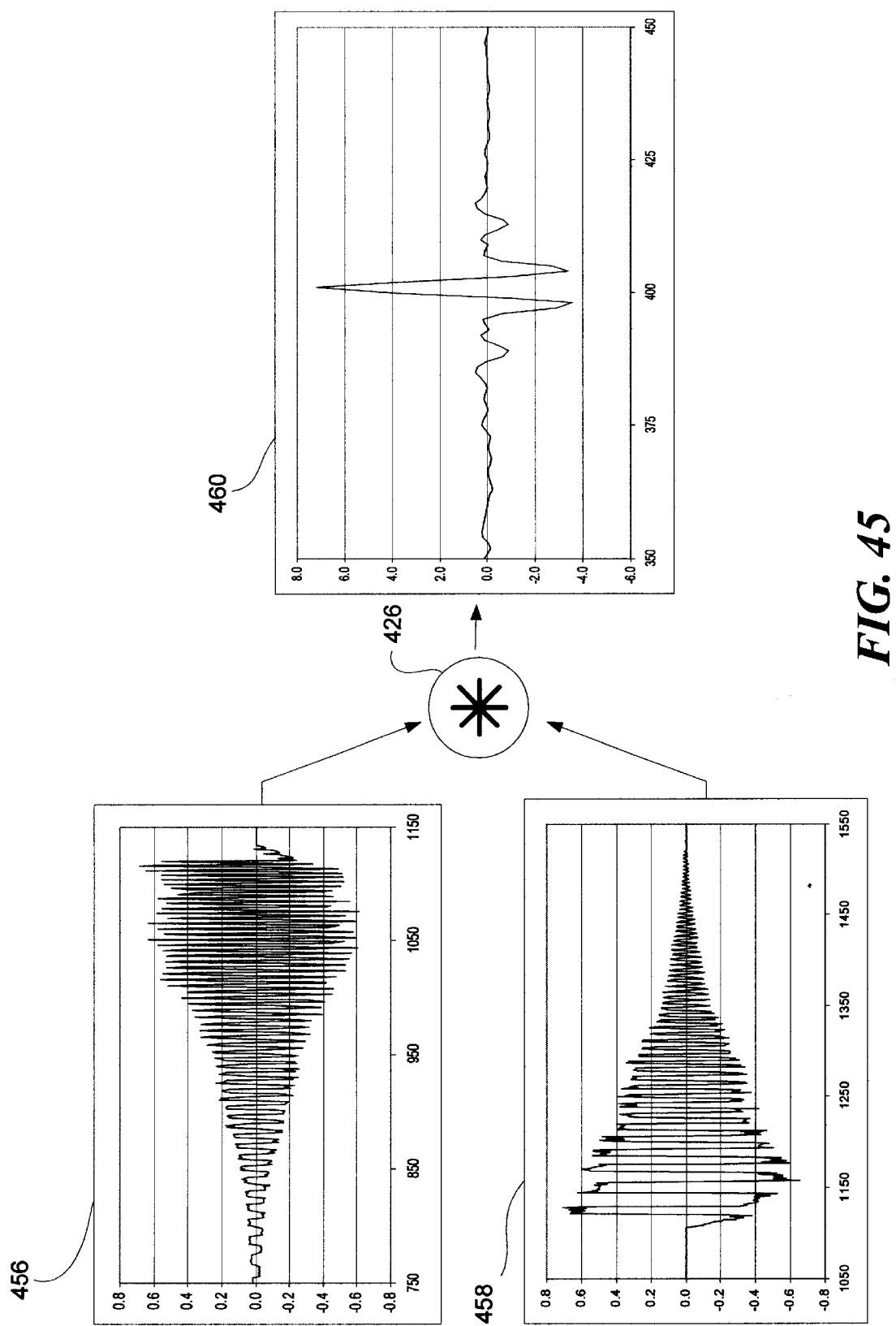
Figure 46:
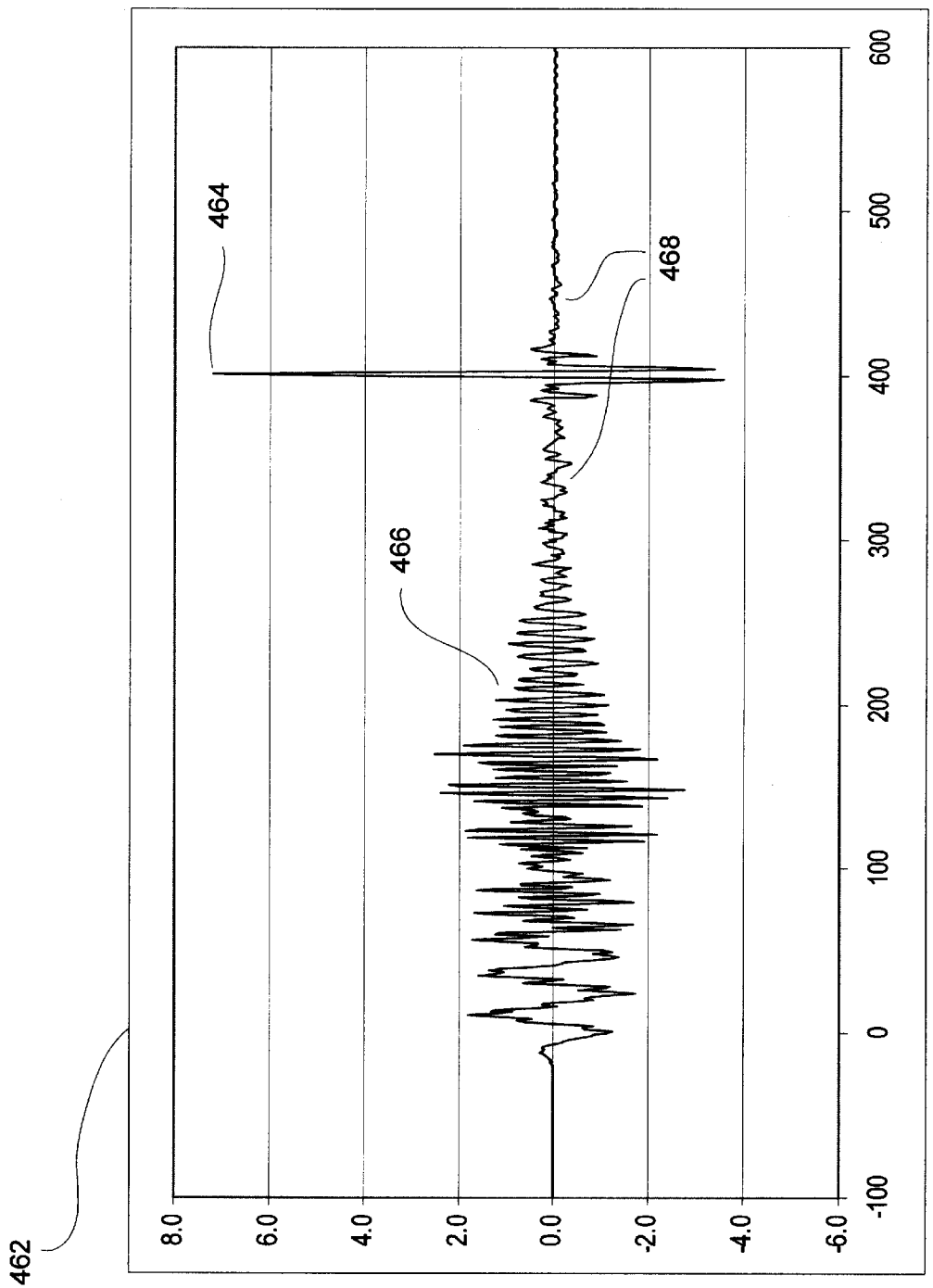
Figure 47:
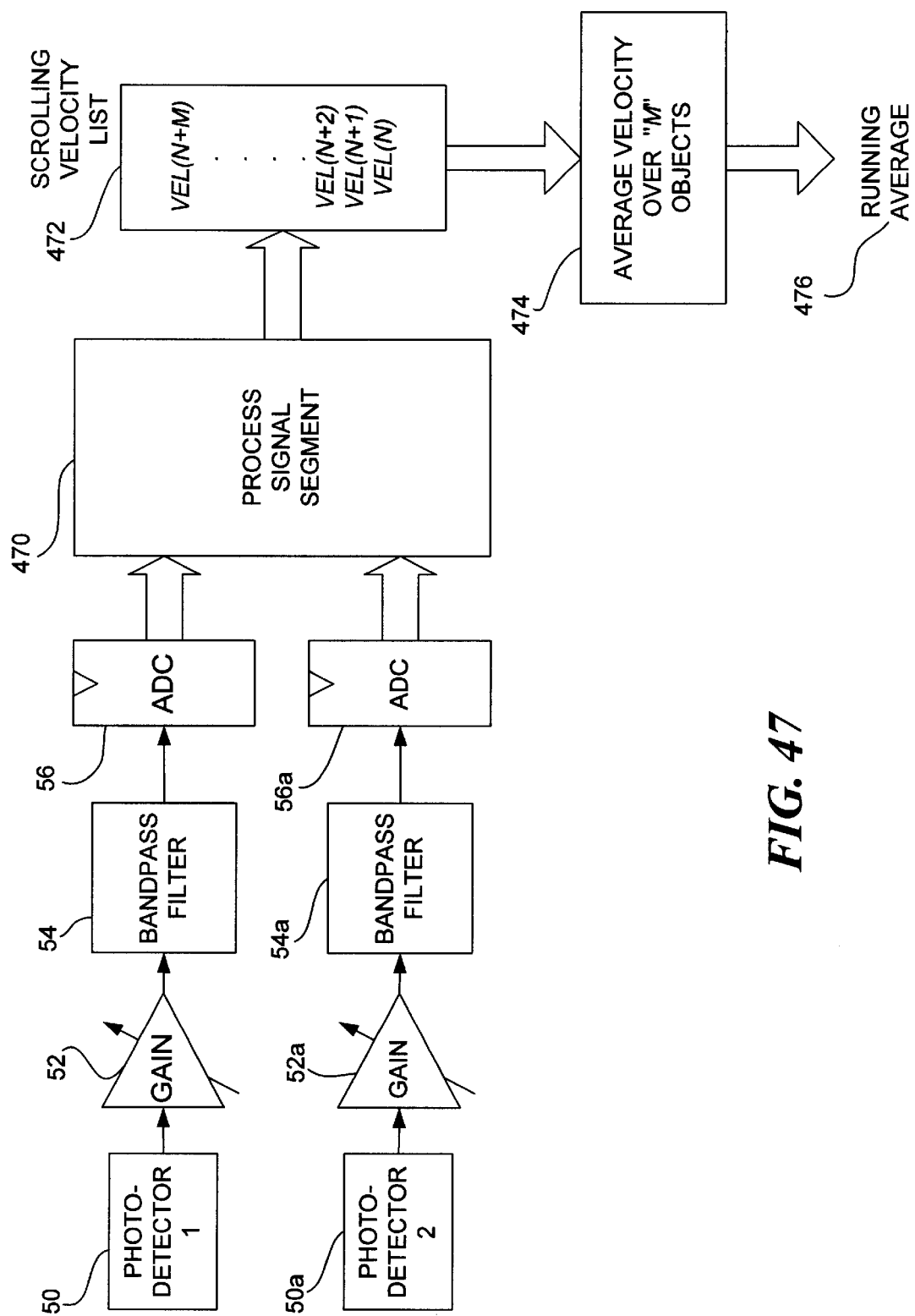
Figure 48:
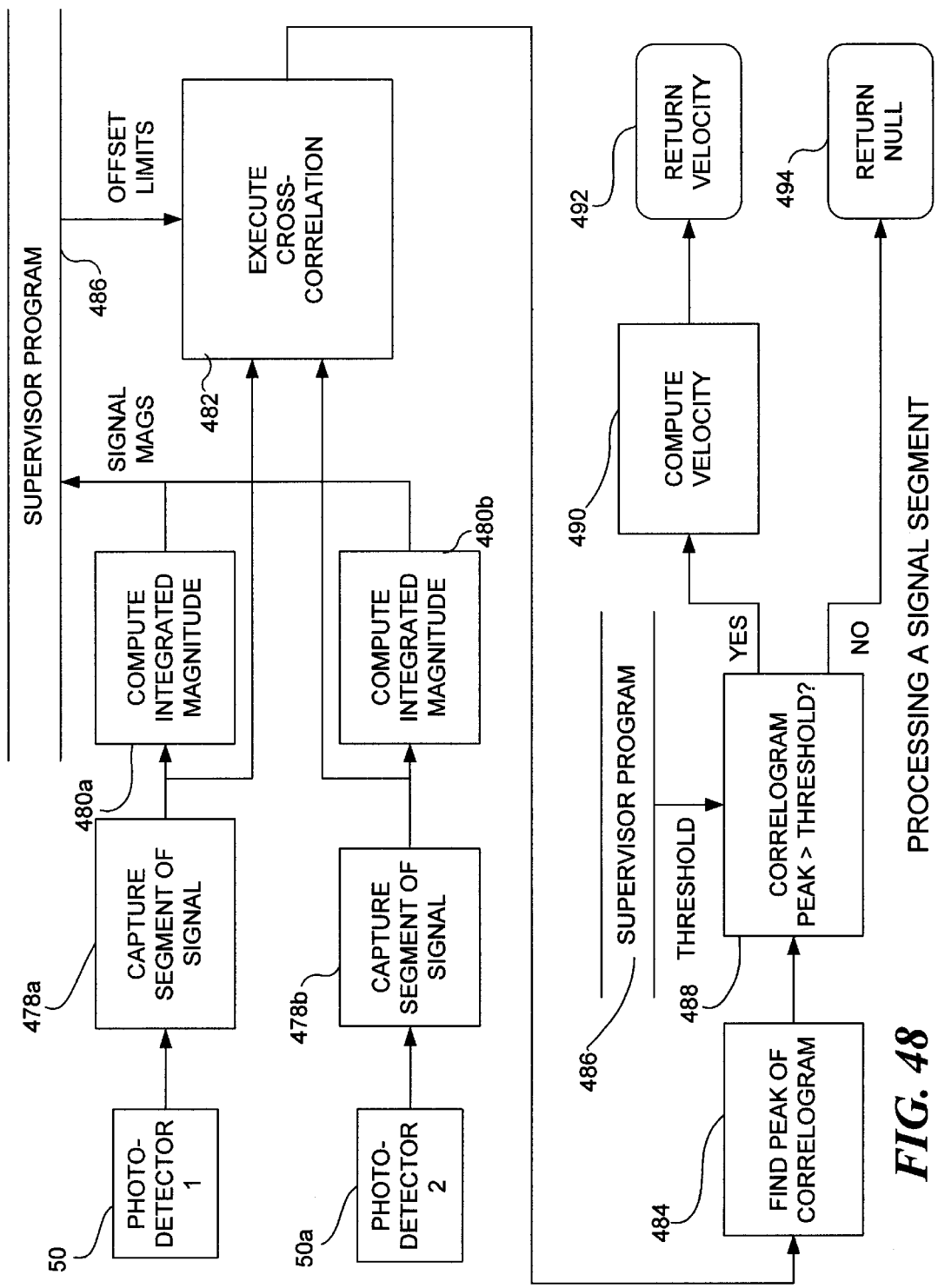
Figure 49:
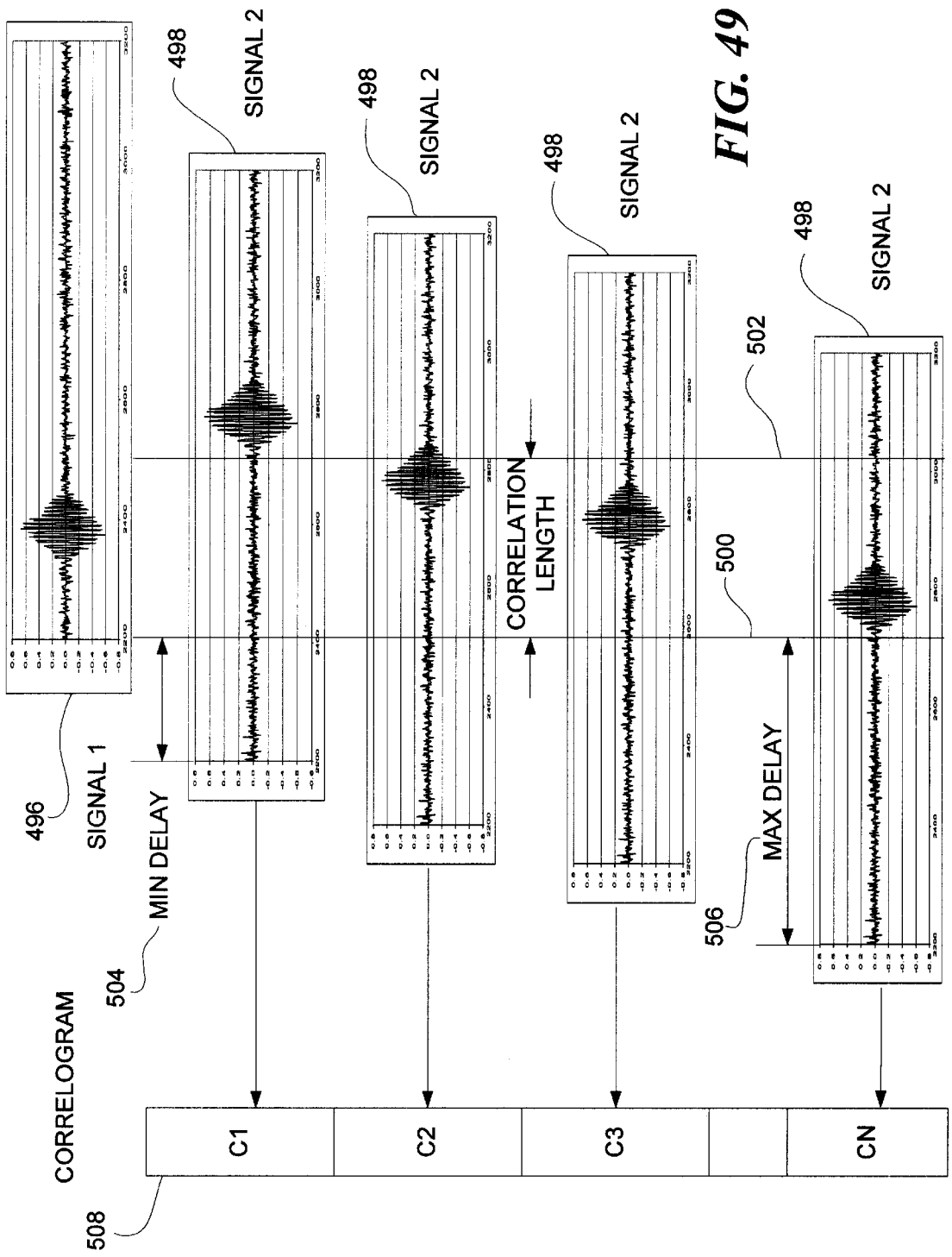
Figure 50:
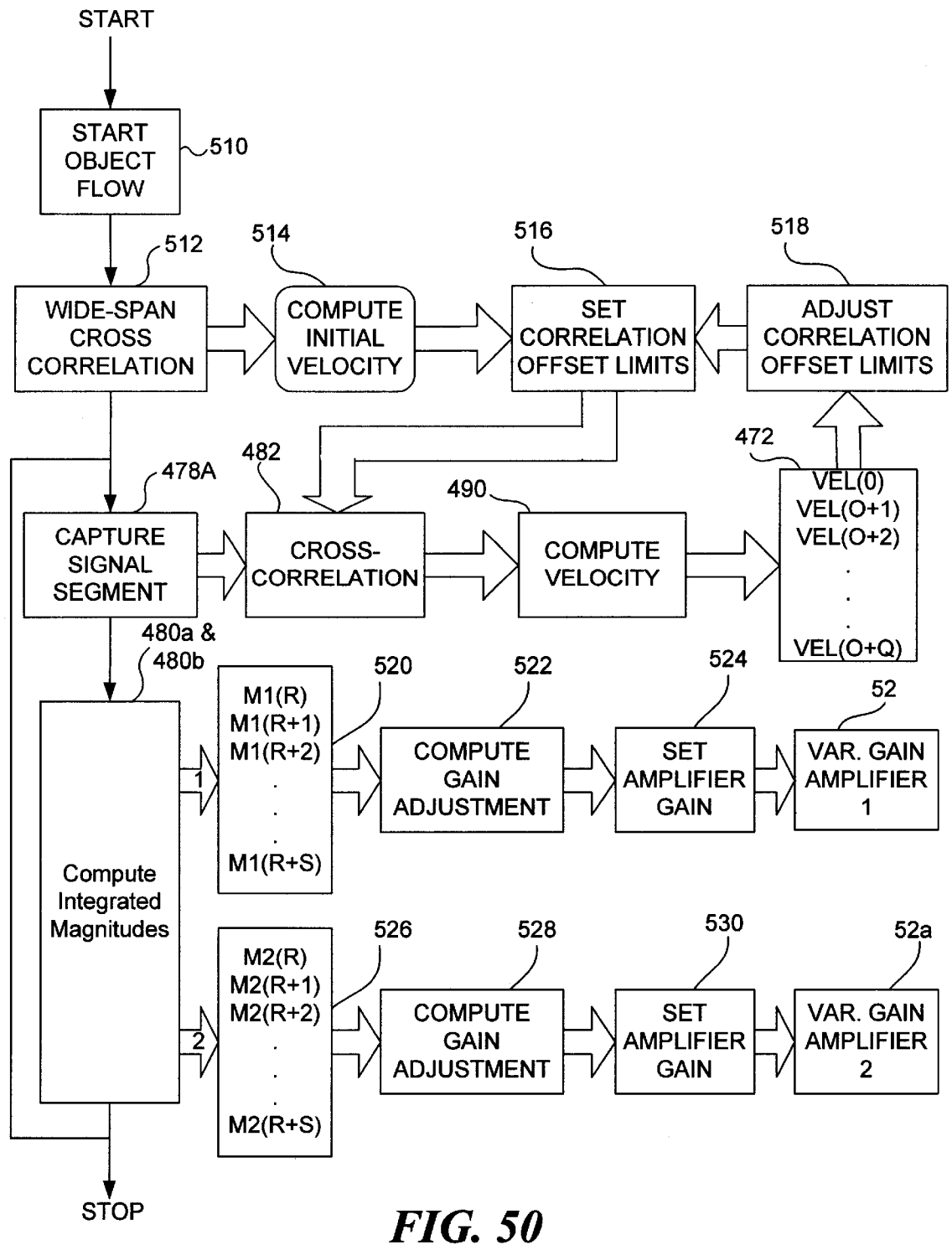

FIG. 26 schematically illustrates a modification of the spectrum of an exemplary photosensor signal by a baseband converter;

FIG. 27 schematically illustrates a modification of the spectrum of the exemplary photosensor signal of FIG. 26 by a baseband converter;

FIG. 28 schematically illustrates an analysis of the magnitude and phase series of the exemplary photosensor signal of FIG. 26 by computations on the I and Q baseband signals;

FIG. 29 schematically illustrates an application of a phase unwrapping algorithm to the phase series of the exemplary photosensor signal of FIG. 26, to provide a monotonic phase series;

FIG. 30 is a block diagram illustrating the steps employed in the phase unwrapping algorithm;

FIG. 31A is a graph showing a magnitude threshold being applied to a signal representing the monotonic phase series of FIG. 29, to reduce the effects of random noise;

FIG. 31B is a graph showing the result of employing the magnitude threshold of FIG. 31A before computing the fractional frequency from the monotonic phase series of FIG. 29;

FIG. 32 is a block diagram of the signal processing and velocity computation steps for the third embodiment of the present invention;

FIG. 33 schematically illustrates a computational modification of the spectrum of I and Q baseband signals to provide upper and lower sideband signals;

FIG. 34 is a block diagram illustrating the steps comprising segmentation and analysis of objects for the third embodiment of the present invention;

FIG. 35A is a graph illustrating the summation of the baseband frequency and the local oscillator frequency;

FIG. 35B is a graph illustrating the conversion of the sum of FIG. 35A to a velocity;

FIG. 36 is a block diagram illustrating the steps employed by a supervisory program for controlling the third embodiment of the present invention;

FIG. 37 is a graph of the sum of the upper sideband power and the lower sideband power for a broad sweep of the local oscillator frequency;

FIG. 38 is a graph showing the transition of power from the upper sideband to the lower sideband for a narrow sweep of the local oscillator;

FIG. 39 schematically illustrates the convolution of two signals generated by a conventional optical grating of uniform pitch;

FIG. 40 schematically illustrates the design of a conventional optical grating and its alignment to the Gaussian profile of the illumination beam;

FIG. 41 schematically illustrates the design of an optical grating with linearly swept pitch and its alignment to the Gaussian profile of the illumination beam;

FIG. 42 schematically illustrates the convolution of two signals generated by an optical grating having a linearly swept pitch;

FIG. 43 is a schematic diagram of a velocity measurement system using stacked gratings of non-uniform pitch, in accord with a fourth embodiment of the present invention;

FIG. 44 schematically illustrates the alignment of images of two gratings of non-uniform pitch relative to the Gaussian beam profile of the illumination beam;

FIG. 45 schematically illustrates the convolution of signals from two photosensors using the stacked non-uniform gratings of the fourth embodiment of the present invention;

FIG. 46 is a graph of an expanded correlogram for the signals generated by the stacked non-uniform gratings;

FIG. 47 is a block diagram broadly illustrating the steps required for signal processing and velocity computation in accord with the fourth embodiment of the present invention;

FIG. 48 is a block diagram illustrating detailed steps for the processing of a signal segment of the fourth embodiment of the present invention;

FIG. 49 schematically illustrates the concept of the convolution of a first signal by a second similar but delayed signal; and FIG. 50 is a block diagram illustrating the logical steps implemented by a supervisory program for controlling the fourth embodiment of the present invention.

DESCRIPTION OF THE PREFERRED EMBODIMENT

Overview of the Present Invention

In the present invention, moving objects are illuminated and light from the objects is imaged onto a detector after passing though an optical grating. The optical grating comprises a plurality of transparent and opaque bars that modulate the light received from the object, producing modulated light having a frequency of modulation that corresponds to the velocity of the object from which the light was received. Preferably the optical magnification and the ruling pitch of the optical grating are chosen such that the bars are approximately the size of the objects being illuminated. Thus, the light collected from cells or other objects is alternately blocked and transmitted through the ruling of the optical grating as the object traverses the interrogation region, i.e., the FOV. The modulated light is directed toward a light sensitive detector, producing a signal that can be analyzed by a processor to determine the velocity of the object.

The present invention has been developed as four distinct preferred embodiments. First and second embodiments employ a first optical grating and a frequency domain velocity measurement based signal processing technique. A third embodiment also employs the first optical grating, but uses a time domain velocity measurement (TDVM) based signal processing technique. A fourth embodiment employs the first and also includes a second optical grating to determine velocity using the time domain based signal processing technique. The differences in the first and second embodiments are that the first embodiment is specifically directed to analyzing objects that are deposited on a support that is moved through a FOV, while the second embodiment applies the same general processing technique to determine the velocity of objects that are entrained in a fluid flow through the FOV. Details of these specific embodiments are provided below, after a brief discussion of the concepts generally applicable to all of the embodiments.

Figure 1:
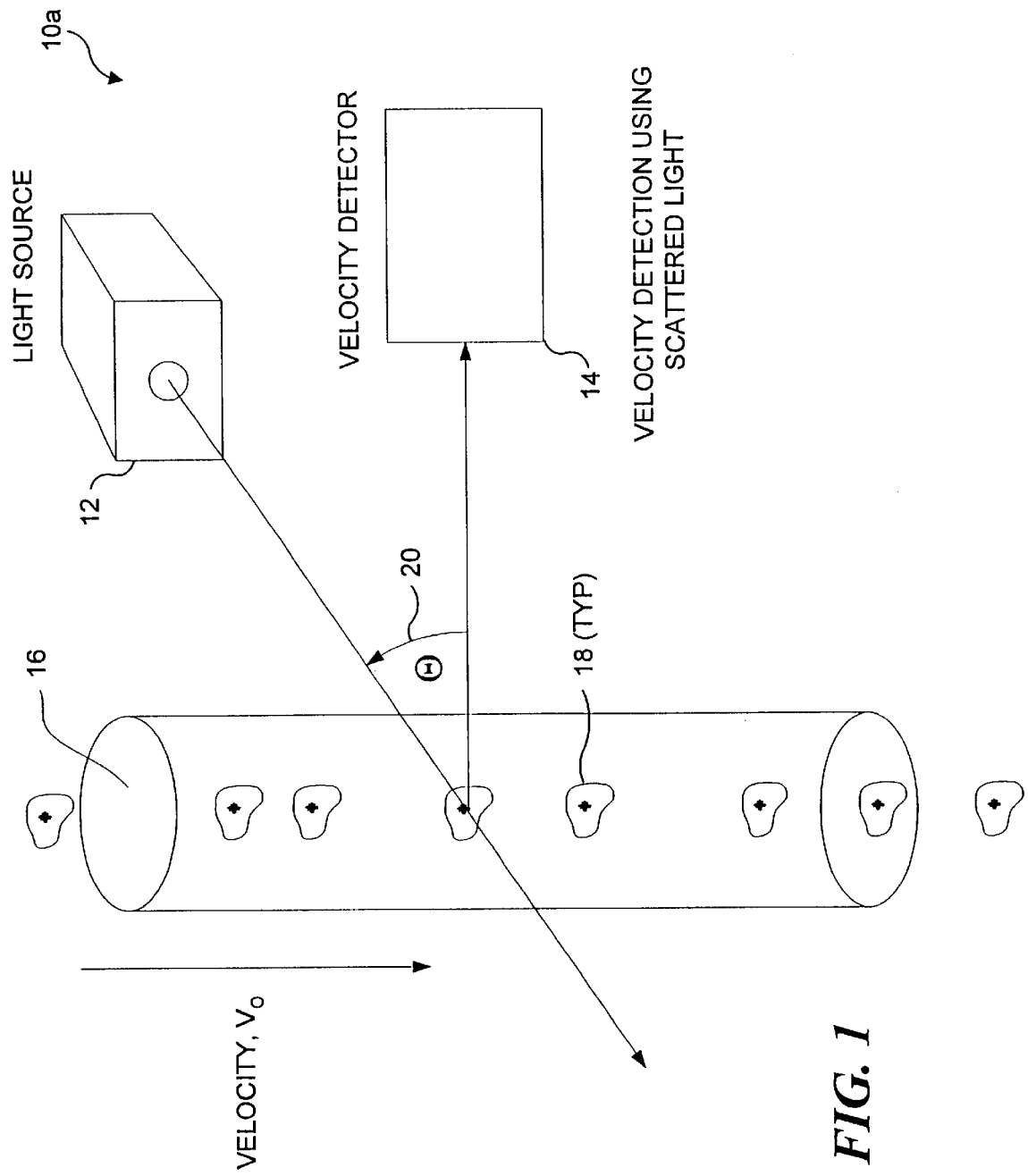
FIG. 1 is a schematic diagram of a system for measuring the velocity of objects in a flow stream by detecting light scattered by the objects.
Figure 2:
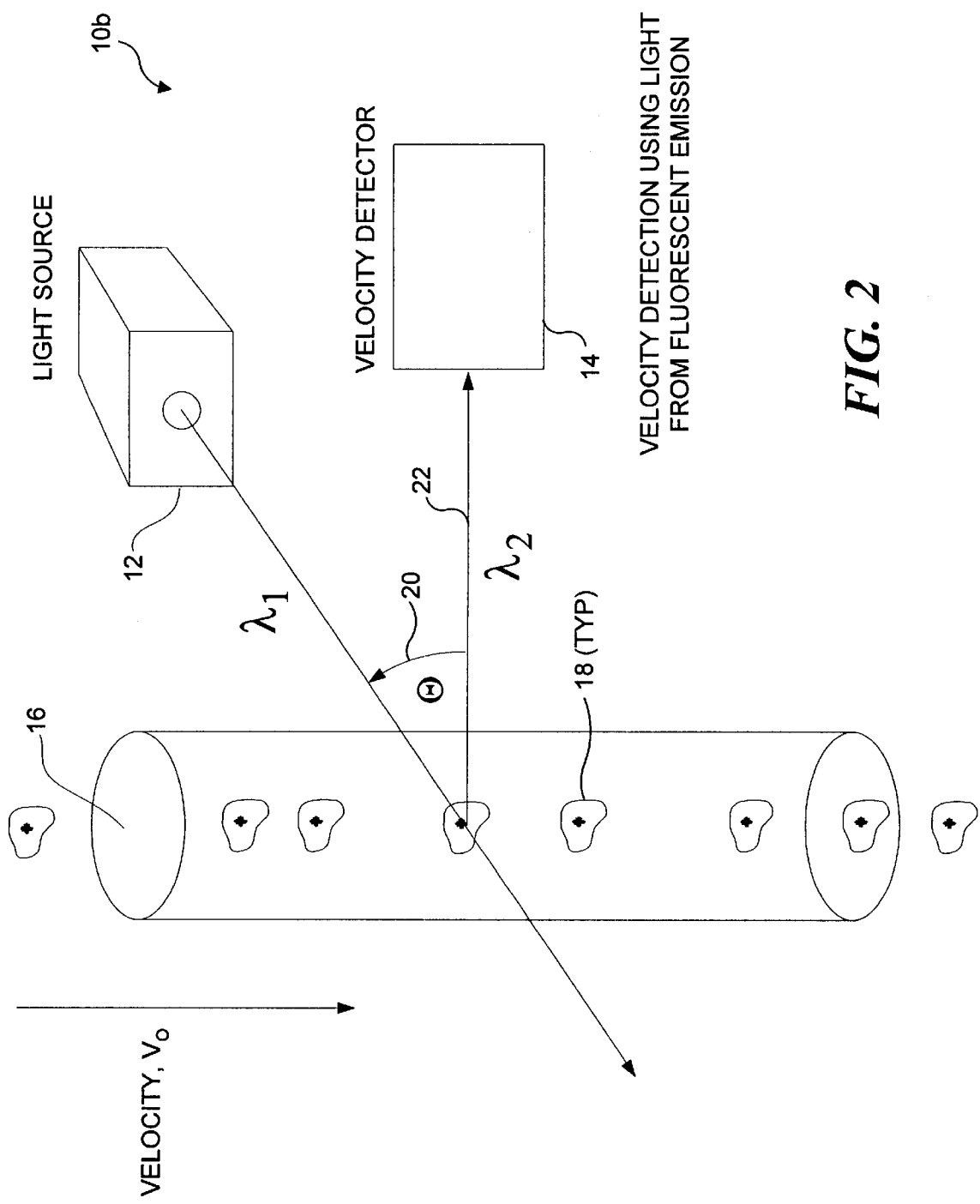
FIG. 2 is a schematic diagram of a system for measuring the velocity of objects in a flow stream by detecting light emitted by fluorescence by the objects.
Figure 3:
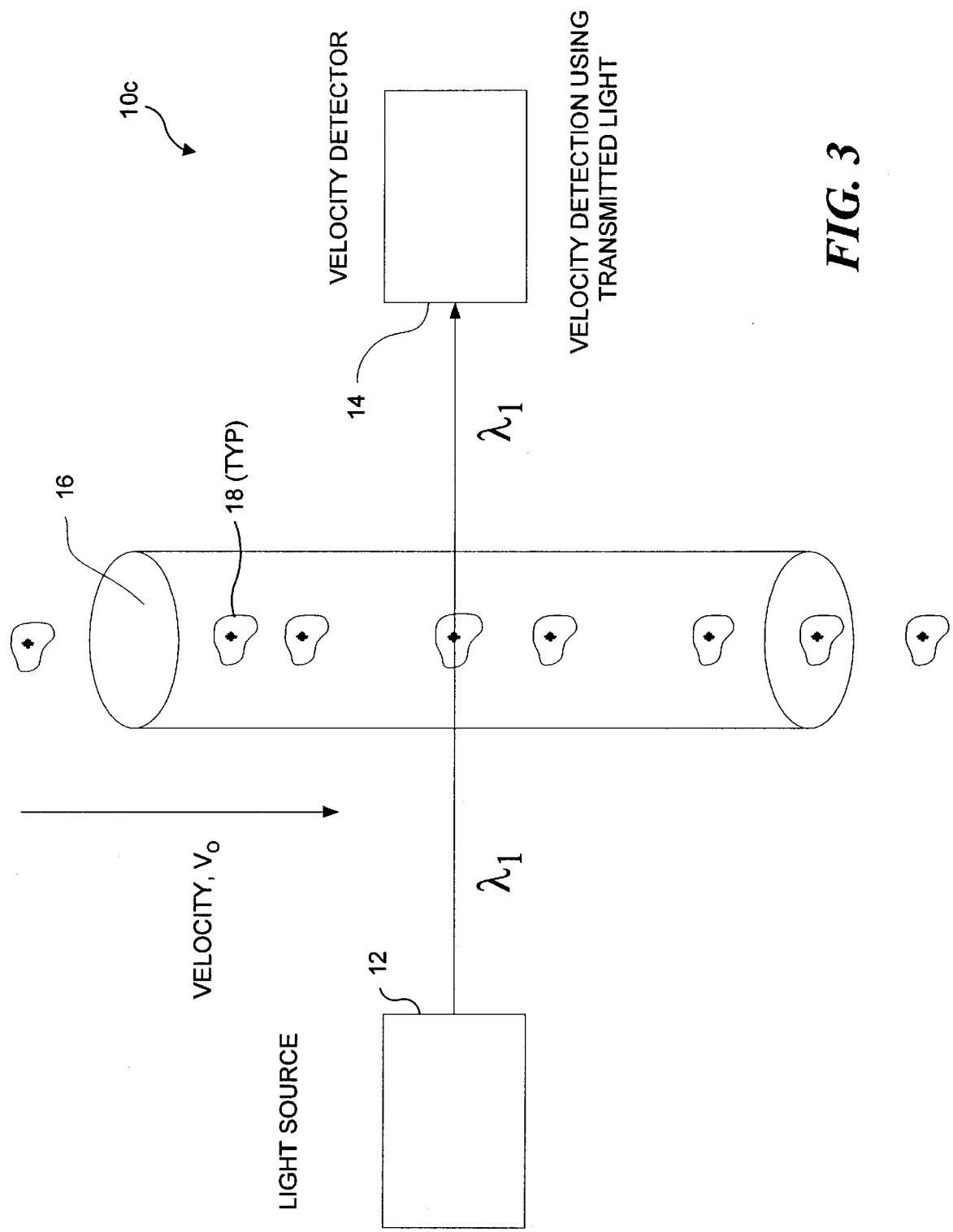
FIG. 3 is a schematic diagram of a system for measuring the velocity of objects in a flow stream by detecting the absorption of light by the objects.

The present invention can be used with any of the various illumination and light collection configurations illustrated in FIGS. 1, 2, and 3. However, those configurations should not be considered limiting on the scope of the invention, and are provided merely as exemplary configurations. Each Figure shows a light source, objects in motion (preferably objects entrained in a flow of fluid) illuminated by the light source, and a velocity detector for receiving light from the objects. The light source may be a laser, a light emitting diode, a filament lamp, or a gas discharge arc lamp, and the system may include optical conditioning elements such as lenses, apertures, and filters that are employed to deliver one or more desired wavelengths of light to the object with an intensity required for detection of the velocity (and optionally, one or more other characteristics of the object). The velocity detector includes a light sensitive detector (not separately shown in these figures) comprising, for example, a photomultiplier tube or a solid-state photodetector, and one or more other optical conditioning elements such as a lens, aperture, and/or filter, to deliver the modulated light to the light sensitive detector (also not separately shown in these figures).

FIG. 1 illustrates the configuration of a system 10a that employs light scattered by objects 18 traveling through a flow tube 16. An angle 20 (designated as angle θ) between the beam axis of an illuminator 12 and an acceptance axis of a velocity detector 14 may be adjusted so that light scattered from the objects is delivered to the velocity detector, for a particular scatter angle. The intensity profile of the scattered light is a function of the ratio of the size of the scattering elements to the wavelength of the incident light. A relatively large number of scattering elements may be present in/on the object, and angle θ may be adjusted for the detection of scattered light from elements within a desired size range for the elements.

FIG. 2 illustrates the configuration of a system 10b that uses light emitted by objects 18 traveling in flow tube 16, in response to the absorption by the objects of light from illuminator 12. In this case, the detection axis will typically be orthogonal to the illumination axis in order to minimize the amount of incident light reaching velocity detector 14. Typically, a filter or a set of filters (not separately shown) will be included in the velocity detector to deliver to the light sensitive detector only a narrow band of wavelengths of the light traveling along a detection path 22 corresponding, for example, to the wavelengths emitted by the fluorescent or phosphorescent molecules in the object, so that light in the wavelength(s) provided by the illuminator 12 is substantially eliminated.

FIG. 3 illustrates the configuration of a system 10c utilizing light from illuminator 12 that continues to propagate towards velocity detector 14 along the axis of illumination; this light is modified by objects 18 traveling in flow tube 16 by absorption, diffraction, or refraction. Note that system 10c is not well adapted for the detection of light emitted by fluorescence or phosphorescence, due to the high intensity of light emitted by illuminator 12 relative to the intensity of light emitted from objects 18, and that both types of light follow the same path to velocity detector 14. Modification of the light by the objects caused by absorption can be detected by measuring the intensity of the light incident on the velocity detector. A system of lenses may be used to restrict the origin of the collected light to a desired field in the path of the stream of objects. Modification of the light by the objects caused by diffraction or refraction may be detected through the use of a phase contrast method, in which only light subjected to phase modification by an object is visible, any unmodified light having been canceled by interference with a reference beam (not separately shown).

In each of the above-noted configurations, the light received by the velocity detector is modified by objects passing through a FOV. Because this FOV is bounded by the profile of the illumination field and by the acceptance window of the velocity detector, it would seem to be possible to estimate object velocity from the time it takes for the object to pass through the FOV. However, the FOV is bounded by gradients rather than distinct edges, and it will likely be impractical to maintain the dimensions of the FOV with a high degree of accuracy. This limitation is particularly true when the objects being illuminated or emitting the light that is detected are small in size, such as biological cells.

Figure 4:
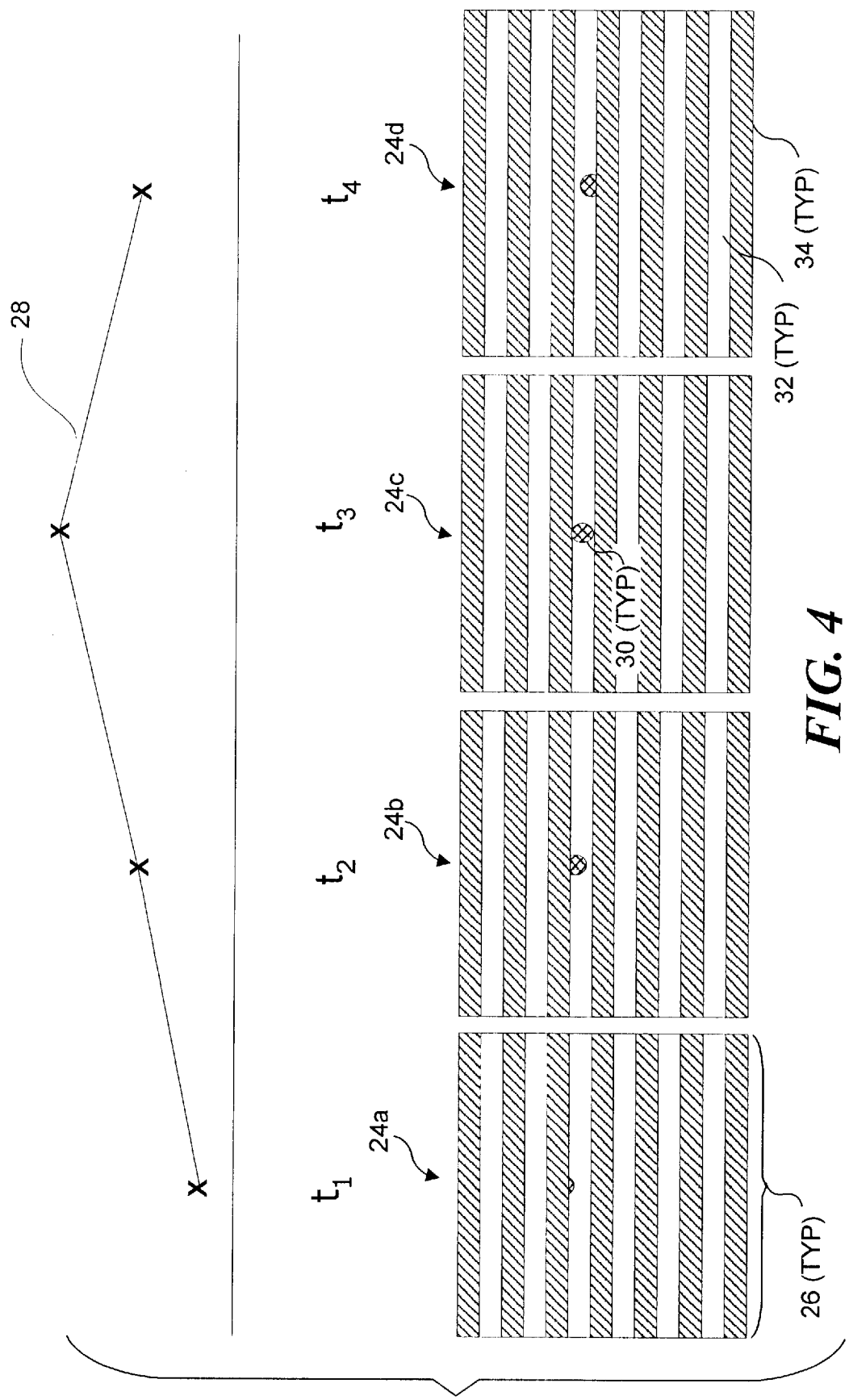
FIG. 4 is a schematic illustration of the concept of building a signal from the passage of the image of a bright object across a grating.

Placing an optical grating in the path of light incident on the velocity detector establishes a highly precise distance scale for measuring object velocity. The optical grating concept is illustrated in FIG. 4. This figure shows the positive contrast of the object relative to a background, which occurs if the light being detected is emitted from the object by fluorescence or phosphorescence, or is light that is scattered by the object. Preferably, in the optical grating shown, the opaque and transparent bar widths are substantially equal and substantially equal to an average diameter of the objects whose velocity is to be measured. This matching of the optical grating to the object size increases the light modulation amplitude, but it should be noted that the optical grating will provide the desired modulating function over a wide range of object size relative to the optical grating pitch.

FIG. 4 includes shows four snapshots 24a–24d of an optical grating 26, at equally spaced sample times, $t_1$–$t_4$, and a signal amplitude 28 incident on the light sensitive detector at those times. Note that each grating 26 includes alternating opaque zones 34 and transparent zones 32 of uniform pitch. The passage of the light emitting object 30 across one of the transparent zones 32 in the optical grating causes the amplitude to increase as the exposed area of the object increases, and then to decrease as the object moves behind one of opaque zones 34. In the ideal case, only direct light from objects would reach the detector. Typically, however, some scattered light or light from stray fluorescence will continuously pass through the transparent zones, creating a constant bias or offset in the light sensitive detector output signal.

Figure 5:
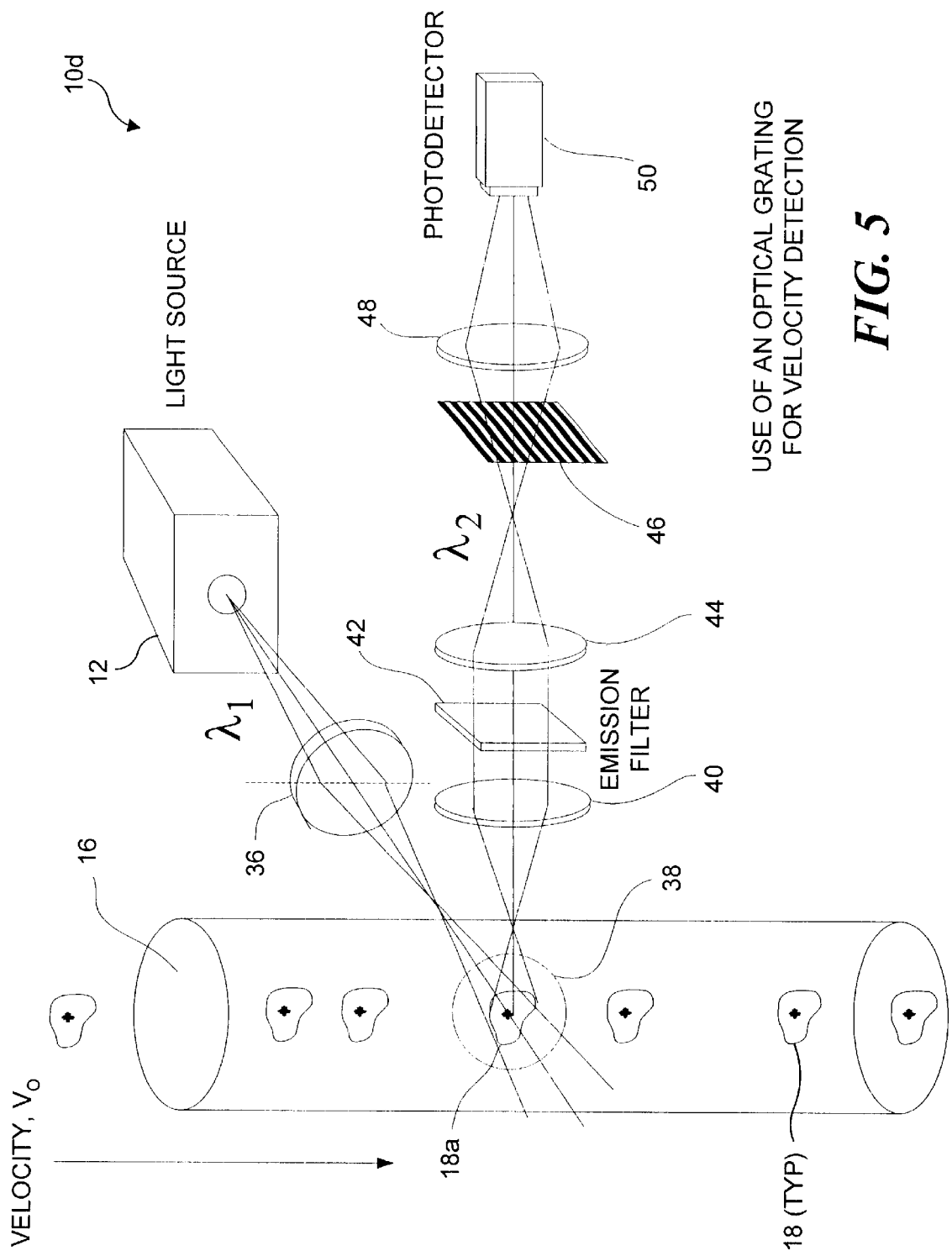
FIG. 5 is a schematic diagram showing the integration of an optical grating into a flow velocity measurement system.

FIG. 5 shows an optical system 10d that illustrates how the optical grating-based detection system might be implemented for the case in which the objects emit photons through the process of fluorescence. A lens 36 creates a focused illumination field at a wavelength $\lambda_1$ in a FOV 38. Fluorescence in an object 18a caused by this illumination results in photons being emitted by the object collected by lens 40 on the detector axis. An emission filter 42 is used to reject light at wavelengths other than $\lambda_2$. Lens 40 and a lens 44 create a focused image of the object on an optical grating 46. It would be possible to generate a conjugate image of the object and the optical grating at a camera, in which case the camera would produce well-focused images of objects passing across the sharp boundaries of the optical grating, as shown in FIG. 4. However, accurate periodic sampling of the modulated light produced as light from the moving object passes through the optical grating is sufficient for making the velocity measurement, and the extra complications of capturing and analyzing images is eliminated. In the preferred approach, a lens 48 is used to collect the light transmitted by the optical grating and deliver it to a photodetector 50. It should be noted that other optical elements, such as concave mirrors, can be used in place of the lenses discussed above.

In a preferred application, objects 18 are preferably biological cells entrained in a fluid. The fluid is confined to a narrow column passing through FOV 38 of the optical system by hydrodynamic focusing with a flow sheath. The cells are kept within the depth of field of lenses 40 and 44, assuring good focusing and, therefore, a modulation amplitude sufficient for the determination of the velocity of the object.

Light from a single object moving through the FOV at a uniform velocity will, when modulated by the optical grating, have a frequency directly proportional to the velocity, as defined by the following relation:

$$f = \frac{v}{s}$$

where:
 f=frequency (Hz)
 s=grating pitch (microns)
 v=velocity (microns/sec).

The amplitude of the signal generated at the photodetector by light from a single object will follow the contour of the illumination field. If the illumination field profile has a Gaussian shape, for example, the signal is described by the equation:

$$x(t) = A_0 e^{-(t-t_{pk})2/\tau 2} e^{j2\pi f(t-t_0)} + A_L$$

where:
 $A_0$=peak amplitude
 $A_L$=leakage amplitude from stray light
 $t_{pk}$=time of arrival at peak of illumination field
 $\tau$=envelope decay constant
 $t_0$=time of arrival at edge of grating image.

Figure 6:
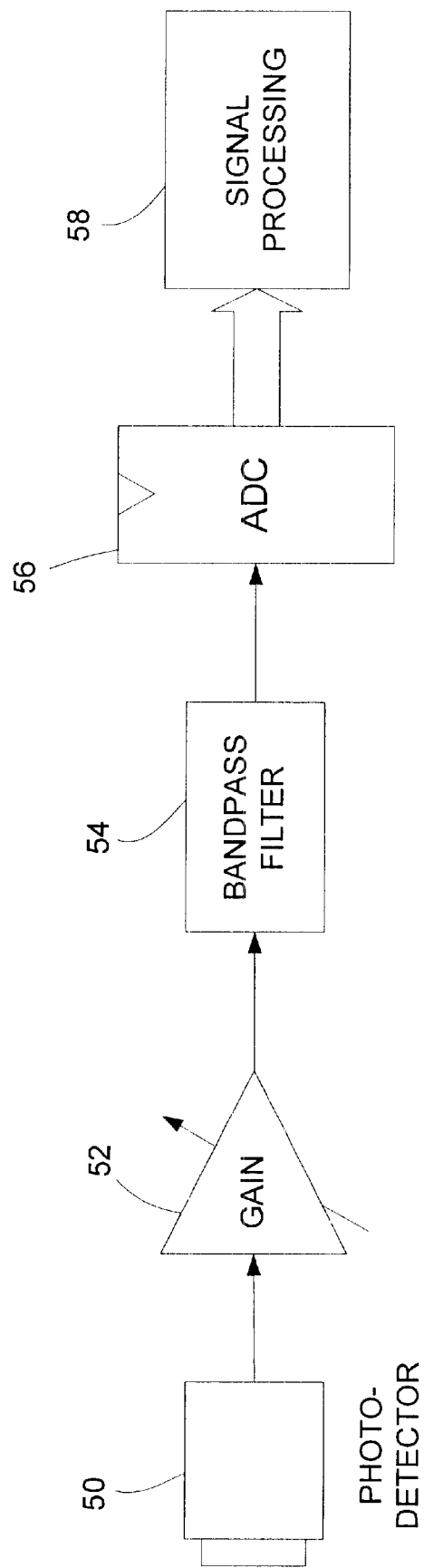
FIG. 6 is a block diagram illustrating the stages of processing the signal from a light sensitive detector for the purpose of object velocity measurement.
Figure 7A:
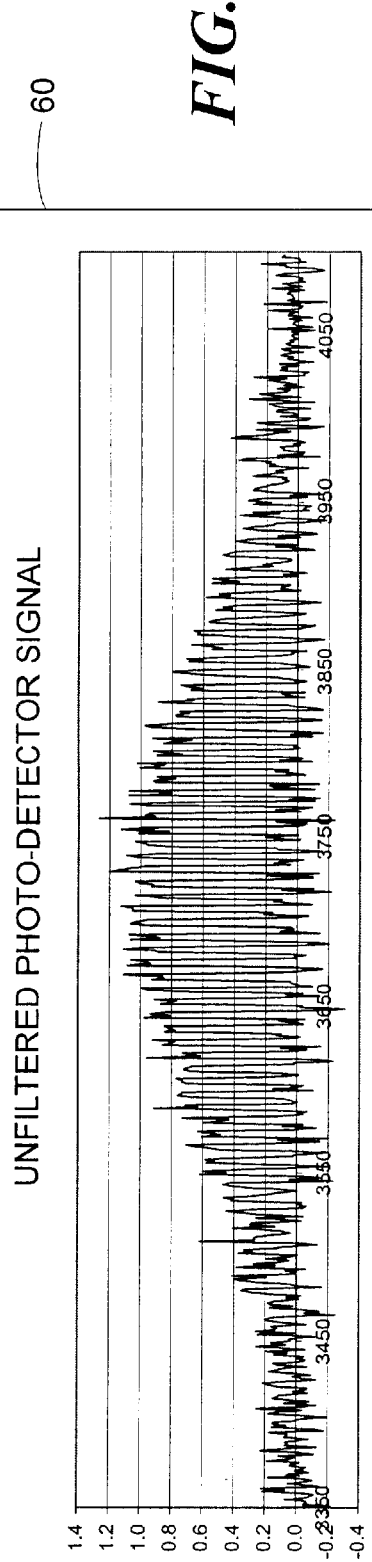
FIG. 7A illustrates a graph of a typical photodetector signal before bandpass filtering.
Figure 7B:
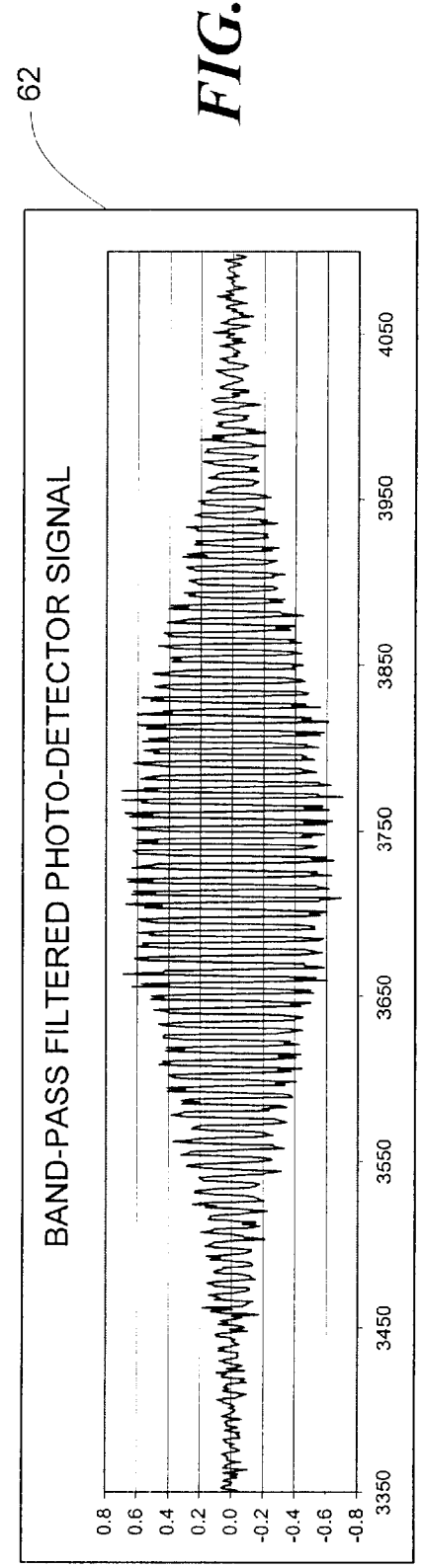
FIG. 7B illustrates a graph of a typical photodetector after bandpass filtering.

FIG. 6 shows a typical embodiment of a photodetector signal conditioning and capture system. A central feature of this system is the use of a bandpass filter 54 to filter the signal from the photodetector 50 (after the signal is amplified). The purpose of this bandpass filter is to reject a direct current (DC) component, $A_L$, and to eliminate any frequencies above a Nyquist limit, $f_{samp}/2$, of an analog-to-digital converter (ADC) 56, where $f_{samp}$ is the highest light modulation frequency of interest. A variable-gain amplifier 52 is used to adjust the amplitude of the signal to match the dynamic range of ADC 56. The digitized signal is delivered to a digital signal processor 58 for analysis. Digital signal processor 58 can comprise a programmed computing device (e.g., a microprocessor and memory in which machine instructions are stored that cause the microprocessor to appropriately process the signal), or an application specific integrated circuit (ASIC) chip that carries out the processing, or a digital oscilloscope that includes such signal processing capability. FIG. 7A shows an exemplary unfiltered photodetector signal 60 generated by light from a single object passing through the optical grating field, while FIG. 7B shows an exemplary filtered photodetector signal 62, after application of bandpass filter 54 (see FIG. 6) to the signal.

As noted above, the present invention includes four distinct preferred embodiments. Those four preferred embodiments employ three different techniques for analyzing the signal from the photodetector, to deliver accurate velocity estimates for the objects. The different signal processing methods are described in detail below.

As noted above, one preferred use of the velocity measurement in the present invention is to provide timing signals to optical systems that determine characteristics of small moving objects, such as a flow cytometer. In non-imaging photomultiplier tube (PMF) instruments commonly known as flow cytometers, estimates of flow velocity are used for correcting measurements that depend on signal integration time and to accurately delay the sorting of a cell after its analysis. The optical grating-based velocity detection methods can be used to improve the accuracy and reliability of such flow cytometric measurements and the purity of sorted cell samples by providing a more accurate flow velocity estimate.

The flow imaging systems disclosed in commonly assigned U.S. Pat. No. 6,249,341, issued on Jun. 19, 2001, and entitled IMAGING AND ANALYZING PARAMETERS OF SMALL MOVING OBJECTS SUCH AS CELLS, as well as in commonly assigned U.S. Pat. No. 6,211,955, issued on Apr. 3, 2001, also entitled IMAGING AND ANALYZING PARAMETERS OF SMALL MOVING OBJECTS SUCH AS CELLS, demand very accurate measurements of flow velocity for clocking the TDI detector. The transfer of charge from one row to the next in the TDI detector must be synchronized with the passage of objects through the flow cell. Note that the specification and drawings of each of these two patents have been specifically incorporated herein by reference.

Figure 8:
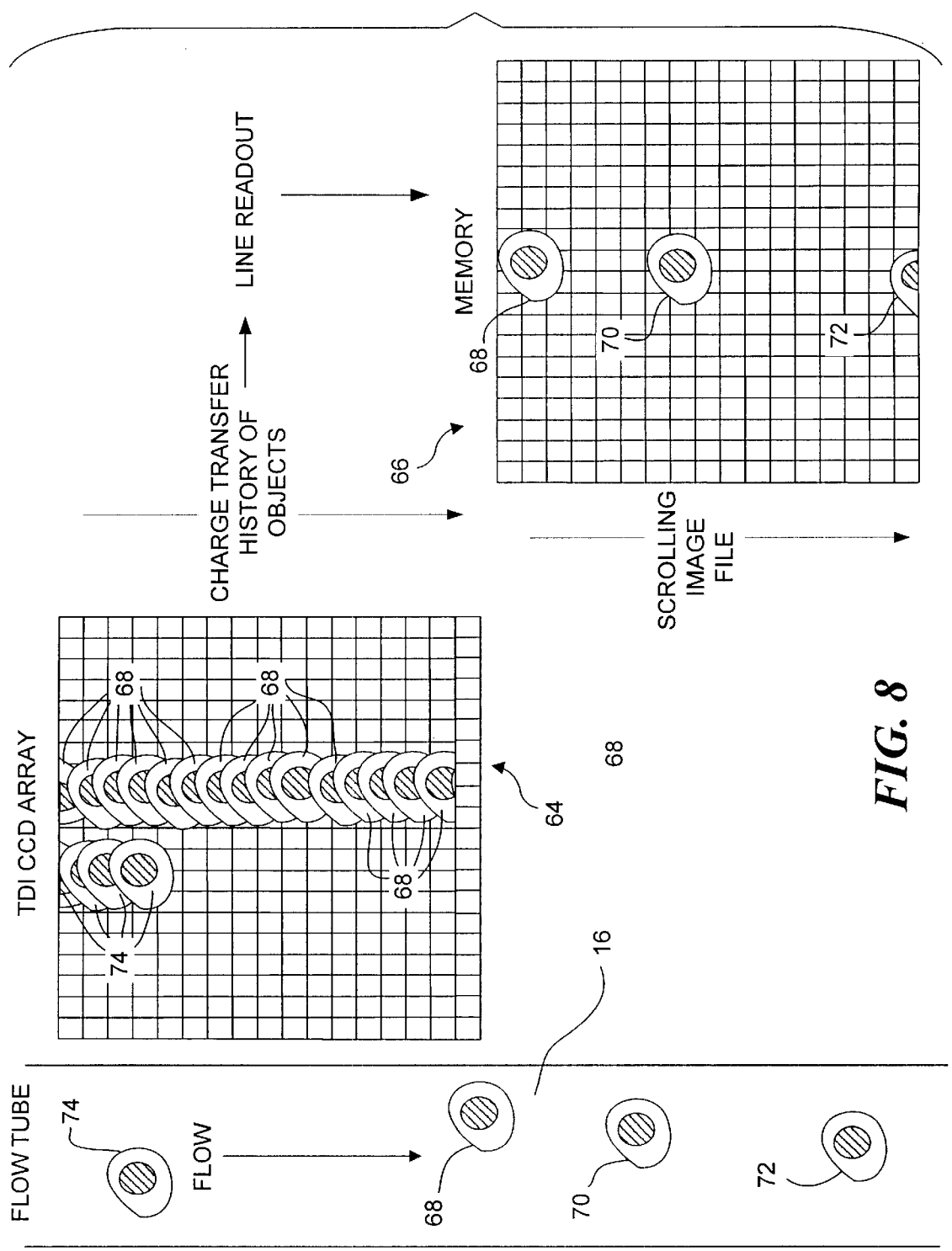
FIG. 8 is a schematic representation illustrating the operation of a TDI detector.

The theory of operation of a TDI detector, such as those employed in the above-noted patent references is shown in FIG. 8. As objects travel through flow tube 16 and pass through the volume imaged by the TDI detector, their images travel across the face of the TDI detector. The TDI detector comprises a charge coupled device (CCD) array 64, which is specially designed to allow charge to be transferred on each clock cycle in a row-by-row format, so that a given line of charge remains locked to or synchronized with a line in the image. The row of charge is clocked out of the array into a memory 66 when it reaches the bottom of the array. The intensity of each line of the signal produced by the TDI detector corresponding to an image of an object is integrated over time as the image and corresponding signal propagate over the CCD array. This technique greatly improves the SNR of the TDI detector compared to non-integrating type detectors—a feature of great value when responding to images from low-level fluorescence emission of an object, for example.

The operation of the TDI detector can be understood from FIG. 8 by observing the traversal of object 68 across the region imaged by CCD array 64 and the history of the charge produced in response to the image of object 68 by CCD array 64. The charge is transferred from row to row in the array as the image of the object travels down the array. When a row of charge reaches the bottom of the array, it is transferred into scrolling memory 66, where it can be displayed or analyzed. In FIG. 8, objects 70 and 72 traverse flow tube 16 ahead of object 68, while an object 74 traverses flow tube 16 after object 68. Proper operation of the TDI detector requires that the charge signal be clocked down the CCD array in synchronization with the rate at which the image of the object moves across the CCD array. An accurate clock signal to facilitate this synchronization can be provided if the velocity of the object is known, and the present invention provides an accurate estimate of the objects velocity, and thus, the velocity of the image over the CCD array of the TDI detector.

Figure 9:
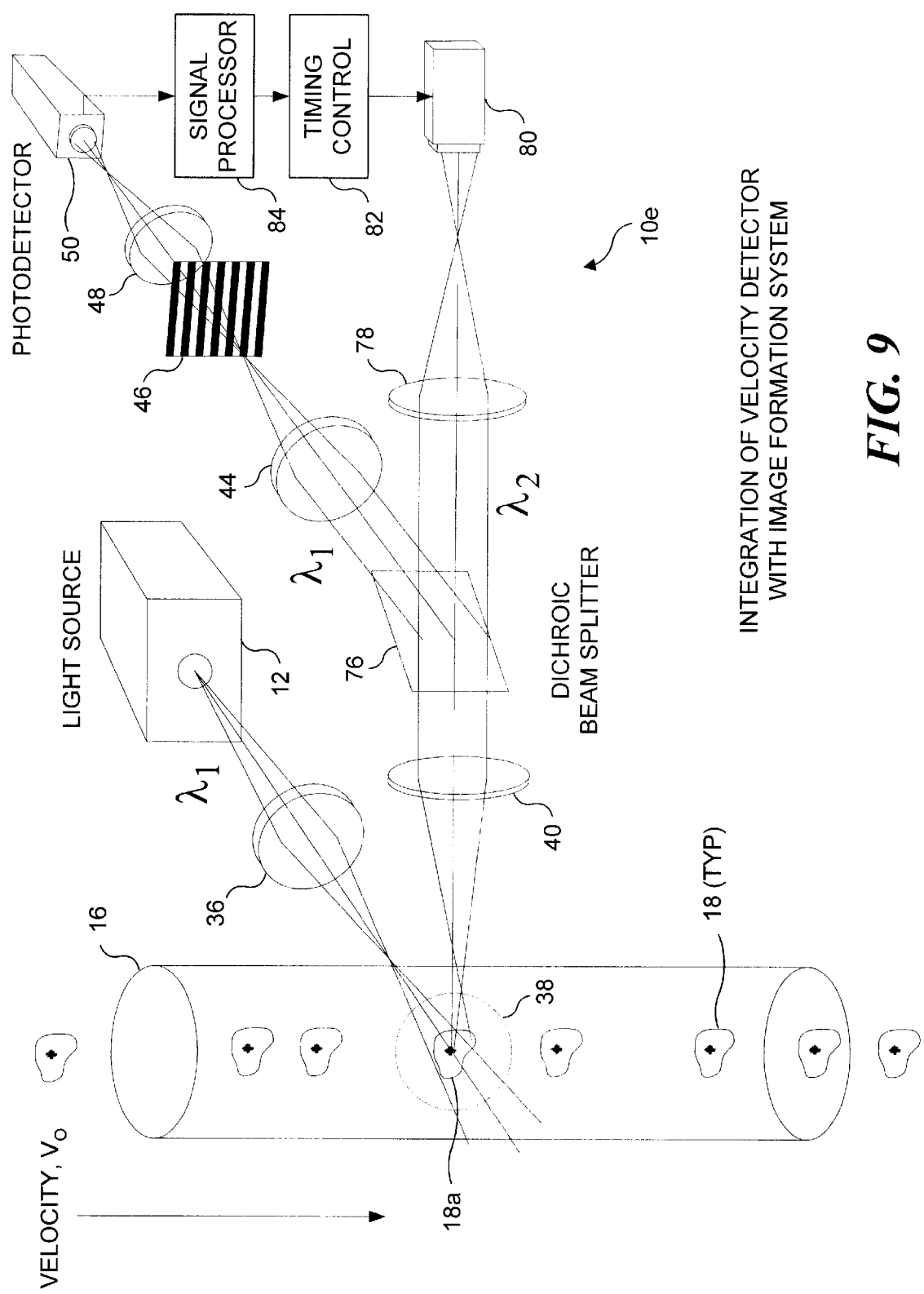
FIG. 9 is a schematic diagram of a flow imaging system including a flow velocity measurement system delivering timing to the TDI detector.

FIG. 9 shows the integration of the velocity detector into a TDI-based object imaging system 10e. The signal from photodetector 50 is processed by a signal processor 84, and may optionally carry out functions such as amplification and filtering. Additional details of the signal processing are provided below. Preferably, signal processor 84 comprises a programmable computing device, but an ASIC chip or digital oscilloscopes can also be used for this purpose. The frequency of the photodetector signal is measured and the velocity of object 18a is computed as a function of that frequency. The velocity is periodically delivered to a TDI detector timing control 82 to adjust the clock rate of a TDI detector 80. The TDI detector clock rate must match the velocity of the image of the object over the TDI detector to within a small tolerance to minimize longitudinal image smearing in the output signal of the TDI detector. The velocity update rate must occur frequently enough to keep the clock frequency within the tolerance band as flow (object) velocity varies. Note that a dichroic beam splitter 76 has been employed to divert a portion of light from object 18a to photodetector 50, and a portion of light from object 18a to TDI detector 80. An imaging lens 78 focuses an image of object 18a onto TDI detector 80.

Figure 10:
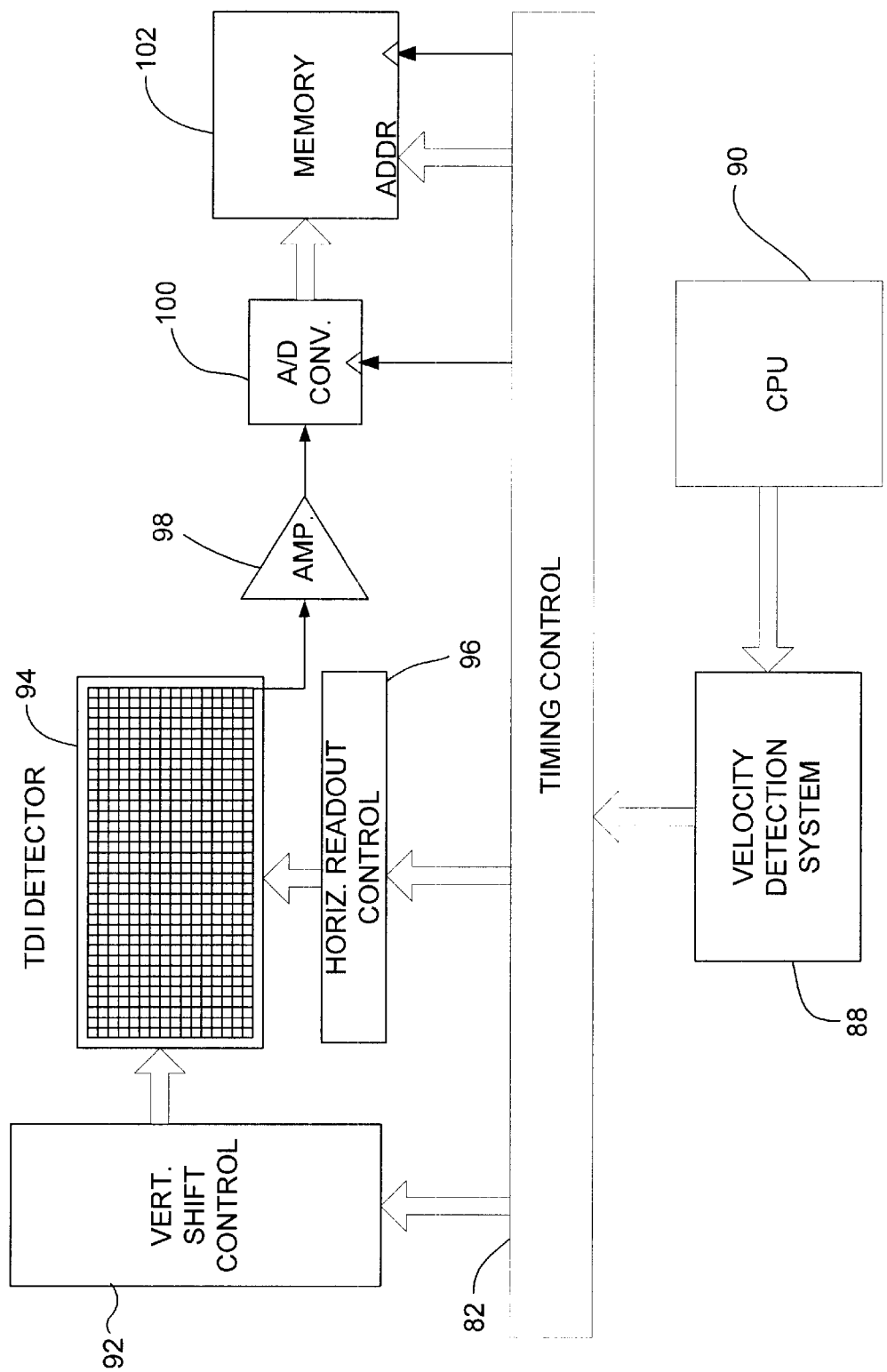
FIG. 10 is a block diagram of the structure of a TDI detector and the associated subsystems of the flow imaging system.

FIG. 10 shows how a velocity detection system 88 is preferably employed by TDI detector timing control 82 (shown in FIG. 9). Note that velocity detection system 88 can be configured as shown in FIG. 9, or provided in other configurations (such as shown in FIG. 5). Velocity detection system 88 provides a clocking signal indicative of the velocity of a flow or of objects in a flow for synchronizing the movement of images of the objects over a TDI detector with the movement of charge responsive to the images. The TDI detector is preferably included in a flow cytometry system, although other applications of the present invention are contemplated. Preferably, the velocity detection system is controlled by a CPU 90, which executes a velocity detection supervisor program defined by machine instructions that are stored in memory (not separately shown). Note that CPU 90 can also be employed to carry out the signal processing function of velocity detection system 88. The clocking of the charge through a TDI detector 94 is accomplished by a vertical shift controller 92 and a horizontal readout controller 96, both of which are driven by a TDI detector timing control system 82. The velocity detection system 88 passes a clock frequency command to TDI detector timing control system 86 to set a rate at which rows of charge are shifted down the TDI detector array. Detector timing control system 86 synchronizes horizontal readout controller 96 with vertical shift controller 92.

The image information leaves TDI detector 94 as an analog signal, which is then amplified with an amplifier 98 and digitized by an ADC 100. The ADC output is stored in a memory 102 under the control of timing control system 86, where it can be accessed for display and analysis.

Figure 11:
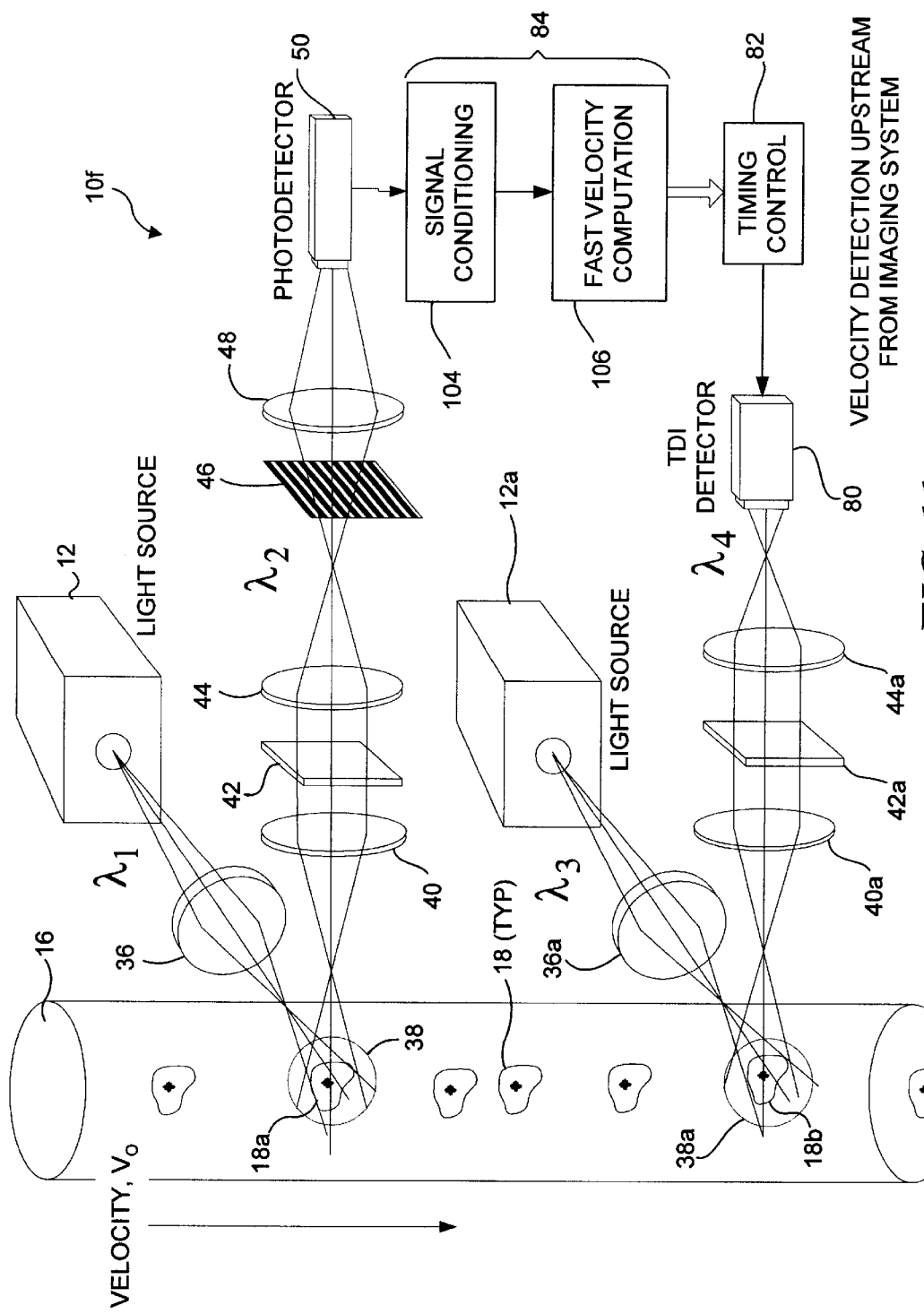
FIG. 11 is a schematic diagram of a flow imaging system in which object velocity measurement is performed upstream from image acquisition.

Another embodiment of a TDI-based flow imaging system 10e is shown in FIG. 11. This embodiment is intended to address the problem of synchronizing the TDI detector to individual objects traveling at different velocities, as may be the case in systems with poor hydrodynamic focusing. In TDI-based flow imaging system 10f, the velocity measurement is performed upstream of the point where image capture occurs. Velocity measurements are updated sufficiently rapidly to be passed forward to the TDI detector timing controller in time for the TDI detector clock (not separately shown) to be set to match the velocity of an image of a particular object moving across the TDI detector. The configuration of flow imaging system 10f is similar to that shown in FIG. 5, except that FOV 38 for velocity detection is separate from a FOV 38a used for TDI image acquisition. Imaging system 10f uses a separate light source 12a, separate lenses 36a, 40a, 44a and a separate filter 42a disposed in the collection path for light from the objects that is directed to TDI detector 80. The photodetector signal is processed using a signal conditioning component 104 and a FFT based fast velocity calculator 105 that is sufficiently fast to deliver new velocity estimates for objects to timing controller 82 in less time than required for the objects to travel from velocity measuring FOV 38 to imaging FOV 38a. Note that in imaging system 10f, signal processing block 84 of FIG. 10 is separated into signal conditioning component 104 and fast velocity calculator 106.

Accurate cell velocity measurements can also be employed to increase sort purity in droplet-based flow sorters. Such systems are typically PMT-based flow cytometers equipped to sort cells by their light scattering characteristics or fluorescence emission. In such systems, the characterization of a cell is performed just as the liquid carrying the cell leaves the droplet-forming nozzle. Based on an optical measurement, the unbroken part of the stream is either charged or not charged before the droplet containing the cell breaks free from the stream. An electrostatic field is used to deflect the charged droplets into a container separate from the container catching the uncharged droplets.

Figure 12:
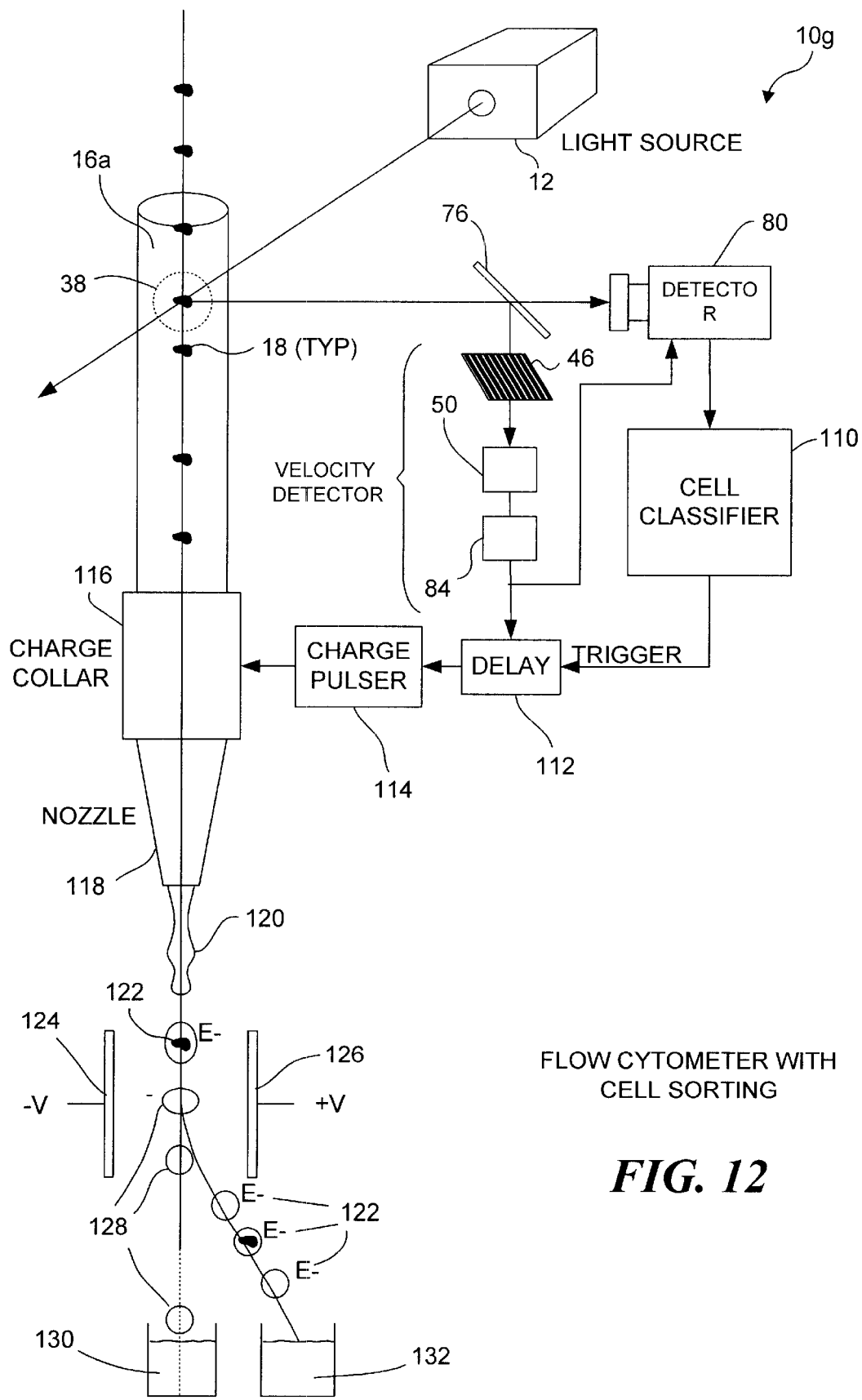
FIG. 12 is a schematic diagram of a cell sorting apparatus including the elements of a velocity measurement system controlling a droplet charging system.

FIG. 12 illustrates an instrument in which the optical grating-based velocity detection system of the present invention is used both to synchronize a TDI detector for capturing images and for timing the droplet charging system. In system 10g, both velocity detection and image capture are accomplished in common FOV 38. Images from TDI detector 80 are delivered to a high-speed cell classifier 110. The classifier searches the images for objects of interest. Once such an object has been found, the classifier automatically decides on the basis of the characteristics of that object whether the object should be sorted into a container 130 or a container 132. If the decision is made to place an object into container 132, the classifier triggers the charging system, which comprises a time delay operator 112, a charge pulser 114, and a charge collar 116. The time delay used by time delay operator 112 is set to match a transit time of an object from FOV 38 to an attached droplet 120, according to the velocity measurement performed in signal processing block 84 of the velocity detector. Note that as described above, the velocity detector includes optical grating 46, photodetector 50, and signal processing block 84. Charged droplets 122 are deflected into container 132 by the static electric field between electrodes 124 and 126. The distance between the optical sensing region and the charge collar is made long enough to provide sufficient time for image-based object classification to reach completion. In this way, a larger and more complex set of features can be used in the sorting decision than would be the case in conventional cell-sorting flow cytometers.

FDVM of Velocity of Objects on a Support

The first and second embodiments are directed to FDVM methods that convert light from cells or other objects into an amplitude modulated (AM) signal with a characteristic frequency that is proportional to velocity. Any number of cells traveling at the same velocity, e.g., in a fluid flow, can be in the sensitive region simultaneously, and the modulated light produced in response to the motion of each will have the same fundamental frequency, differing only in phase. Unlike the prior art time-domain methodology, the FDVM method requires no synchronization and is highly tolerant of variability in the fine structure of the time-based waveform generated by the cells.

In the FDVM method, moving luminescent or illuminated cells are imaged onto a ruling of transparent and opaque bars to generate an amplitude modulated light signal. The optical magnification and ruling pitch are chosen such that the bars are approximately the size (e.g., diameter) of the cell. The pitch of the ruling used in the optical grating is uniform. Therefore, the light collected from cells is alternately blocked and transmitted through the ruling as the cell traverses the sensitive region. The modulated light is directed toward a detector, producing an analog output signal with a fundamental frequency proportional to the cell velocity. The analog signal is converted to digital samples. An FFT algorithm decomposes the resulting digital signal into spectral peaks in the frequency domain, which are processed to determine the velocity. A first FDVM embodiment is directed to a method in which objects are deposited upon a support, and the support is moved through the FOV. A second FDVM embodiment is directed to a method in which objects are entrained in a fluid that is caused to flow through the FOV.

Figure 13:
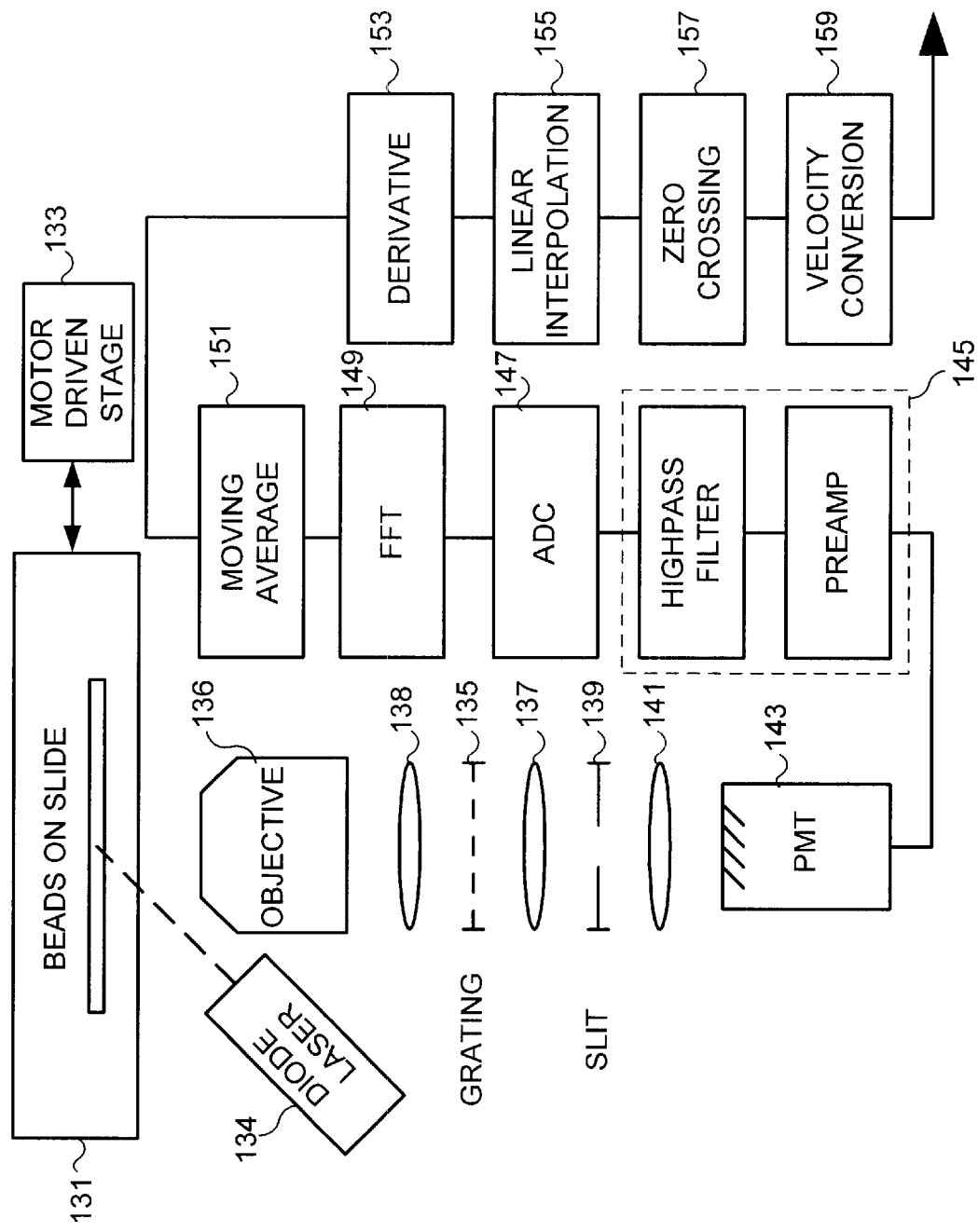
FIG. 13 is a block diagram illustrating a first embodiment of a frequency domain velocity measurement system in which objects are moved through a FOV on a support.

A block diagram of the first FDVM embodiment of a velocity detection system is shown in FIG. 13. Beads are deposited on a slide 131 that is driven through the FOV. For an initial feasibility study, the objects employed comprised 7.9 $\mu$m diameter beads (purchased from Bangs Corporation) fixed to a moving microscope slide. Movement of the slide through the FOV was produced by mounting the slide on a closed-loop DC servo stage 133 (available from Newport Corporation), and the sample speed was monitored using a one micron resolution linear encoder included in the stage. The stage had a maximum velocity of 100 mm/s, controlled using a proportional-integral-derivative (PID) control system (available from National Instruments Corporation). The linear encoder independently monitored the movement of the slide (and hence, the movement of the beads on the slide) to provide comparative data available to confirm the accuracy and precision of the FDVM velocity detection system. While it is expected that determining the velocity of objects entrained in a fluid will have widespread application, it is also anticipated that the moving support (slide) embodiment will also be useful, particularly for objects that cannot be easily or stably entrained or suspended in a fluid.

The sample beads were illuminated with light from a diode laser 134 (from Thor Labs, Inc.) so that light striking the beads was scattered into the optical collection system. The moving sample image was projected at approximately 5× magnification by an objective 136 and a lens 138, onto an optical grating 135 having a ruling of 50 micron bars (available from Gage Technologies), oriented at right angles to the motion of the sample. The ruling and sample were then imaged together on an adjustable slit 139 by an imaging lens 137, disposed to simulate the field of view of a flow-based instrument. The light passing through the slit was then collected by a lens 141 and directed onto a PMT 148 (Hamamatsu Corp., Model 5783-01) such that the aperture of the optical system was imaged onto the PMT (143). In this manner, there was no movement of the signal across the PMT as the bead images traversed the ruling.

The signal processing portion of this embodiment of a velocity detection system is also depicted in FIG. 13. The signal from the PMT was amplified and highpass filtered through an amplifier/filter 150 (Stanford Research, Model SR570). The filtered signal was then digitized using an analog-to-digital converter 147, and the digitized signal was processed using an FFT processor 149 to produce a frequency spectrum with a well-defined peak at the frequency corresponding to the velocity of beads. The FFT spectrum was smoothed using a moving average filter 151 and the zero crossing of the derivative of the smoothed FFT spectrum was determined in processing blocks 153, 155, and 157. All signal processing was performed on a digital storage oscilloscope (from LeCroy Corp.). The velocity of the objects on the slide was then calculated by taking the product of frequency defined by the zero crossing, the ruling spacing, and the inverse of the magnification in a velocity conversion block 159. The precision of the measurement was enhanced by linearly interpolating between the derivative data points to better define the zero crossing frequency.

Figure 14A:
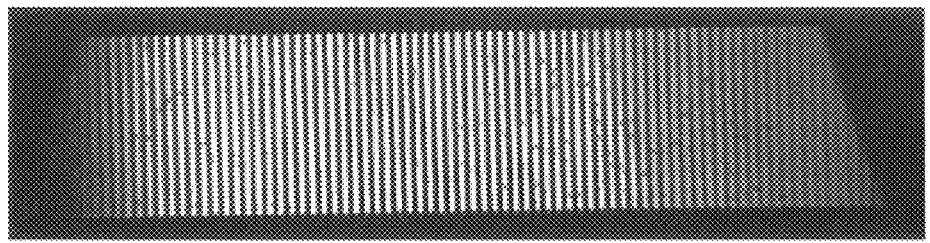
FIG. 14A is an image of beads, ruling, and an adjustable slit acquired by inserting a beam splitter, lens, and detector after the ruling, placing a light source behind the slide, and opening the slit for clarity.
Figure 14B:
FIG. 14B is a scattered light image with the slit of FIG. 2A closed down to 200 microns (40 microns in object space) and with the beads moving across the field of view at 20 mm/s, while data was acquired for approximately one second.

FIG. 14A shows an image of the beads, ruling, and adjustable slit. The image was acquired by inserting a beam splitter, lens and detector after the ruling, placing a light source behind the slide, and opening the slit for clarity. The beads were magnified 4.92× before being imaged on the ruling, which had a line width of 50.8 $\mu$m (9.842 lp/mm). FIG. 14B is a scattered light image in which dark field illumination was employed, and the slit closed down to 200 microns (40 microns in object space), as it was during data acquisition. In operation, the motorized stage moved the beads across the field of view at 20 mm/s (left to right in the illustrated example), while data was acquired for approximately one second.

Figure 15:
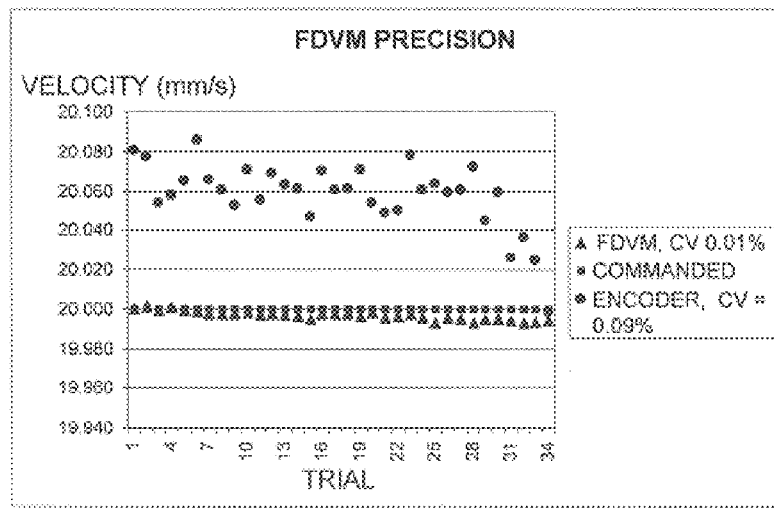
FIG. 15 is a graph illustrating experimental results for a closed-loop DC servo driven stage that drives 7.9 microns beads affixed to a microscope slide at 20 mm/s.
Figure 16:
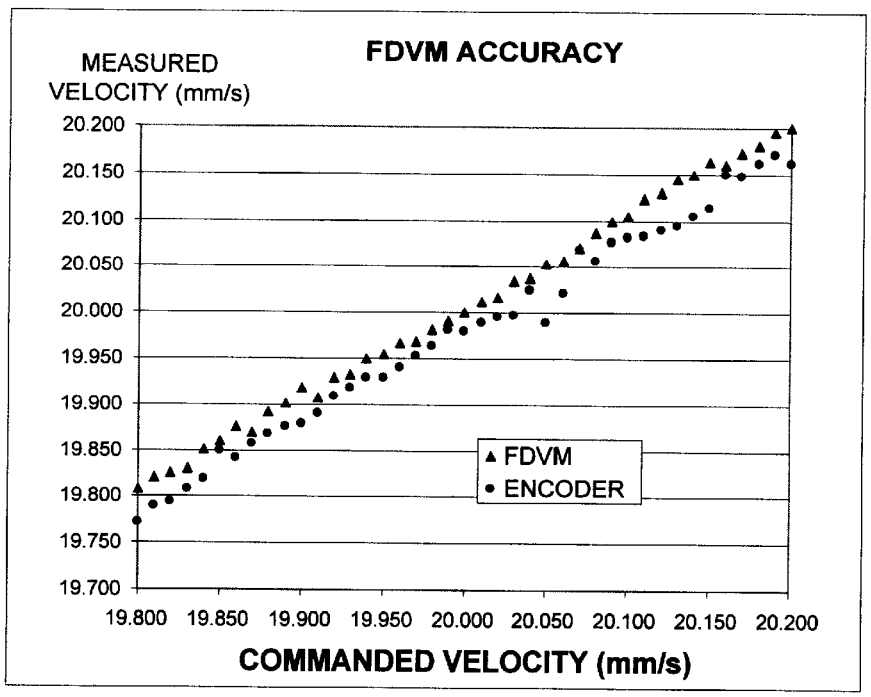
FIG. 16 is a graph of showing experimental results comparing commanded velocity to measured velocity, for the FDVM and encoder.
Figure 17:
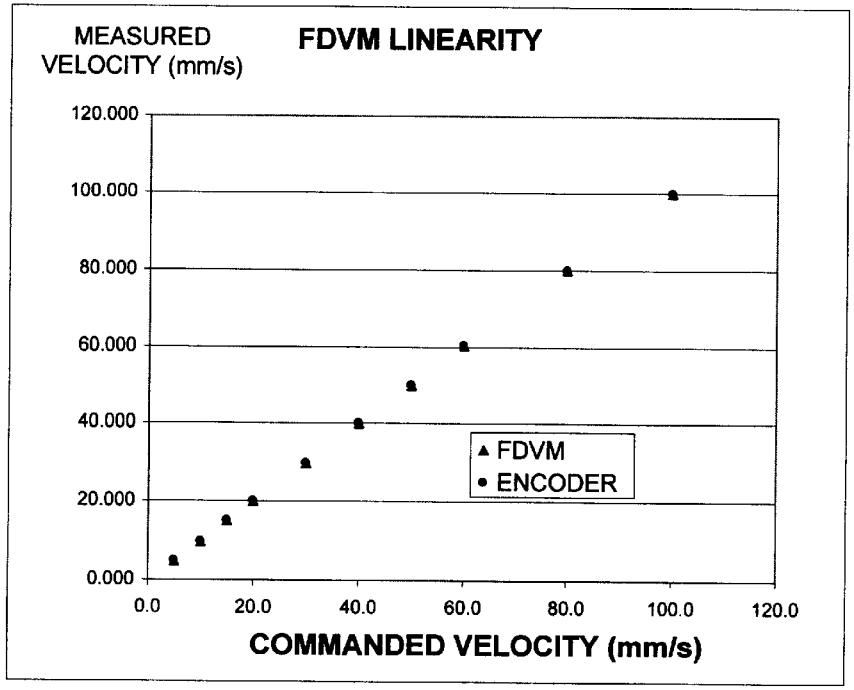
FIG. 17 is a graph of experimental results showing the linearity of the commanded velocity and measured velocity, for the FDVM and encoder.

Using the methods and apparatus discussed above, data were taken in three experiments to determine the precision and accuracy of the this technique. FIGS. 15, 16, and 17 summarize the results of these experiments. In the results of the precision experiment shown in FIG. 15, the stage was commanded to move at 20 mm/s in 34 separate runs. The velocities measured by the encoder on the stage and by the FDVM method of the present invention were both recorded and plotted. To calibrate the FDVM method, a correction constant was determined by taking the quotient of the first commanded velocity and the frequency peak produced by the FDVM method. Each subsequent measurement was multiplied by this value. The precision of the FDVM method was determined by calculating a coefficient of variation (CV) for 34 separate runs. By this measure, the precision of the encoder method is 0.09% and the precision of the FDVM method of the present invention is 0.01%, as shown in FIG. 16. This experiment demonstrates that the precision of the FDVM method exceeds targeted performance requirements by a factor of fifty.

It should be noted that the poorer apparent performance of the encoder method is likely the result of the servo feedback system's internal velocity calculation. Rather than making one velocity measurement per run using all 20,000 counts, the servo system makes a velocity measurement every 60 counts for the purposes of real-time motion control. The stage feedback system supplied a function to average the individual velocity measurements within a run. Each point in the encoder precision plot is therefore the average of 333 individual velocity measurements.

The results of the linearity experiment are shown in FIG. 17. The stage was commanded to move over a velocity range from 5 mm/s to 100 mm/s as specified in the performance requirements. Velocity measurements were taken using the FDVM method and the stage encoder. Over this range both measurements produced highly correlated $R^2$ values of unity with slopes of 1.0002 and 1.0007 for the FDVM method and stage encoder, respectively. These results demonstrate that the FDVM method of the present invention has good linearity over a range of velocity measurements exceeding an order of magnitude.

Figure 18:
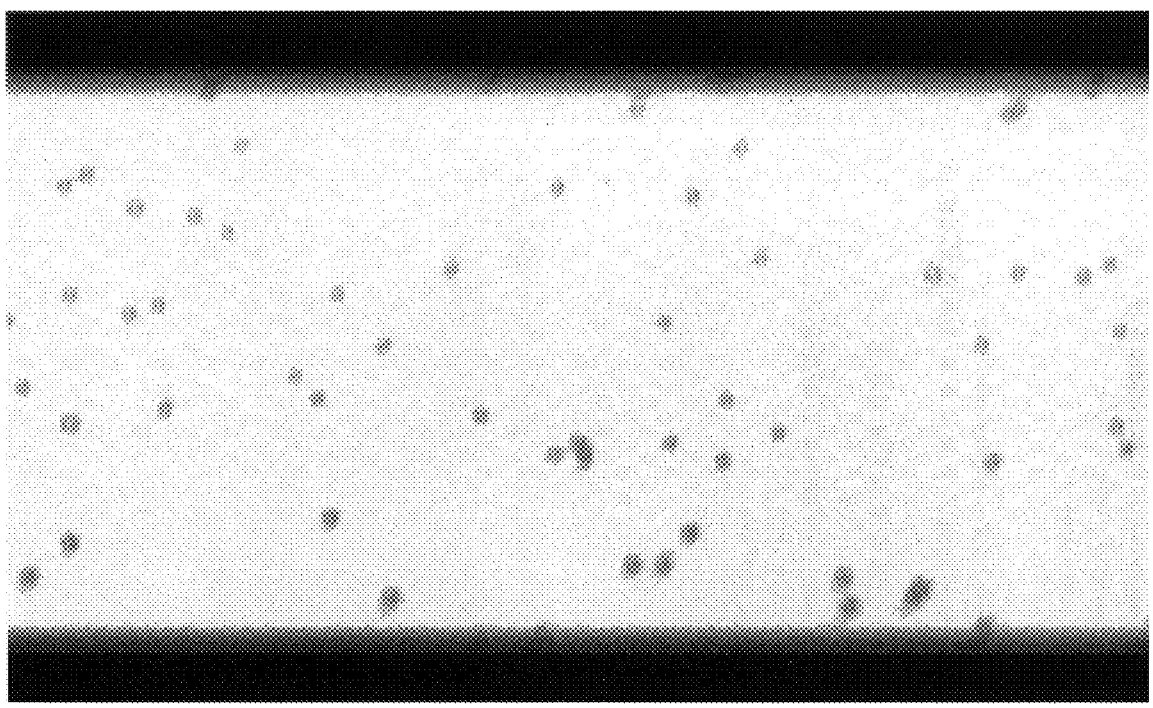
FIG. 18 is a TDI image captured using frequency domain velocity feedback.

FIG. 18 is an image captured using a TDI detector configured to view the sample slide, as in FIG. 2. The TDI detector or detector captures unblurred imaged of objects, which move at the same rate as the charge that is clocked across the chip during imaging. Because the TDI detector is located behind the stationary ruling, the ruling has blurred across the entire field of view. The ruling is responsible for some image degradation as each bead image traverses the entire ruling during the imaging process. The TDI detector's pixel clock was generated using the velocity determined by the FDVM method of the present invention. Although a comprehensive analysis of the image has not been performed, it is apparent that the velocity accuracy is sufficient to prevent image elongation in the horizontal axis of motion of the TDI detector.

The goals of the feasibility study employing beads on a slide were to develop a velocity detection system with high precision, high accuracy, good linearity and tolerance of wide variations in sample density. These goals were exceeded and the system was successfully used to capture images using a TDI detector. The 0.5% feasibility requirements were set to ensure less than one pixel blur when using the velocity detection system in concert with a 100 stage TDI detector. In fact, the feasibility system demonstrated precision, accuracy, and linearity better than 0.05% and therefore can be used with a 1000 stage TDI detector. In the context of the cell analysis system being developed in which the present invention will be included, more stages enable the image to be collected over a larger field of view, thereby increasing the integration time and the sensitivity of the instrument. Conversely, if the field of view is held constant, the pixel size can be reduced, increasing the spatial resolution of the instrument. Accurate velocity detection is also beneficial for cell sorting, where knowledge of the stream velocity can be used to actively adjust drop delays to compensate for drift over the course of an experiment.

Supervisory Control of Velocity Measurement Systems

In all embodiments, the present invention entails the steps of (1) formation of images of the objects of interest focused in the plane of the optical grating, (2) delivery of the modulated light transmitted by the optical grating to the surface of a photosensitive detector, (3) conversion of the modulated light signal to an electronic signal, (4) signal acquisition and processing, and (5) velocity determination. Preferably one or more of these operations will be brought under the control of supervisory software by interfacing the velocity measurement system with a general purpose computer or other computing device.

Figure 19:
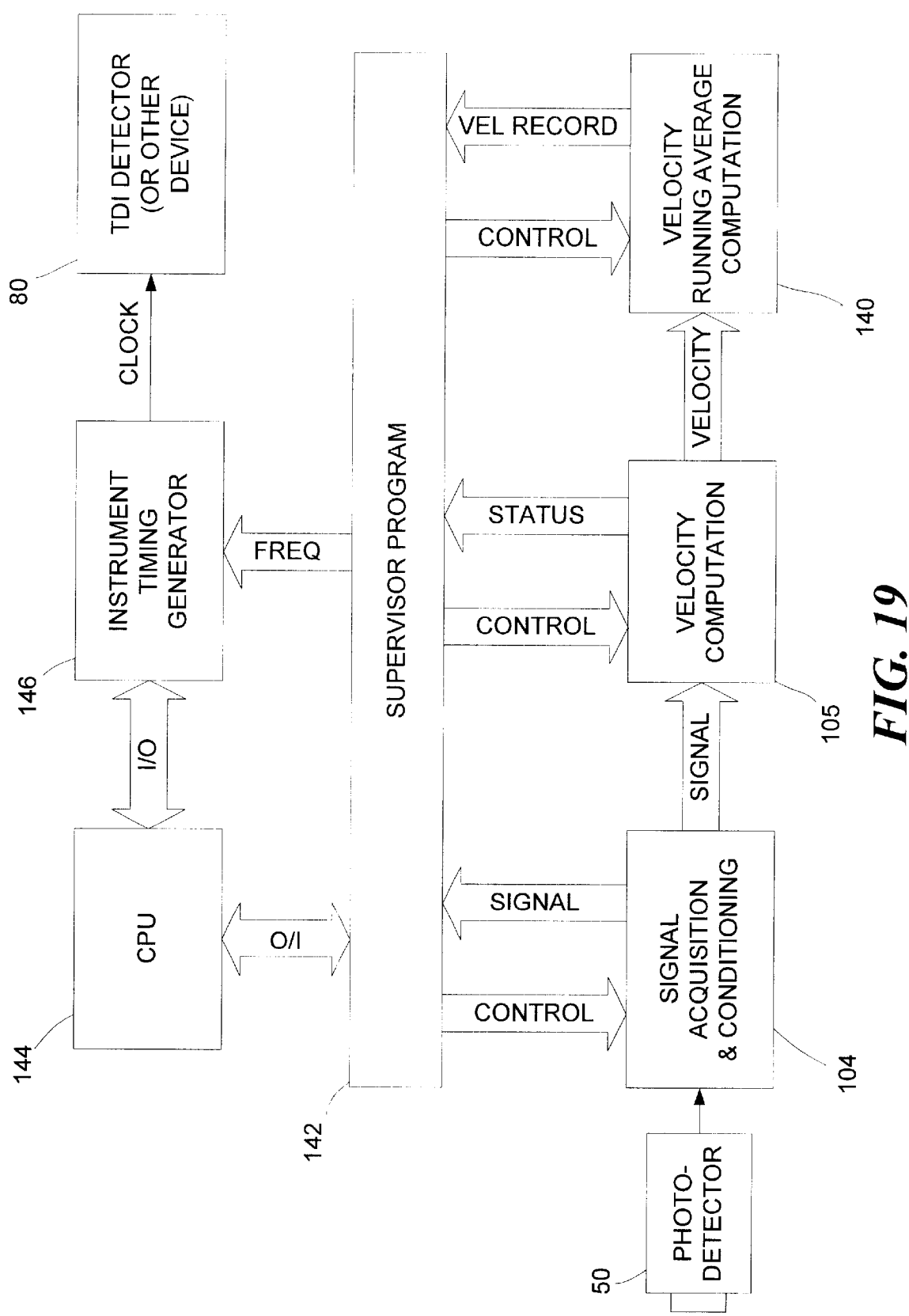
FIG. 19 is a block diagram of common components of flow velocity measurement systems, in accord with the present invention that are under the control of a system controller.

FIG. 19 is a functional block diagram of a signal acquisition and analysis system controlled by a supervisor program 142, preferably executed by a CPU 144 of a programmable computer. Alternatively, supervisor program 142 can be executed by a corresponding CPU in a digital oscilloscope, or by an ASIC chip. A signal from photodetector 50 is processed via signal acquisition and conditioning process block 104, velocity computation process block 105 (note that fast velocity computation process block 106 of FIG. 11 employs FFT processing, while, velocity computation process block 105 is more generalized, and can employ other types of signal processing, as opposed to just FFT signal processing), and a velocity running average computation block 140. Based on the velocity of an object that was determined, supervisor program 142 provides a clocking signal to a timing generator 146 that controls TDI detector 80. Note that the TDI detector is only one device exemplary device that can employ the present invention. It is expected that other types of devices can be provided a timing signal in this manner.

FDVM of Objects in Flow

Figure 20:
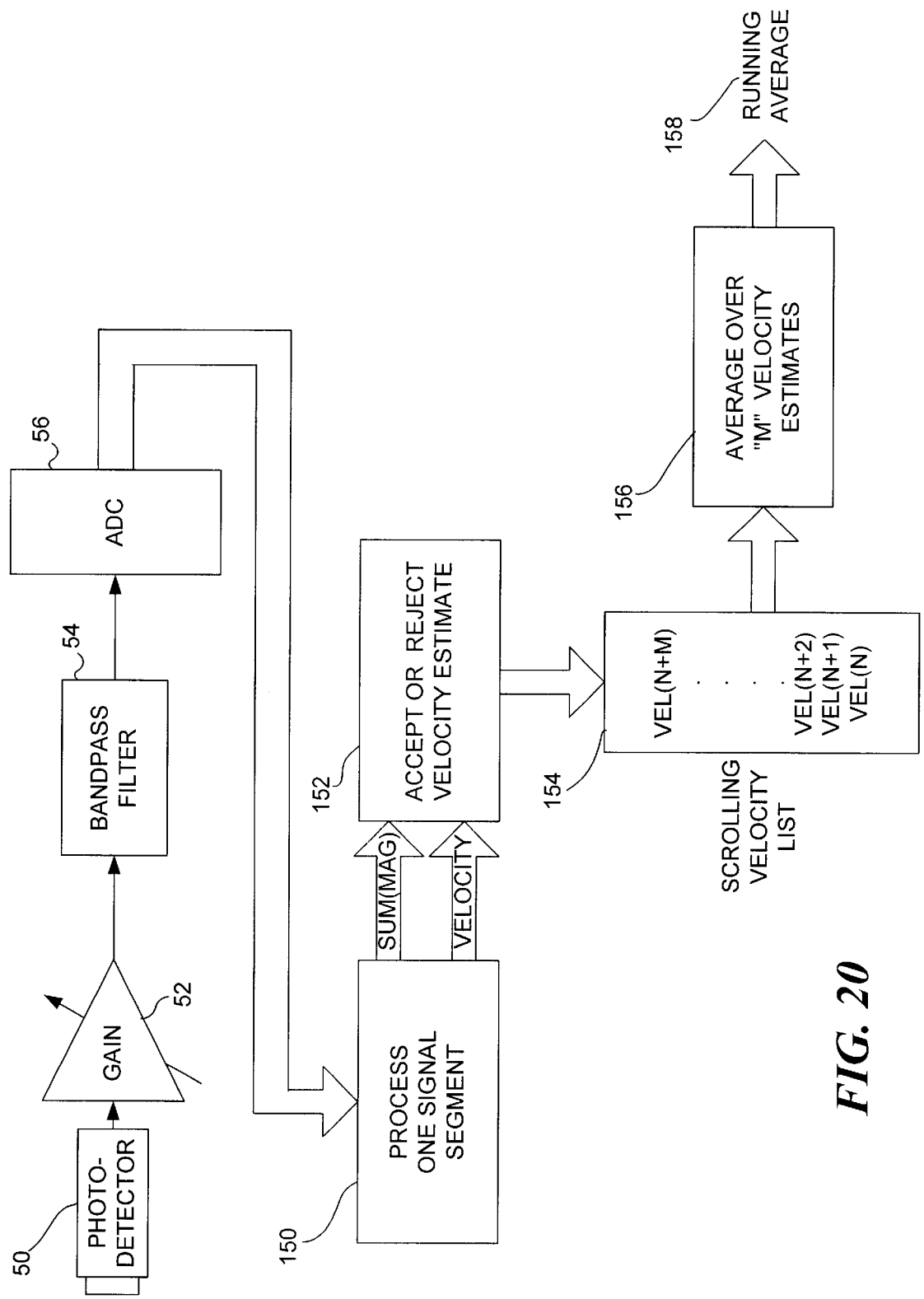
FIG. 20 is a block diagram illustrating the steps of the signal processing and velocity computation for a second preferred embodiment of the present invention.
Figure 21:
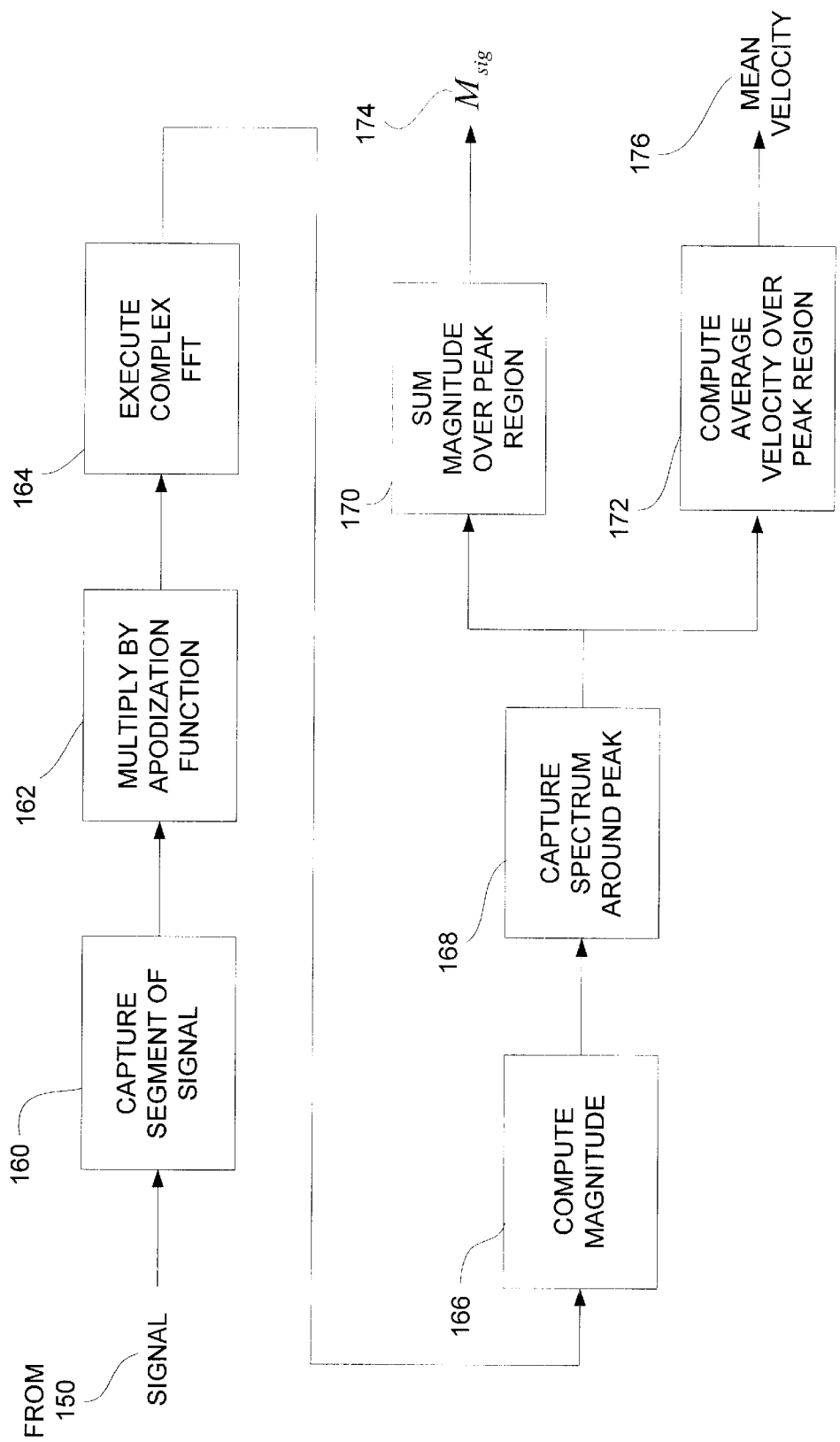
FIG. 21 is a block diagram illustrating the steps comprising the signal processing for the embodiment of FIG. 20.

In the second preferred embodiment of the present invention, the light from the objects is modulated by the optical grating, and the modulated light is sensed by the photodetector shown in FIG. 5. The functional blocks used to capture, process, and analyze the photodetector signal are shown in FIG. 20. Details of a multistage digital signal processing operation 150 for processing the incoming signal are illustrated in FIG. 21. The entire system, shown in FIG. 20, operates as a pipeline processor in which blocks of signal samples, and farther down the pipeline, parameters calculated from the blocks of samples are passed from one operation to the next in an uninterrupted sequence.

As explained above in connection with FIG. 6, the signal produced by photodetector 50 is input to variable gain amplifier 52. The output of variable gain amplifier 52 is filtered by bandpass filter 54 to remove the DC bias caused by stray light and by bias voltage of variable gain amplifier 52 and to eliminate frequencies above the Nyquist limit of ADC 56, this limit being equal to one-half of the sample frequency, $f_{samp}$. After bandpass filtering, the signal swings in both the positive and the negative direction around a mean value of zero.

ADC 56 samples the signal at frequency $f_{samp}$ and encodes the signal into a series of digital samples representing the signal amplitude at each sequential sample time. The converter must retain the bipolar nature of the signal by encoding the signal into a number system such as the 2's complement format, which accommodates both positive and negative numbers.

As an alternative, ADC 56 could be placed immediately after variable gain amplifier 52 and bandpass filter 54 could be implemented as a digital instead of an analog type filter. The signal applied to the ADC would then be unipolar, and the signal would be encoded into a simple binary number for processing.

In a multistage digital signal processing block 150, one signal segment is processed. Referring now to FIG. 21, in block 150, a sequential series of signal samples of predetermined length, N_segment, is analyzed to extract the mean frequency of the photodetector signal and to convert that frequency to an estimate of the object velocity. The first step 160 of this operation is to capture the desired number of samples for the segment from the incoming signal.

Optionally, the next signal processing step 162 applies an amplitude windowing or apodization function to the signal segment that was just captured. Without this apodization step, the abrupt truncation of the signal at the ends of the segment would spread the frequency components in the signal over a collection of sidebands, the frequency and amplitude of which conform to the Fourier Transform of a rectangular window, a sine function in frequency space. Those skilled in the art will recognize that apodization by a function such as the Hamming, Hanning, or raised cosine functions, for example, will substitute a smoother sideband structure of lower amplitude in place of the sine function. The reduced sideband amplitude improves the accuracy of estimating the mean frequency of the photodetector signal, especially in the presence of velocity dispersion. Alternatively, apodization can be performed optically by illuminating the FOV using a smooth-shouldered intensity profile, thereby eliminating the abrupt truncation of the signal at the edges of the FOV. In still another method of apodization, the ruling may be superimposed on a varying transmission gradient filter, which smoothly attenuates the optical signal at the edges of the FOV.

The optional apodization operation in step 162 is followed by execution of a complex FFT function in a block 164. The complex FFT algorithm is utilized by applying the signal as the real input to the FFT and applying an array of length N_segment with all values set to zero as the imaginary input to the FFT. Alternatives exist for utilizing the FFT algorithm more efficiently for real-number transforms, but those methods involve packing the input arrays in special patterns and unpacking the output arrays. Such methods can be used, however, to save processing time.

The resulting complex number spectrum is then applied to an operator in a block 166 that converts the real and imaginary parts of the spectrum to the magnitude of the spectrum using the following relation:

$$M_j = \sqrt{Re_j^2 + Im_j^2}$$

where:
M$_j$=magnitude at sample j
Re$_j$=real part of sample j
Im$_j$=imaginary part of sample j.
Typically, this operation will be implemented using a lookup table or fast approximation algorithm to speed execution.

Typically, the velocity of the objects to be imaged with a TDI detector will deviate very little from the mean velocity. Consequently, the power in the spectrum of the signal from the photodetector will be concentrated in a narrow band around a mean frequency, and the spectrum outside this band can be ignored in the computation of mean frequency.

Figure 22:
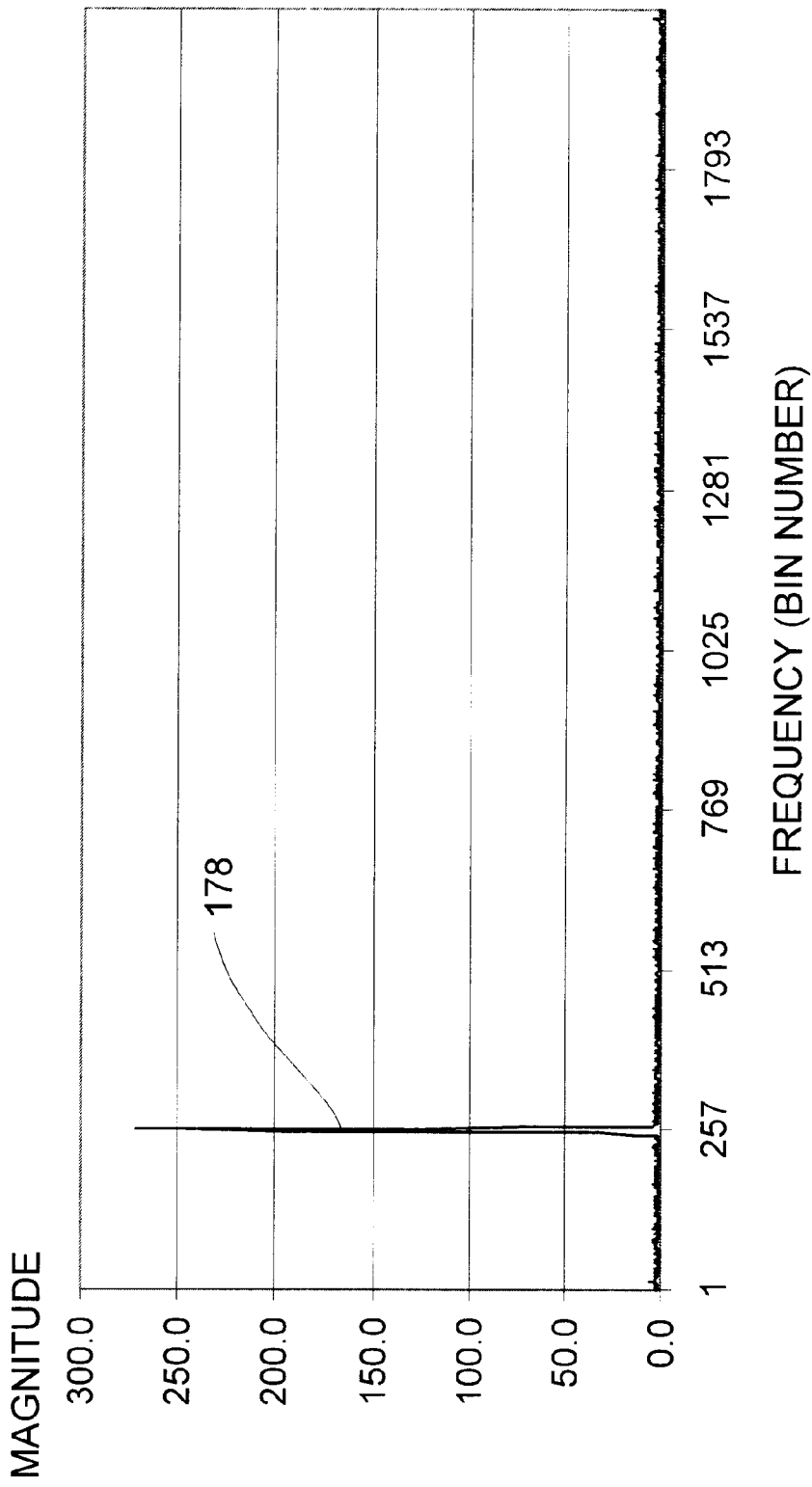
FIG. 22 is a graph of an exemplary spectrum of an unmodulated photosensor signal for a single object.
Figure 23:
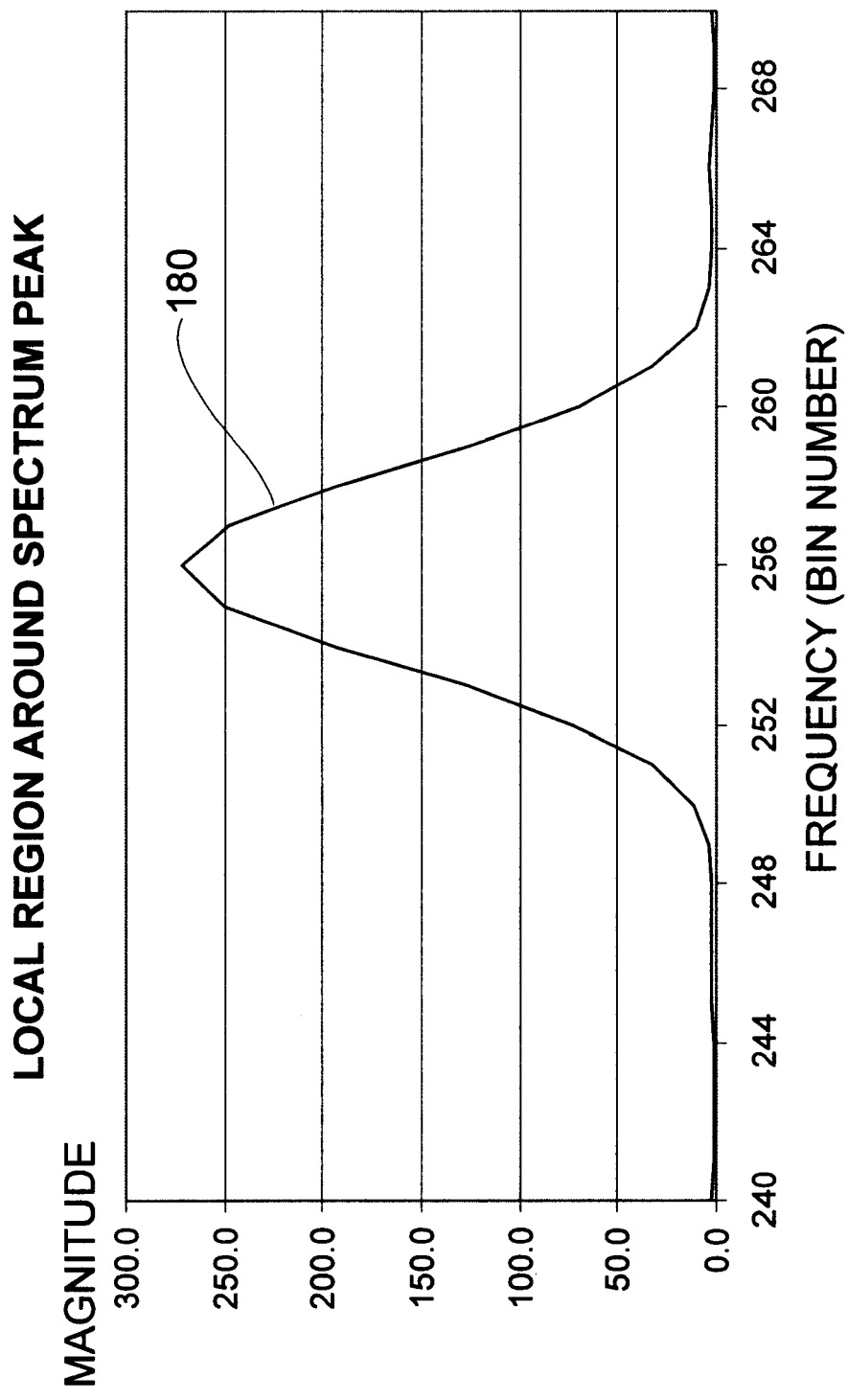
FIG. 23 is an enlarged view of the graph of FIG. 22, illustrating the signal peak.

FIG. 22 is the spectrum produced by a sinusoidal burst with center frequency 2500 Hz and a Gaussian-shaped envelope. A single object passing through the flow cell of a flow imaging system such as that illustrated in FIG. 9 might produce such a signal. A simple peak detector is applied to the spectrum in FIG. 22 in a block 168 of FIG. 21, to localize a region 178 of the spectrum of interest for analysis. FIG. 23 shows a segment 180 of the spectrum centered on the peak of the spectrum of the signal burst. This segment contains nearly all of the power in the spectrum and can be utilized for computing the mean velocity.

In a block 172 of FIG. 21, the mean velocity is determined by finding the mean frequency on the scale of FFT bins from the signal segment of FIG. 17. The following relation describes this calculation:

$$\bar{n} = \frac{\sum_{n=a}^{b} n S(n)}{\sum_{n=a}^{b} S(n)}$$

where:
a, b=endpoints of sample in window
S=magnitude of spectrum
n̄=mean FFT bin (floating point).
The mean frequency in Hz is computed from the mean FFT bin number as follows:

$$\bar{f}(Hz) = 2 \cdot \bar{n} \cdot f_{Nyq}/N$$

where:
f$_{Nyq}$=Nyquist frequency
N=FFT length
f̄=mean frequency.
Finally, a mean velocity 176 is found by multiplying the mean frequency by the optical grating pitch:

$$\bar{v} = \bar{f} \cdot s$$

where:
s=grating pitch (microns)
v̄=velocity (microns/sec).

The velocity detection system must accommodate the possibility that very little or no signal was captured in the signal segment being processed. In the present embodiment of the invention, the magnitude of the spectrum integrated over the local region around the peak of the spectrum is computed in a block 170, as follows:

$$M_{sig} = \sum_{n=a}^{b} S(n)$$

where:
M$_{sig}$=integrated magnitude, this segment
S=magnitude of spectrum
a=first bin of local region around peak
b=last bin of local region around peak.

As will be appreciated from the description of the supervisor program for the velocity detection system that follows, a running record of the mean velocity will be maintained by the supervisor and used to establish the boundaries, a and b, of the local region for computing the mean frequency and an integrated magnitude 174.

Referring back to FIG. 20, the mean velocity and integrated signal magnitude from operation 150 are applied to a decision step 152. The decision step 152 yields two possible outcomes: (1) the SNR of the segment being processed is adequate for computing the velocity, so that the new velocity value is added to a velocity list 154, or (2) the SNR is inadequate (below a predefined value) for computing the velocity, and the velocity list remains unchanged. If a new velocity value is added to the velocity list, the oldest value on the list is deleted (once the list is full). Velocity list 154 and a running average calculation in a step 156 deliver a new velocity estimate every time a new signal segment is processed. The running average velocity is the average over a predetermined number of velocity values, m. The number of values, m, used in the running average can be increased to improve the accuracy of the running average or decreased to improve the responsiveness of the velocity detector to rapid changes in velocity.

Figure 24:
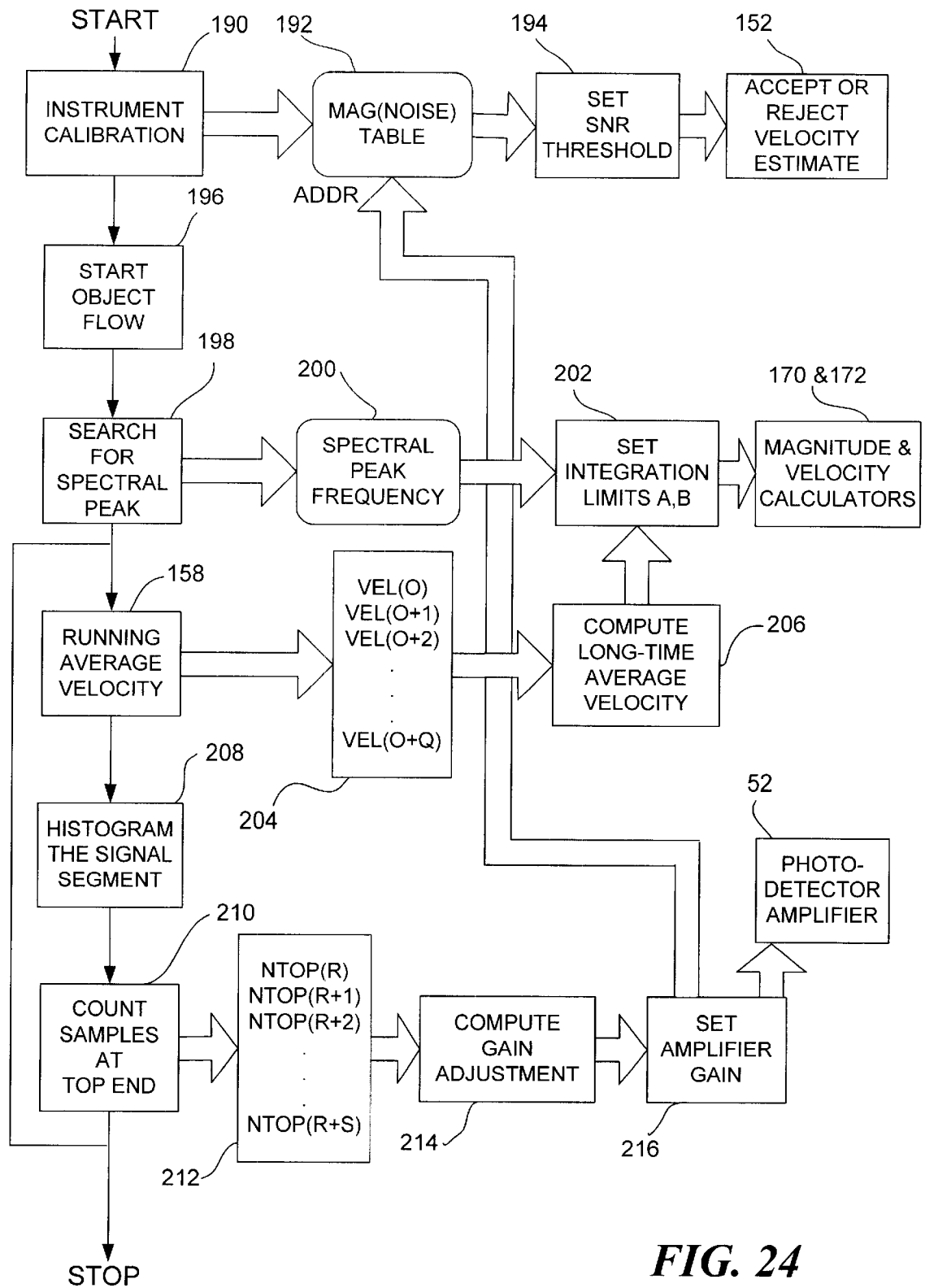
FIG. 24 is a block diagram illustrating the steps employed by the supervisory program for controlling the second embodiment of the present invention.

The velocity detector must adapt to variations in flow velocity and photodetector SNR in order to produce accurate and reliable velocity estimates. Supervisor program 142, shown in FIG. 19, is used to control the velocity detector and to coordinate the operations of the velocity detector with those of the rest of the imaging system. FIG. 24 is a flowchart showing the steps implemented by the supervisor program for the second embodiment of the present invention. The program's three principal outputs, the SNR decision threshold, the spectrum integration limits, and the photodetector amplifier gain, are fed back to the velocity measurement system to optimize its performance.

Operation of the velocity detection system is initiated with an instrument calibration step 190, in which the noise from the photodetector channel is determined and analyzed in the absence of an optical signal. This can be accomplished by turning off the light sources in the system or stopping the flow of objects through the flow cell. The purpose of the noise measurement is to establish a reference against which the information-bearing signal will be compared for setting a threshold for accepting or rejecting velocity measurements.

The calibration operation measures the noise level at a plurality of amplifier gain settings and stores these measurements in a table 192 of noise level vs. gain. Table 192 is used to select an initial gain setting for amplifier 52. As the amplifier gain is varied to regulate the signal strength during normal operation, the correct noise level for setting the decision threshold is read from table 192 and applied to threshold calculator 194. Once the calibration operation has been completed, the light source or sources are turned on, and objects are introduced into the flow stream for image acquisition, as shown in a step 196.

The next task of the supervisor program is to search for the peak in the spectrum in a step 198 and set the upper and lower boundaries of the spectral region to be analyzed. In the absence of any a priori knowledge of the flow speed, this initial search must span the entire range of frequencies in the spectrum, and may entail capturing a number of signal segments until a strong peak representing a spectral peak frequency 200 is found. The location of that peak will be used to set the local region boundaries, using knowledge of the expected width of the spectrum.

This width is a function of the beam profile of the illumination field, the shape of the apodization function, and the predicted variance of object velocities. This information will be understood from the design of the instrument.

With the photodetector amplifier gain set to a starting value and the decision threshold and integration limits established, pipeline processing of signal segments commences. Each time a segment is processed, running average velocity value 158 is added to a list 204 and the oldest value in the list is deleted. The velocity values in list 204 are then averaged in a step 206. This long-time average of the velocity is used in a step 202 in which the boundaries of the local spectral region to be analyzed are set. The process of regulating the integration limits constitutes a feedback control loop in the supervisor program. The response time of this loop can be modified by adjusting the number of samples maintained in list 204 and averaged in step 206.

The gain of the photodetector amplifier is regulated during system operation as well, in order to optimize the SNR of the velocity detector as specimen characteristics change. The amplifier gain regulation system of the supervisor program in a step 208 provides for creating the histogram of each signal segment, counting the number of samples occupying a predetermined number of levels near the top of the analog-to-digital converter output scale in a step 210, maintaining a list of the most recent count results in table in a step 212, and analyzing that table to generate a gain adjustment in a step 214.

The time of arrival of objects in the FOV of the velocity measurement system is a random variable. If the specimen contains a high concentration of objects, the probability that an object will pass through the FOV in a given time interval is high, and the count table of step 212 will contain many samples useful in setting the amplifier gain. However, if the specimen contains a very low concentration of objects, many of the signal segments processed by the velocity detection system will be devoid of signal, and the count values stored in the count table of step 212 for those segments will be zero. Those skilled in the art of automatic gain control systems will recognize this problem as similar to that of regulating the gain in radio receivers or studio microphone amplifiers, in which the signal being processed may vary widely in amplitude and be interrupted. The common practice in such cases is to use a "fast attack," "slow recovery" feedback control system. In such a system, the sudden arrival of a high-amplitude signal will be met with a fast reduction of amplifier gain to prevent saturation. On the other hand, a prolonged interruption of the signal is met with a slow increase in gain, on the premise that a large signal is likely to arrive soon, but a persistent loss of amplitude, requiring higher gain may have occurred. The gain adjustment determined in step 214 will use a "fast attack," "slow recovery" algorithm to regulate the photodetector amplifier gain. Determination of running average 158, and steps 208 and 210, and their associated feedback control mechanisms will sustain sequential processing of signal segments until terminated by the supervisor program.

The new gain setting is set in a step 216 for variable gain amplifier 52 in regard to noise calibration table 192. The response time of the gain control feedback loop can be modified by adjusting the number of samples maintained in table 212 and analyzed in step 214.

TDVM of Objects using a Single Uniform Pitch Optical Grating

In the third preferred embodiment of the present invention, the light collected for velocity measurement is modulated by an optical grating having a substantially uniform pitch and sensed by the photodetector shown in FIG. 5, just as in the second embodiment. The analysis of the photodetector signal, however, is performed in the baseband domain. Baseband demodulation is frequently used in communications and other signal processing applications for receiver tuning and carrier rejection. The fundamental architecture of a baseband demodulator with the additional capability of splitting the signal into upper and lower sidebands, is shown in FIG. 25 and is referred to herein as "the double-sideband receiver."

Figure 25:
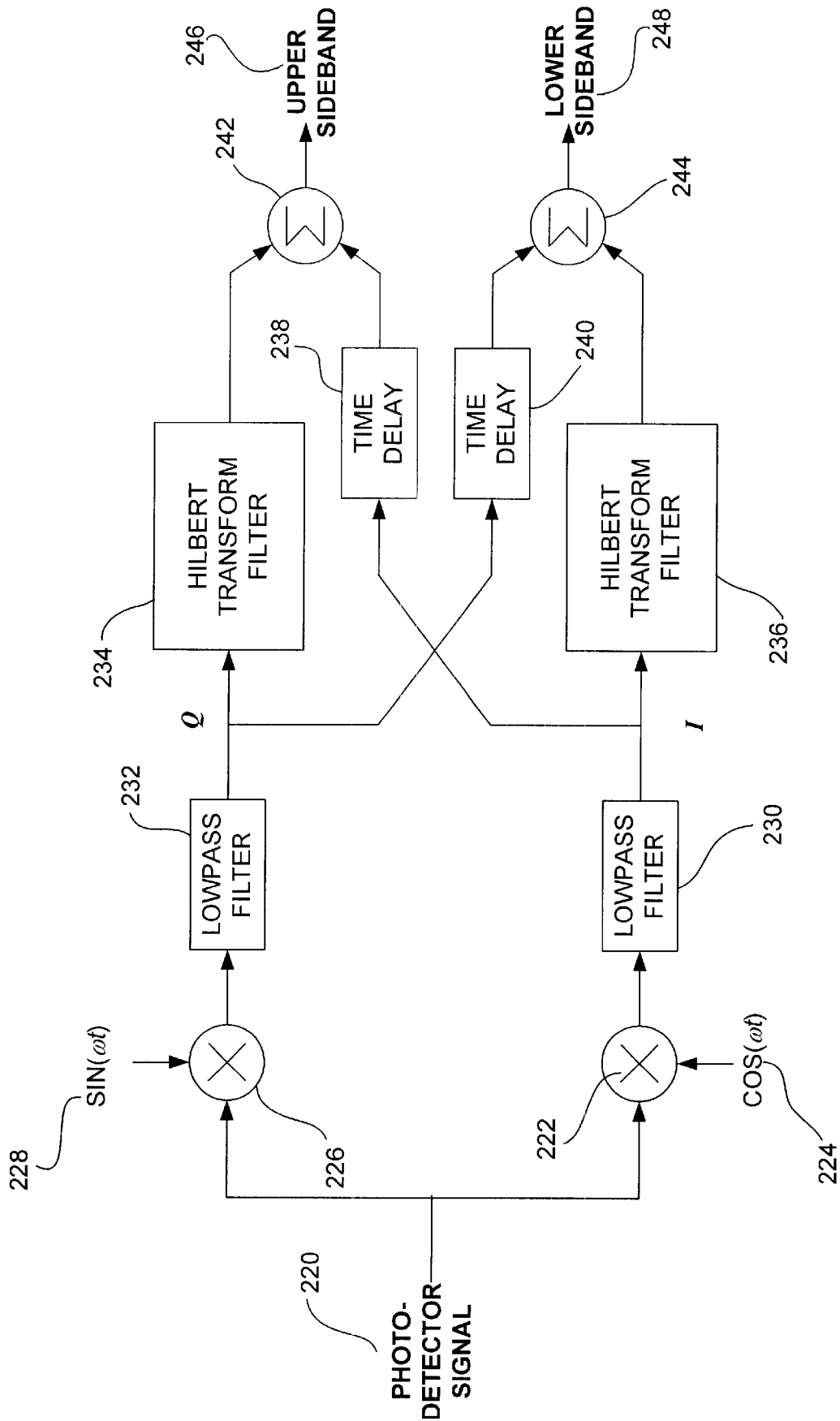
FIG. 25 is a block diagram of a double sideband receiver for use in a third embodiment of the present invention.

As shown in FIG. 25, an incoming signal from the photodetector is applied to multipliers (or mixers) 222 and 226, which multiply the signal by two continuous sinusoidal wave functions, called local oscillator signals. The two local oscillator signals are at the same frequency, but shifted in phase ninety degrees relative to one another. That is, a first local oscillator signal 224, which is the in-phase local oscillator signal, is a cosine function, while a second first local oscillator signal 228, which is the quadrature-phase local oscillator signal, is a sine function. The mixers are followed by lowpass filters 230 and 232, which complete the baseband demodulation.

The effect of multiplying the signal from the photodetector by a sinusoid of frequency $f_{LO}$ is to offset the spectrum of the incoming signal upward by $f_{Lo}$, to create sum frequencies, and downward by $-f_{LO}$, to create difference frequencies. In FIG. 26, a sinusoidal burst with the spectrum shown in a graph 250 at a center frequency of 1500 Hz is applied to mixers 252 and 256, driven by local oscillator signals 254 and 258, set to 2000 Hz. At the output of the mixers, the center frequencies in the spectrum are the difference frequency, 500 Hz, and the sum frequency, 3500 Hz, as shown in graph 264. Lowpass filters 260 and 262 suppress the sum frequencies, leaving only the difference frequencies in the I(t 268 and Q(t) 266 signals, as shown in a graph 270.

The lowpass filter outputs are the I and Q signals, i.e., the in-phase and quadrature-phase signals. FIG. 27 shows how signals entering and leaving the baseband demodulator might look on an oscilloscope. Each time sample is a complex number representation of the input signal 272, with the I channel 268 representing the real part of the complex signal, and the Q channel 266 representing the imaginary part of the complex signal. Graph 276 shows the in-phase output signal, while graph 274 shows the quadrature-phase output signal. The I,Q pair conveys both the magnitude of the signal and the phase of the input signal 272 relative to the local oscillators. A time series of I,Q pairs can represent both positive and negative frequencies, which derive from frequencies above the local oscillator frequency and below the local oscillator frequency, respectively. The time series of I,Q pairs is often referred to as the "analytical signal."

The magnitude and the phase of the input signal can be calculated from the analytical signal using the vector operations shown in FIG. 28. The magnitude of a signal 282 is computed in a step 278. I(t) and Q(t) are the Cartesian projections of the vector M(t), therefore M(t) is just the length of the hypotenuse of a right triangle with the other two sides being I(t) and Q(t). The equation for calculating M(t), then, is:

$$M(t)=\sqrt{I(t)^2+Q(t)^2}.$$

Accordingly, the angle between the real, I(t), axis and the hypotenuse, M(t), is the inverse tangent of Q(t)/I(t), or:

$$\Phi(t)=\arctan[Q(t)/I(t)].$$

The analytical signal offers a versatile method for tracking the photodetector signal frequency in the velocity detector. The frequency at every sample time is found by taking the time derivative of the phase of the analytical signal in a step 280. However, as seen in a graph 284 of Φ(t), the phase is a periodic function. The values π and −π define the same angle, where the abrupt transitions occur in graph 284.

In order to calculate a phase derivative for each time sample, the periodic Φ(t) function must be converted to a continuous function. FIG. 29 illustrates the unwrapping of the phase of a constant frequency signal. The function Φ(t) is shown in a graph 288. A polar plot 286 shows a rotating vector representation of a constant amplitude, constant frequency signal. It can be seen from plot 286 that the phase will make an abrupt transition from π to −π once per period. A phase unwrapping algorithm 290 senses these transitions and corrects for them to produce a monotonically increasing function of phase, as shown in a graph 292.

FIG. 30 describes the phase unwrapping algorithm. In a first step 294, the change of phase from one time sample to the next is computed without regard to the values of Φ(n) and Φ(n−1). In the next two stages, steps 296 and 298, the presence of a transition across the π,−π boundary is sensed and the phase derivative is corrected. The first part of both steps 296 and 298 is to detect that the phase has moved from one half-plane to the other half-plane. If Φ(n−1) was zero or positive, then the transition was from the upper half-plane to the lower half-plane, and the step 296 is executed. If Φ(n−1) is negative, then the transition was from the lower half-plane to the upper half-plane, and the step 298 is performed. In step 296, a further test is performed to determine if Φ(t) has changed in the negative direction by more than π. If so, then the transition between half-planes was at the π,−π boundary. In this case, an offset of +2π is applied to ΔΦ, which eliminates the impact of the boundary transition. In a similar manner, if step 298 detects that the phase has rotated across π,−π boundary in the clockwise direction, it subtracts 2π from ΔΦ to eliminate the impact of the boundary transition. Application of the unwrap algorithm to the phase signal from the baseband demodulator is used to generate a smooth phase plot, $\Phi_m(t)$, as shown in graph 292 of FIG. 29. The slope of this plot is the radial frequency, ω(t).

Any signal generated by a physical system will contain some random noise. Because ω(t) is computed using a difference operator, and true random noise is uncorrelated from sample to sample, the accuracy of the ω(t) calculation will degrade rapidly with decreasing SNR. For this reason, time samples of ω(t) are accepted into the velocity computation only if the magnitude of the signal is above a predefined threshold. This concept is illustrated by FIGS. 31A and 31B. In a graph 302 of FIG. 31A, a threshold of 0.1 is applied to the magnitude, M(t). The baseband frequency is computed only for those samples exceeding the threshold, yielding a result like that seen in a graph 308 of FIG. 31B. The term "fractional frequency" 310 used in graph 308 means the frequency expressed as a fraction of the Nyquist limit in baseband. The fractional frequency can have a value in the range from 0.0 to 1.0.

FIG. 32 shows the signal processing and data pathways for the third embodiment. The signal from photodetector 50 is applied to variable gain amplifier 52, the gain of which is regulated by the supervisor program to optimize SNR. The amplified signal is applied to bandpass filter 54 to remove DC offset and to limit the signal bandwidth to prevent aliasing. The filtered signal is converted to a sequence of digital sample by ADC 56. Mixers 222 and 226 and lowpass filters 230 and 232 (FIG. 25) are implemented in the baseband conversion of a step 311. The baseband signal pair I(n), Q(n) is used for two steps. The first is the generation of the upper sideband and lower sideband signals 314 and 322 in a step 312. The second is the measurement of the velocity of objects passing through the flow cell.

FIG. 33 illustrates the generation of the upper and lower sideband signals from the I,Q signal pair. An I(n) signal 326 and a Q(n) signal 328 are each processed by the Hilbert Transform operator, applied in steps 234 and 236. Those skilled in the art will recognize that this operator delays the input signal by π/2 radians (90 degrees). Note that the phase rotation is not a time delay, because the rotation is π/2, independent of the frequency of the incoming signal, over a broad range of frequencies. However, a time delay is inherent in the Hilbert Transform algorithm, and must be matched by time delays 238 and 240. The final stage of the sideband separation is that of summing at node 242 the rotated Q(n) signal with the unrotated I(n) signal to generate an upper sideband signal, USB(n) 330, and of summing at node 244 the rotated I(n) signal with the unrotated Q(n) signal to generate a lower sideband signal, LSB(n) 332. Summation at node 242 cancels signal vectors rotating counterclockwise in I,Q plane 286 (see FIG. 29) and reinforces those rotating clockwise in the I,Q plane. Summation at node 244 cancels signal vectors rotating clockwise in I,Q plane 286 and reinforces those rotating counterclockwise in the I,Q plane. The upper and lower sideband signals are used by the supervisor program during system start-up to search for the photodetector frequency and to set the local oscillator frequency for the baseband demodulator.

The I,Q complex signal is also applied to the pipeline process in a block 316 (see FIG. 32), which detects and segments signals from individual objects in the flow stream, tests these signals against predetermined acceptance criteria, and computes the object velocity from the accepted signals. The details of the steps implemented in block 316 are shown in FIG. 34.

The signal threshold concept illustrated in graph 302 (FIG. 31A) is used to segment the signal stream into sample packets, each of which represents an object or an aggregate of objects in the flow stream. The most accurate velocity measurements are those derived from the signals from isolated single objects. Signals from aggregate objects, i.e., signals from multiple objects coexisting in the FOV of the velocity detector, carry phase errors caused by the interference among the signals from the individual objects. The segmentation then accepts only those signals with an envelope width close to that predicted for a single object passing through the FOV at the current expected velocity. Because the envelope width is inversely proportional to velocity, the supervisor program tracks the known velocity and corrects the width limits as the velocity changes.

Referring to FIG. 34, each base pair of the I,Q complex signal is analyzed starting in a block 334. Segmentation of a packet begins when the magnitude of the signal crosses a threshold 371 while rising, detected in an step 336, and ends with the magnitude falls back across threshold 371, detected in a step 342. The sample count, n, and the unwrapped phase, $\Phi_m(n)$, are set to zero in a step 338 when the rising edge of the packet is detected. The unwrapped phase is computed in a step 344 for each sample following the rising edge, and the sample count is incremented each time a new sample is acquired in a step 340. Once the falling edge of the packet is detected, the sample count, n, is taken as a width 364 of the packet. The phase samples $\Phi_m(0)$ through $\Phi_m(n)$ are used in the computation of the average frequency of the signal packet, and, subsequently, the velocity of the object.

However, each packet must meet two criteria before being accepted as a useful signal. First, the packet width is compared to upper and lower width limits 366 in a step 346. The packet is rejected if the width falls outside those limits. The radial fractional frequency, ω(n), is computed for each sample within the packet in a step 348. The unwrapping algorithm cannot deliver values outside of the range from –π to π, since the Nyquist limits are –π and π radians/sample. Division by π in operation 348 expresses ω(n) as the dimensionless fraction of the Nyquist limit. The variance is computed for the ensemble of values ω(1) through ω(n) in a step 350 and compared with a maximum limit 373 in a step 360. This limit is a constant determined empirically for delivery of the required accuracy in the velocity measurements while limiting the number of rejected objects.

If the wave packet is accepted as representing a single object and as having an acceptably low frequency variance, an object velocity 368 is computed in a step 362 as follows:

$$\bar{f}_{bb} = \frac{\sum_{i=1}^{n} \omega(i)}{n} \cdot f_{Nyq}$$

and $$v_o(\text{mm/sec}) = (\bar{f}_{bb} + f_{LO}) \cdot s$$

where:
ω(i)=fractional frequency for sample i
$f_{Nyq}$=Nyquist frequency for baseband
$\bar{f}_{bb}$=mean baseband frequency (Hz)
$f_{LO}$=local oscillator frequency (Hz)
s=grating pitch (mm)
$v_o$=particle velocity (mm/sec).

In FIG. 35A, a graph 370 represents a plot of the baseband frequency versus time for the magnitude signal shown in graph 302 (FIG. 31A), but with only the qualified signals retained. A graph 372 in FIG. 35B shows the series of object velocities computed in operation 362 (see FIG. 34) from the baseband frequency data shown in graph 370.

For each accepted object, a velocity, $v_o$, is delivered to a scrolling object velocity list 318 of FIG. 32. Every time a new velocity value is added to the scrolling list, the oldest value is removed from the list. A running average computation in a step 320 constantly determines a running average 324 of the values in the scrolling velocity list at a repetition rate determined by the supervisor program.

FIG. 36 shows the structure of the supervisor program for the third embodiment of the present invention. Operation of the velocity detection system is initiated with the instrument calibration in a step 374, in which the noise from the photodetector channel is determined and analyzed in the absence of an optical signal. This step can be accomplished by turning off the light sources in the system or stopping the flow of objects through the flow tube. The purpose of the noise measurement is to establish a reference against which the information bearing signal will be compared for setting a threshold for accepting or rejecting phase samples.

The calibration operation measures the noise level at a plurality of amplifier gain settings and stores these measurements in a table 376 of noise level vs. gain. Table 376 will be used to select an initial gain setting for variable gain amplifier 52. As the amplifier gain is varied to regulate the signal strength during normal operation, the correct noise level for setting the decision threshold will be read from table 376 and applied to a threshold calculation in a step 378. Once the calibration operation has been completed, the light source or sources are turned on, and objects are introduced into the flow stream for image acquisition, as shown in a step 380.

The next task of the supervisor program shown in a step 382, is to search the spectrum for the photodetector signal. In the absence of any a priori knowledge of the flow speed, this initial search must span the entire range of frequencies in the spectrum, and may entail sweeping the spectrum a number of times until a strong signal is found. Step 382 sweeps the frequency of the local oscillator and captures a short time segment of upper sideband 330 and lower sideband 332 signals (see FIG. 33). As the local oscillator is swept across the actual frequency of the photodetector signal, the lower sideband amplitude will increase and then drop. Then the upper sideband amplitude will increase and then drop. For the broad sweep to locate the approximate photodetector frequency, the local oscillator is varied in large increments to speed the search, and the search in step 382 measures the root mean square (rms) sum of the sidebands as follows:

$$P_{usb} = \sum_{i=1}^{N} U^2[i]$$

$$P_{lsb} = \sum_{i=1}^{N} L^2[i]$$

$$P_{sum} = \sqrt{P_{usb}^2 + P_{lsb}^2}$$

where:
U[i]=upper sideband amplitude of ith sample
L[i]=lower sideband amplitude of ith sample
N=number of time samples in tested signal segment
$P_{sum}$=integrated sideband power for signal segment.

FIG. 37 is a graph 406 of the integrated sideband power versus the local oscillator frequency for the broad search sweep. The width of a power envelope 408 is two times the bandwidth of lowpass filters 230 and 232 (see FIG. 25) in the baseband demodulator. The desired local oscillator frequency is located at a dip 410 between the two peaks in the power envelope. However, this frequency is poorly resolved because of the large steps used in search sweep 382.

Referring back to FIG. 36, a more accurate estimate of the desired local oscillator frequency is made in a step 384 by varying the local oscillator frequency over a narrow range covering the power envelope. This narrow sweep is illustrated by a graph 414 in FIG. 38, which is an overlay of an upper sideband power 416, called $P_{usb}$, and a lower sideband power 418, called $P_{lsb}$, as a function of local oscillator frequency. The search in step 384 of FIG. 36 finds a frequency 420 in FIG. 38 at which the upper sideband and lower sideband are of equal power. As will be evident in FIG. 38, this frequency is approximately 2500 Hz. Under this condition, the local oscillator frequency is approximately equal to the photodetector signal center frequency, and the baseband demodulation system can be used to measure the exact photodetector signal frequency.

With the magnitude threshold and the local oscillator frequency set, object processing can commence. During object processing, the supervisor program continuously monitors the sideband signals in a step 388 (FIG. 36) using sample locations accepted by signal processing step 316 (see FIG. 32). The selected sideband samples are used to monitor the balance between the power in the upper sideband signal and that in the lower sideband signal. Imbalance between the two sideband signals indicates that the photodetector frequency has shifted and that the local oscillator frequency should be adjusted. The sideband balance will be repeatedly computed in a step 388, the balance values stored in a table 390, adjustments to the local oscillator will be computed in a step 394, and applied in a step 386. The number of values maintained in table 390 can be modified to adjust the response time and stability of the local oscillator feedback loop.

The sideband signal levels are checked to determine if they have been lost in a step 392. If both the upper sideband and lower sideband signals are lost, the supervisor program interrupts signal processing and returns to search routine 382 to tune the system back to the photodetector signal frequency, if possible. The supervisor program will remain in the search mode until a signal is acquired or the velocity detection system is turned off.

The gain of the variable gain amplifier is regulated during system operation as well, in order to optimize the SNR of the velocity detector as specimen characteristics change. The amplifier gain regulation system of the supervisor program implemented in a step 396 creates the histogram of the peak magnitudes of the accepted signal packets. A step 398 provides for counting a number of samples occupying a predetermined number of levels near the top of the analog-to-digital converter output scale, and maintains a list of the most recent count results in a table 400. That table is analyzed to determine a gain adjustment in a step 402. The gain adjustment implemented in step 402 will use a "fast attack," "slow recovery" algorithm, as described above, to regulate the gain of the variable gain amplifier.

The new gain setting is set in a step 404 and is provided to a noise calibration table 376. The response time and stability of the gain control feedback loop can be modified by adjusting the number of samples maintained in table 400 and analyzed in step 402.

TDVM of Objects Using Paired Non-uniform Optical Gratings

In the fourth preferred embodiment of the present invention, the light collected for velocity measurement is modulated by two optical gratings and sensed by two photodetectors, as shown in FIG. 43. The velocity is measured by cross-correlating the signal from the first photodetector with that from the second photodetector, yielding a time-of-flight value that is converted into a velocity of the object.

The cross-correlation of two signals is carried out by convolving the two signals and extracting information from the output of the convolution operation, which is called the correlogram. The convolution in the time domain is defined by the following equation:

$$f_1(t)*f_2(t) = \int_{-\infty}^{\infty} f_1(\lambda) f_2(t-\lambda) d\lambda.$$

The value of the convolution for every time sample, t, is the sum over infinity of the product of the two functions, but with the second function offset by time t. The utility of the convolution operator lies in the fact that it is equivalent to multiplication in the frequency domain:

Given the general notation:

$$F(e^{j\omega}) = \text{the Fourier Transform of } f(t)$$

if $$f_3(t) = f_1(t) * f_2(t)$$

then $$F_3(e^{j\omega}) = F_1(e^{j\omega}) \cdot F_2(e^{j\omega}).$$

A filter with a desired frequency response $H(e^{j\omega})$ can be implemented as a time domain operation, for example, by applying its inverse Fourier Transform, h(t), in the convolution integral. In the present invention, however, the utility of the convolution operator is in the measurement of the time delay between two signals. In the simplest case, the two signals are identical to one another, except that the second signal is delayed by time $t_0$. As shown in the following equations, applying time delay to a signal is equivalent to convolving that signal by the delayed impulse function, $\delta(t-t_0)$:

$$f_2(t)=f_1(t-t_0)$$

then $$f_2(t)=f_1(t)*\delta(t-t_0).$$

Because convolution is associative, the problem of convolving the first signal $f_1(t)$ with the second signal, $f_2(t)$, can be solved by convolving $f_1(t)$ with itself and time delaying the result. Thus, $$f_1(t)*f_2(t)=f_1(t)*f_1(t)*\delta(t-t_0)$$

if $$f_3(t)=f_1(t)*f_1(t)$$

then $$f_1(t)*f_2(t)=f_3(t-t_0).$$

Conversely, it is possible to measure the time delay between two signals by convolving one with the other and detecting the amount of time delay in the result.

FIG. 39 illustrates the convolution of two similar signals 422 and 424, which are the inputs of a convolution operator 426 arriving at different times. A correlogram 428 is a plot of the amplitude of the integrated product of signals 422 and 424. The horizontal axis of the correlogram represents the time delay applied to signal 422 relative to signal 424 using the convolution operation, scaled in units of time samples. A delay of around 400 samples is required to align signal 422 with signal 424, which is evident from the peak value of the correlogram amplitude. Note that the correlogram is broader than either of the two signals. This condition can be understood from the recognition that convolving a signal with itself is equivalent to squaring the spectrum of the signal, a step that compresses the spectral distribution. Narrowing the bandwidth of a signal broadens the signal in the time domain.

In the velocity detection system, the signals 422 and 424 might have been generated by two objects traversing an optical grating 432, as shown in FIG. 40. A graph 430 represents the Gaussian illumination profile applied to the field of optical grating 432. An object traversing the illumination profile will generate a signal with a Gaussian envelope and an oscillation frequency directly proportional to the velocity of the object and inversely proportional to the optical grating pitch.

Detecting the peak of correlogram 428 might be accomplished using a simple peak detector. The correlogram is broad, however, and the peak of the envelope might not coincide with the peak of an oscillation cycle. More elaborate detection schemes might improve the accuracy, but it is also useful to generate a narrower correlogram with a more clearly defined peak. This objective is accomplished by using an optical grating 436 shown in FIG. 41. Optical grating 436 has a non-uniform pitch, with line width (opaque and transparent bar width) decreasing linearly from the left end of the optical grating to the right end of the optical grating. The optical grating is aligned with a beam profile 434. Graphs 438 and 440 in FIG. 42 represent signals that could be generated by photodetectors in response to the light from two objects passing through optical grating 436. A resulting correlogram 442 is more compact than correlogram 428, suggesting that the time delay value might be extracted more easily from correlogram 442 than from correlogram 428.

The preferred embodiment of the correlation-based signal generation system uses a detection system that takes advantage of the non-uniform optical grating pitch. FIG. 43 illustrates the components used in the preferred embodiment. Light source 12 and lens 36 illuminate the FOV of flow tube 16 for the purpose of velocity measurement. The optical system comprising lenses 40, 44, and 78 and beam splitter 76 form images of the objects passing through the FOVs on two optical gratings 444 and 446 having non-uniform but identical patterns of opaque and transparent bars.

As shown in FIG. 44, images 450 and 452 of optical gratings 444 and 446 are aligned end-to-end along the axis of flow. The boundary between the two images is aligned with the midpoint of an illumination profile 454. Light scattered or emitted by objects in the flow stream is modulated by optical gratings 444 and 446 and the modulated light is delivered to photodetectors 50 and 50a by lens 48 and a lens 448, respectively (see FIG. 43).

FIG. 45 illustrates the performance of the correlation operation for signals generated using the optical grating geometry shown in FIG. 44. A signal 456, produced in response to light modulated by optical grating 444 at the upstream side of the illumination field, grows in amplitude and increases in frequency with time, and terminates when the object moves into the field of downstream side of the illumination field. A signal 458, produced in response to light modulated by optical grating 446 at the downstream side of the illumination field, starts at high amplitude and low frequency. The amplitude decays with time as the frequency increases. A correlogram 460 shows a very distinct peak at the exact delay value that brings the two signals into alignment.

FIG. 46 shows an expanded view 462 of correlogram 460. For this view, the delay limits of the cross-correlation operation 426 were expanded to show that as the delay of signal 458 approaches the delay for optimal alignment, it first passes through a region 466 in which the correlogram appears very noisy. This region is where the high-amplitude part of signal 456 is aligned with the high-amplitude part of signal 458. However, the particular optical grating configuration shown in FIG. 44 provides the benefit that a primary peak 464 of correlogram 460 is bordered on both sides by very low-level signals 468. The noisy region of the expanded correlogram is avoided by using only those delay values close to the actual time of flight of the objects from a location on the upstream grating to the corresponding location on the downstream grating. A feedback loop in the supervisor program is used to regulate the convolution time delay limits to maintain this condition.

FIG. 47 shows the functional processing blocks used for the signal acquisition and processing for this embodiment of the present invention. The signals respectively. The outputs of the amplifiers are applied to bandpass filters 54 and 54a to eliminate DC bias and to prevent aliasing when the signals are sampled by ADCs 56 and 56a. The digital outputs of the ADCs are delivered to a signal processing stage 470, which accepts a signal segment of a predetermined length and delivers an estimate of the object velocity to a scrolling velocity list 472, if acceptable signals from objects traversing the flow cell are present in that segment. If a new velocity value is delivered by the signal processing operation, it is added to list 472 and the oldest value on the list is deleted. A step 474 delivers the average of the velocity values in list 472 at the rate at which signal segments are captured in the signal processor to facilitate computation of a running average 476.

FIG. 48 shows the detailed architecture of the signal processing operation. For every cycle interval of the signal processor, concurrent segments of the digitized signals from photodetectors 50 and 50a are captured in steps 478a and 478b. The captured segments are simultaneously applied to magnitude calculators 480a and 480b, and to a step 482, which provides for determining a cross-correlation. Each magnitude calculator uses the following algorithm for computing the signal level:

$$M_j = \sum_{i=1}^{N} |A[i]|$$

where:

N=length of the signal segment

A[i]=value of the ith sample of the segment $M_j$=magnitude of the jth signal segment.

The magnitude values are sent to supervisor program 486 to be used to regulate the photodetector amplifier gain.

The convolution (or cross-correlation) carried out in step 482 generates the correlogram using the following algorithm:

```
for (k=Min_Delay; k<=Max_Delay; k++)
{
  m=k–Min_Delay;
  for (i=0; i<=Correlation_Length; i++
  {
    j=k+i;
    C[m]+=Signal 1[i]* Signal 2[j];
  }
}
```

FIG. 49 illustrates the results of the correlation algorithm. A signal segment 496 from the first photodetector is convolved with a signal segment 498 from the second photodetector through a series of multi-and-accumulate operations to generate a correlogram 508. For each value in correlogram 508, the first P samples, where P=Correlation Length, of signal 496 are multiplied by the corresponding samples of signal 498 from sample Q, where Q=Delay, to sample R, where R=Delay+Correlation Length. The products of the sample-by-sample multiplication are summed to produce the values of the correlogram. The Delay value begins at a Min_Delay 504 and advances one sample for every sample in correlogram 508 until it reaches a Max_Delay 506.

The location of the peak of the correlogram is found in a step 484 (see FIG. 48) using a simple peak detection algorithm, as follows:

$C_{pk}=0$ for (d=1=>d=N)
if (C[d]>$C_{pk}$)
then $[(C_{pk}=C[d])$ and $(N_d=d)]$ where:

C[d]=value of correlogram at delay d $N_d$=location of correlogram peak $C_{pk}$=peak amplitude of correlogram.

In a step 488, the peak amplitude of the correlogram is compared to a threshold. This threshold is a fixed value accessible to a supervisor program 486. Regulation of the photodetector signal level using variable gain amplifiers 52 and 52a enable the use of a fixed threshold.

If the peak amplitude of the correlogram exceeds the threshold, the peak location from step 484 is accepted and passed to a step 490 in which the velocity is calculated. The velocity calculated in step 490 then replaces the oldest velocity value in scrolling velocity list 472 (see FIG. 47). If the amplitude of the correlogram is less than or equal to the threshold, the signal processor returns a NULL value 494, and scrolling velocity list 472 remains unchanged.

For a valid correlogram, a velocity 492 is computed from the correlogram peak location using the following relation:

$$t_t = N_d \cdot t_{samp}$$

and $$v = s/t_t$$

where:

$t_t$=transit time, grating-to-grating (sec)

$t_{samp}$=signal sample time s=grating-to-grating distance (mm)

v=velocity (mm/sec).

The running average velocity estimate is acquired by the supervisor program and translated into a frequency signal used by Instrument Timing Generator 146, as shown in FIG. 19.

FIG. 50 shows the structure of the supervisor program for the fourth embodiment of the present invention. System operation is initiated in a start block 510 when the gain of the variable gain amplifier is set to nominal values, and objects are introduced into the flow stream for image acquisition.

In a step 512, the supervisor program performs a cross-correlation between segments of the two photodetector signals using a wide span of correlation delays. The delay value yielding the largest peak in the correlogram is used in a step 514 to compute the initial velocity. The cross-correlation delay limits are set in a step 516 to bracket this initial delay value.

With the cross-correlation delay limits set, object velocity processing commences. During this processing, the supervisor program continuously measures the velocity using the cross correlation method and adjusts the correlation delay limits to maintain execution of a short span cross-correlation in the neighborhood of the delay required for the current flow velocity. Use of the short span cross correlation reduces computation time.

A step 478a provides for capturing the photodetector signal segments; a step 482, computes the short delay span cross-correlation; a step 490 computes the velocity and tabulates the results in a scrolling velocity list 472 to provide the information for adjusting the correlation limits. The limits are determined in a step 518 from the average of the values in velocity table 472. This average velocity is converted to an expected correlation time delay value, and the limits are placed symmetrically around this expected delay. The offset from the expected value to the minimum delay and the offset from the expected value to the maximum delay are empirically determined and stored in a look-up table to be used in the limit calculation step 518. In a step 516, the correlation offset limits are set and stored in locations accessible to the cross-correlation determination in step 482 for use in processing the next segment of the photodetector signals.

The supervisor program also continuously optimizes the gain of the variable gain amplifiers to maximize SNR as specimen characteristics change, without causing saturation at the ADC. The process of regulating the gains of the amplifiers is initiated in steps 480a and 480b, which compute the integrated magnitudes of the signal segments. The magnitudes are delivered to tables 520 and 526, which contain a set of the most recent magnitudes. Adjustments to the gains are computed by steps 522 and 528 from the maximum magnitudes in tables 520 and 526 and the new setting to variable gain amplifiers 52 and 52a are made in steps 524 and 530. The gain adjustment in steps 524 and 530 uses a "fast attack," "slow recovery" algorithm as described above, to regulate the gain of the variable gain amplifiers.

It should be noted that the method described above for processing the electrical signals produced by the photodetector(s) in the third and fourth embodiments using the TDVMs can also be applied to determining the velocity of objects disposed on a substrate (and the velocity of the substrate) that is caused to move through the FOV. Generally, either the TDVM or the FDVM approach can be used for determining the velocity of any configuration of objects moving through the FOV.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A velocity measurement system for determining an indication of a velocity of an object passing through a field of view, comprising:
    (a) an optical element disposed to direct light traveling from an object passing through the field of view along a collection path;
    (b) at least one optical grating of substantially uniform pitch disposed in the collection path, said at least one optical grating modulating the light traveling along the collection path to produce modulated light having a modulation frequency proportional to a velocity of an object passing through the field of view;
    (c) at least one light sensitive detector on which the modulated light is incident, said at least one light sensitive detector producing an electrical signal responsive to the modulated light;
    (d) means for processing the electrical signal in the time domain to determine the indication of the velocity.

2. The measurement system of claim 1, wherein a pitch of the optical grating is varied to compensate for distortion due to the optical element.

3. A velocity measurement system for determining an indication of a velocity of an object passing through a field of view, comprising:
    (a) an optical element disposed so that light traveling from an object passing through the field of view is directed along a collection path;
    (b) an optical grating disposed in the collection path, said optical grating modulating the light traveling along the collection path, to produce modulated light having a modulation frequency corresponding to a velocity of an object passing through the field of view;
    (c) a light sensitive detector disposed to receive the modulated light, said light sensitive detector responding to the modulated light by producing a corresponding electrical signal;
    (d) means coupled to said light sensitive detector, for converting the electrical signal into a sequence of digital samples; and
    (e) means in receipt of the sequence of digital samples, for processing the sequence of digital samples in the time domain to determine the indication of the velocity of an object.

4. The measurement system of claim 3, wherein said means for converting the electrical signal into a sequence of digital samples comprises an analog-to-digital converter.

5. The measurement system of claim 3, further comprising an amplifier coupled to said light sensitive detector, for amplifying the electrical signal before it is converted into the sequence of digital samples.

6. The measurement system of claim 3, further comprising a bandpass filter coupled to the light sensitive detector, for filtering the electrical signal before it is converted into the sequence of digital samples.

7. The measurement system of claim 3, wherein said means for processing the sequence of digital samples comprises at least one of a programmed computing device, an application specific integrated circuit, and a digital oscilloscope.

8. The measurement system of claim 3, further comprising a system controller that is coupled to and controls the means for converting the electrical signal into the sequence of digital samples, and the means for processing the sequence of digital samples, said system controller comprising at least one of a programmed computing device and an application specific integrated circuit.

9. The measurement system of claim 8, wherein said system controller includes means for performing at least one of the following functions:
    (a) regulating an amplitude of said electrical signal;
    (b) determining a signal-to-noise ratio of the electrical signal and rejecting any indication of the velocity determined if the signal-to-noise ratio is less than a predetermined threshold; and
    (c) regulating a local oscillation frequency employed by the means for processing in response to variations in the indication of the velocity of an object that is determined.

10. The measurement system of claim 3 in which the light from an object passing through the field of view comprises at least one of light scattered by an object, an unstimulated emission from an object, and a stimulated emission from an object.

11. The measurement system of claim 3, wherein said optical grating comprises an optical grating having a substantially uniform pitch, and wherein said means for converting the electrical signal into a sequence of digital samples comprises:
    (a) an amplifier having an input that is coupled to said light sensitive detector and an output, said amplifier amplifying the electrical signal, produces an amplified electrical signal at its output;
    (b) a bandpass filter coupled to the output of the amplifier, said bandpass filter filtering the amplified electrical signal to produce a passband signal; and (c) a first analog baseband converter and analog-to-digital converter that converts the passband signal to a first sequence of digital samples, such that the first sequence of digital samples represents a real part of the electrical signal; and (d) a second analog baseband converter and analog-to-digital converter that converts the passband signal to a second sequence of digital samples, such that the second sequence of digital samples represents an imaginary part of the electrical signal.

12. The measurement system of claim 3, wherein said optical grating has a uniform pitch, and wherein said means for processing the sequence of digital samples determines the indication of the velocity from a first derivative of a time series of phase samples of the electrical signal, after calculating those phase samples from a baseband complex representation of the electrical signal.

13. The measurement system of claim 3, wherein said optical grating has a non uniform pitch.

14. The measurement system of claim 13, wherein said optical grating comprises a plurality of alternating opaque bars and transparent gaps, widths of which vary in a linear progression in a direction perpendicular to a longitudinal extent of the plurality of alternating opaque bars and transparent gaps.

15. The measurement system of claim 13, wherein said optical grating comprises a plurality of alternating opaque bars and transparent gaps, widths of which vary in a non-linear pattern in a direction perpendicular to a longitudinal extent of the plurality of alternating opaque bars and transparent gaps.

16. The measurement system of claim 13, wherein said optical grating comprises two substantially identical sections, each section having a non-uniform pattern of bar and gap widths, disposed along an axis of motion of an object, such that an object traverses said sections sequentially.

17. The measurement system of claim 13, further comprising:
(a) a beam splitter that is disposed in the collection path, such that a portion of the light traveling from an object along the collection path is diverted along a second collection path;
(b) another optical grating disposed in the second collection path, said other optical grating having a non uniform pitch and modulating the light traveling along the second collection path, to produce modulated light having a modulation frequency corresponding to a velocity of an object passing through the field of view; and
(c) another light sensitive detector disposed in the second collection path, said other light sensitive detector converting the modulated light from said at least one other optical grating into a second electrical signal.

18. The measurement system of claim 17, wherein said means for converting the electrical signal into a sequence of digital samples comprises:
(a) a first amplifier having an input that is coupled to said at least one light sensitive detector disposed in the collection path to receive the electrical signal, and an output, said first amplifier amplifying the electrical signal, producing an amplified electrical signal at its output;
(b) a first bandpass filter coupled to the output of the first amplifier, said first bandpass filter filtering the amplified electrical signal to produce a passband signal;
(c) a first analog-to-digital converter that converts the passband signal to a first sequence of digital samples;
(d) a second amplifier having an input that is coupled to said other light sensitive detector disposed in the second collection path, and an output, said second amplifier amplifying the second electrical signal, producing a second amplified electrical signal at its output;
(e) a second bandpass filter coupled to the output of the second amplifier, said second bandpass filter filtering the second amplified electrical signal to produce a second passband signal; and
(f) a second analog-to-digital converter that converts the second passband signal to a second sequence of digital samples.

19. The measurement system of claim 17, wherein said means for converting the electrical signal into a sequence of digital samples comprises:
(a) a first amplifier having an input that is coupled to said light sensitive detector disposed in the collection path, and an output, said first amplifier amplifying the electrical signal, producing an amplified electrical signal at its output;
(b) a first analog-to-digital converter that converts the amplified electrical signal to a first sequence of digital samples;
(c) a first digital bandpass filter for rejecting a direct current bias and a high frequency noise component from the first sequence of digital samples;
(d) a second amplifier having an input that is coupled to said other light sensitive detector disposed in the second collection path, and an output, said second amplifier amplifying the second electrical signal, producing a second amplified electrical signal at its output;
(e) a second analog-to-digital converter that converts the second amplified electrical signal to a second sequence of digital samples; and
(f) a second digital bandpass filter for rejecting a direct current bias and a high frequency noise component from the second sequence of digital samples.

20. The measurement system of claim 17, wherein each optical grating is aligned in series along an axis of motion of an object, and wherein said means for processing the sequence of digital samples to determine the indication of the velocity of an object calculates an amplitude peak of a cross-correlogram generated by a convolution of the electrical signal from said light sensitive detector disposed in the collection path with the second electrical signal from said other light sensitive detector disposed in the second collection path.

21. The measurement system of claim 17, further comprising a control system controllably connected to said means for converting the electrical signal into a sequence of digital samples and said means for processing the sequence of digital samples.

22. The measurement system of claim 21, wherein said control system regulates:
(a) a gain of the first amplifier and the second amplifier in response to varying levels of the electrical signal and the second electrical signal, respectively; and
(b) an upper and a lower limit of time shifting in a cross-correlation operation in response to variations in the velocity of an object.

23. The measurement system of claim 3, further comprising at least one light source for illuminating the field of view.

24. The measurement system of claim 23, wherein said at least one light source is disposed to provide an incident light that illuminates an object passing through the field of view.

25. The measurement system of claim 24, wherein said incident light stimulates at least one of an emission and a fluorescence from an object passing through the field of view, and the light from the object passing through the field of view comprises one of an emitted light and a fluoresced light.

26. The measurement system of claim 24, wherein the incident light is at least partially absorbed by an object passing through the field of view, so that the light from an object has been changed due to the absorption by an object.

27. The measurement system of claim 24, wherein the light is reflected from an object passing through the field of view toward the optical element.

28. The measurement system of claim 23, wherein the light source comprises at least one of a coherent light source, a non-coherent light source, a pulsed light source, a continuous light source, a continuous wave laser, a pulsed laser, a continuous wave incandescent lamp, a strobe arc lamp, and an optical filter that provides a limited spectrum of light for illuminating an object.

29. The measurement system of claim 3, further comprising a source of a reference field light, wherein an intensity of the light from an object passing through the field of view is modulated by a phase interference with the reference field light.

30. The measurement system of claim 3, wherein a flow of a fluid in which objects are entrained passes through the field of view, such that an indication of a velocity of an object entrained in the fluid is determined by the means for processing.

31. The measurement system of claim 3, wherein a support on which a plurality of objects are disposed passes through the field of view, such that an indication of a velocity of an object on the support and thus, of the support, is determined by the means for processing.

32. The measurement system of claim 3, wherein said optical element comprises a lens.

33. The measurement system of claim 3, wherein the other light sensitive detector and a dispersing element that directs the light from the optical element to each of the light sensitive detectors.

34. The measurement system of claim 33, wherein the other light sensitive detector is employed to determine a characteristic of an object passing through the field of view, other than an indication of a velocity of an object.

35. The measurement system of claim 3, wherein an object passes through another field of view, further comprising:
(a) another optical element disposed to direct light from an object passing through the other field of view along another collection path; and
(b) another light sensitive detector disposed to receive the light traveling along the other collection path and employed to determine a characteristic of an object passing through the other field of view, said characteristic being other than the indication of the velocity of an object.

36. The measurement system of claim 3, further comprising means disposed downstream from said field of view, for sorting objects.

37. The measurement system of claim 3, wherein said light sensitive detector comprises one of a photosensitive diode and a photomultiplier tube.

38. The measurement system of claim 3, further comprising a fluid supply disposed upstream of the field of view, said fluid supply providing the field of view with a flow of a fluid in which a plurality of objects are entrained.

39. The measurement system of claim 38, wherein each of the plurality of objects comprises one of a biological cell and a particulate component of a biological specimen.

40. The measurement system of claim 3, further comprising a solid support on which a plurality of objects are disposed, and a prime mover, said solid support being moved through the field of view by the prime mover.

41. An optical analysis system employed to determine an indication of a velocity of a relative movement between an object and the optical analysis system, and to determine at least one additional characteristic of the object, comprising:
(a) a first optical element disposed to direct light from an object along a first collection path;
(b) a second optical element disposed in the first collection path to direct a portion of the light traveling along the first collection path, along a second collection path;
(c) an optical grating disposed in the second collection path, said optical grating modulating the light traveling along the second collection path, producing modulated light that has a modulation frequency corresponding to a velocity of the relative movement between the object and the optical analysis system;
(d) a light sensitive detector disposed in the second collection path to receive the modulated light, said at least one light sensitive detector producing an electrical signal in response to the modulated light;
(e) means coupled to the light sensitive detector to receive the electrical signal, for determining the indication of the velocity of the relative movement between the object and the optical analysis system as a function of the electrical signal and producing a timing signal as a function of said indication of the velocity;
(f) a time delay integration (TDI) detector disposed to receive light traveling along the first collection path, said TDI detector being coupled to said means for determining the indication of the velocity, said TDI detector employing the timing signal to produce an output signal that is indicative of said at least one additional characteristic of the object.

42. The optical analysis system of claim 41, further comprising a control that is coupled to and controls the means for determining the indication of the velocity, and the TDI detector.

43. The optical analysis system of claim 41, wherein said optical grating has a substantially uniform pitch.

44. The optical analysis system of claim 43, wherein said means for determining the indication of the velocity of the relative movement between the object and the optical analysis system comprises:
(a) an amplifier having an input that is coupled to the light sensitive detector disposed in the second collector path and an output, said amplifier amplifying the electrical signal, producing an amplified electrical signal at its output;
(b) an analog-to-digital converter that converts the amplified electrical signal to a sequence of digital samples; and
(c) processing means for processing the sequence of digital samples to determine the indication of the velocity of the object.

45. The optical analysis system of claim 43, wherein said means for determining the indication of the velocity of the relative movement between the object and the optical analysis system comprises:
(a) an amplifier having an input that is coupled to the light sensitive detector disposed in the second collector path and an output, said amplifier amplifying the electrical signal, producing an amplified electrical signal at its output;
(b) a bandpass filter coupled to the output of the amplifier, said bandpass filter filtering the amplified electrical signal to produce a passband signal; and
(c) a first analog baseband converter and analog-to-digital converter that converts the passband signal to a first sequence of digital samples, such that the first sequence of digital samples represents a real part of the electrical signal, and
(d) a second analog baseband converter and analog-to-digital converter that converts a portion of the passband signal into a second sequence of digital samples, such that the second sequence of digital samples represents an imaginary part of the electrical signal, and
(e) processing means for processing the first and second sequences of digital samples to determine the indication of the velocity of the relative movement between the object and the optical analysis system.

46. The optical analysis system of claim 44, wherein said processing means calculates a time series of phase samples from a baseband complex representation that is derived from the sequence of digital samples.

47. The optical analysis system of claim 41, wherein said optical grating disposed in the second collection path has a substantially non uniform pitch.

48. The optical system of claim 47, wherein said optical grating disposed in the second collection path comprises at least one of:
(a) a plurality of alternating opaque bars and transparent gaps, widths of which vary in a linear progression in a direction perpendicular to a longitudinal extent of the plurality of alternating opaque bars and transparent gaps; and
(b) a plurality of alternating opaque bars and transparent gaps, widths of which vary in a non-linear pattern in a direction perpendicular to a longitudinal extent of the plurality of alternating opaque bars and transparent gaps.

49. The optical analysis system of claim 47, wherein the optical grating disposed in the second collection path and having the substantially non uniform pitch comprises two substantially identical sections, each having a non-uniform pattern of bar and gap widths and disposed along an axis of motion of light from the object such that the light from the object traverses said sections sequentially.

50. The optical analysis system of claim 47, further comprising:
(a) a third optical element disposed in the second collection path, such that a portion of the light traveling from the object along the second collection path is diverted along a third collection path;
(b) an optical grating disposed in the third collection path and having a substantially non uniform pitch, said optical grating modulating the light, to produce modulated light having a modulation frequency corresponding to the velocity of the object passing through the field of view; and
(c) a light sensitive detector disposed in the third collection path and used to convert the modulated light traveling along the third collection path into a second electrical signal, said light sensitive detector being coupled to provide the second electrical signal to said means for determining the indication of the velocity of the relative movement between the object and the optical analysis system.

51. The optical analysis system of claim 50, wherein said means for determining the indication of the velocity of the relative movement between the object and the optical analysis system comprises:
(a) a first amplifier having an input that is coupled to the light sensitive detector disposed in the second collection path, and an output, said first amplifier amplifying the electrical signal, producing an amplified electrical signal at its output;
(b) a first bandpass filter coupled to the output of the first amplifier, said first bandpass filter filtering the amplified electrical signal provided by the first amplifier to produce a passband signal;
(c) a first analog-to-digital converter that converts the passband signal to a first sequence of digital samples;
(d) a second amplifier having an input that is coupled to the light sensitive detector disposed in the third collection path, and an output, said second amplifier amplifying the second electrical signal, producing a second amplified electrical signal at its output;
(e) a second bandpass filter coupled to the output of the second amplifier, said second bandpass filter filtering the second amplified electrical signal to produce a second passband signal;
(f) a second analog-to-digital converter that converts the second passband signal to a second sequence of digital samples; and
(g) processing means for processing each sequence of digital samples, to determine the indication of the velocity of the relative movement between the object and the optical analysis system.

52. The optical analysis system of claim 50, wherein said means for determining the indication of the velocity of the relative movement between the object and the optical analysis system comprises:
(a) a first amplifier having an input that is coupled to the light sensitive detector disposed in the second collection path, and an output, said first amplifier amplifying the electrical signal, producing a first amplified electrical signal at its output;
(b) a first analog-to-digital converter that converts the first amplified electrical signal to a first sequence of digital samples;
(c) a first digital bandpass filter for rejecting a direct current bias and a high frequency noise component from the first sequence of digital samples;
(d) a second amplifier having an input that is coupled to the light sensitive detector disposed in the third collection path, and an output, said second amplifier amplifying the second electrical signal, producing a second amplified electrical signal at its output;
(e) a second analog-to-digital converter that converts the second amplified electrical signal to a second sequence of digital samples;
(f) a second digital bandpass filter for rejecting a direct current bias and a high frequency noise component from the second sequence of digital samples;
(g) processing means for processing each sequence of digital samples, to determine the indication of the velocity between the object and the optical analysis system.

53. The optical analysis system of claim 50, wherein said means for determining the indication of the velocity of the relative movement between the object and the optical analysis system determines an amplitude peak of a cross-correlogram generated by a convolution of the electrical signal from the light sensitive detector disposed in the second collection path with the second electrical signal from the light sensitive detector disposed in the third collection path, so that an image field associated with the optical grating disposed in the second collection path and a second image field associated with the optical grating disposed in the third collection path are aligned in series along an axis of the relative movement between the object and the optical analysis system.

54. The optical analysis system of claim 51, wherein said processing means comprises at least one of a digital oscilloscope, a programmed computing device, and an application specific integrated circuit.

55. The optical analysis system of claim 52, further comprising a control system controllably connected to each amplifier and to said processing means, said control system regulating an upper and a lower limit of a time shifting employed in determining a cross-correlation in response to variations in the velocity of the relative movement between the object and the optical analysis system.

56. An imaging system adapted to determine an indication of a velocity of a relative movement between the imaging system and an object, and at least one additional characteristic of the object, comprising:
   (a) an optical element disposed to direct light traveling from an object along a first collection path;
   (b) a beam splitter disposed in the first collection path so that a portion of the light traveling from the object along the first collection path is diverted along a second collection path;
   (c) an optical grating disposed in the second collection path, the optical grating modulating the collected light traveling along the second collection path, to produce modulated light having a modulation frequency corresponding to the velocity of the relative movement between the object and the imaging system;
   (d) a light sensitive detector disposed in the second collection path to receive the modulated light, said light sensitive detector producing an electrical signal in response to the modulated light received along the second collection path;
   (e) means coupled to the light sensitive detector, for determining the indication of the velocity of the relative movement between the object and the imaging system as a function of the electrical signal, said means producing a timing signal as a function of said indication of the velocity;
   (f) an imaging lens disposed in the first collection path, producing an image from the light traveling along the first collection path; and
   (g) a time delay integration (IDI) detector disposed in the first collection path to receive the image produced by the imaging lens, producing an output signal that is indicative of said at least one additional characteristic of the object, said TDI detector being coupled to the means for determining the indication of the velocity to receive the timing signal and producing the output signal by using the timing signal to provide a clocking function that synchronizes the TDI detector to a movement of the image of the object over the TDI detector so that a response to the light comprising the image is integrated over time as the image moves over the TDI detector.

57. An imaging system for determining an indication of a relative velocity and at least one additional characteristic of an object, from images of the object, while there is relative movement between the object and the imaging system, comprising:
   (a) a light source that emits light illuminating the object;
   (b) an optical element disposed to direct light from the object along a first collection path;
   (c) a first beam splitter disposed in the first collection path so that light scattered from the object is directed along a different path, while light that is emitted by the object continues through the beam splitter along the first collection path;
   (d) a second beam splitter disposed in the first collection path so that a portion of the light from the object traveling along the first collection path is diverted along a second collection path;
   (e) an optical grating disposed in the second collection path, said optical grating modulating the light traveling along the second collection path, to produce modulated light having a modulation frequency corresponding to the velocity of the relative movement between the object and the imaging system;
   (f) a light sensitive detector disposed to receive the modulated light, producing an electrical signal in response thereto;
   (g) means coupled to the light sensitive detector to receive the electrical signal, for determining the indication of the relative velocity between the object and the imaging system and producing a timing signal as a function of said indication of the relative velocity;
   (h) a spectral dispersing element disposed downstream of the second beam splitter in the first collection path, said spectral dispersing element spectrally dispersing the light emitted by the object, producing spectrally dispersed light;
   (i) an optical element disposed to receive the spectrally dispersed light, producing an image thereof;
   (j) a cylindrical lens disposed to receive the light scattered from the object, said cylindrical lens having a central axis around which the cylindrical lens is curved, said central axis being generally orthogonal to a direction of the relative movement between the object and the imaging system, so that the cylindrical lens produces a scattered pattern image of the object along a direction that is substantially parallel to said central axis of the cylindrical lens; and
   (k) at least one time delay integration (TDI) detector disposed to receive the image, producing an output signal that is indicative of at least one characteristic of the object, and to receive the scattered pattern image produced by the cylindrical lens, producing a different output signal that is indicative of at least one other characteristic of the object, said at least one TDI detector being coupled to the means for determining the indication of the relative velocity of the movement between the object and the imaging system, said at least one TDI detector producing said output signals by using the timing signal for synchronization of said output signals with movement of the image and the scattered pattern image over said at least one TDI detector.

58. An optical analysis system employed to determine an indication of a velocity of a relative movement between an object and the optical analysis system and to determine and at least one other characteristic of the object, comprising:
   (a) a first collection optical element disposed so that light from the object is directed along a first collection path;

(b) a first light dispersing optical element disposed in the first collection path so as to disperse the light traveling along the first collection path, producing first dispersed light;

(c) a first imaging optical element disposed to receive the first dispersed light, forming at least one image from the first dispersed light;

(d) a second collection optical element disposed to direct light from the object along a second collection path, different than the first collection path;

(e) a second light dispersing optical element disposed in the second collection path, so as to disperse the light traveling along the second collection path, producing second dispersed light;

(f) a second imaging optical element disposed to receive the second dispersed light, forming at least one image from said second dispersed light;

(g) a beam splitter that is disposed in one of the first collection path and the second collection path, so that a portion of the light traveling from the object along said one of the first collection path and the second collection path is diverted along a third collection path;

(h) an optical grating disposed in the third collection path, the optical grating modulating the light traveling along the third collection path, to produce modulated light having a modulation frequency corresponding to the velocity of the relative movement between the object and the optical analysis system;

(i) a light sensitive detector disposed in the third collection path to receive the modulated light, the light sensitive detector producing an electrical signal in response to the modulated light;

(j) means coupled to the light sensitive detector to receive the electrical signal, for determining the indication of the velocity of the relative movement between the object and the optical analysis system, producing a timing signal corresponding thereto;

(k) a first time delay integration (TDI) detector coupled to the means for determining the indication of the velocity to receive the timing signal and disposed to receive said at least one image formed by the first imaging optical element, said first TDI detector producing a first output signal that is indicative of at least one characteristic of the object by integrating said at least one image formed from the first dispersed light over time using the timing signal for synchronization of the first TDI detector with the movement over the first TDI detector of said at least one image formed by the first imaging optical element; and (l) a second TDI detector disposed to receive said at least one image formed by the second imaging optical element, said second TDI detector being coupled to said means for determining the indication of the velocity to receive the timing signal and producing a second output signal that is indicative of at least one other characteristic of the moving object by integrating said at least one image formed from the second dispersed light over time using the timing signal for synchronization of the second TDI detector with the relative motion of said at least one image formed by the second imaging optical element.

59. A method for determining an indication of a velocity of an object in motion using light from the object, comprising the steps of:

(a) modulating light from the object using an optical grating to produce modulated light having a modulation frequency that varies as a function of the velocity of the object;

(b) producing an electrical signal corresponding to an intensity of the modulated light;

(c) processing the electrical signal in the time domain to determine the indication of the velocity of the object.

60. The method of claim 59, further comprising the step of amplifying the electrical signal before the step of processing.

61. The method of claim 59, further comprising the step of filtering the electrical signal before the step of processing.

62. The method of claim 61, wherein the step of filtering the electrical signal comprises the step of:

(a) removing a direct current bias from the electrical signal; and (b) eliminating frequencies above a predetermined Nyquist limit from the electrical signal.

63. The method of claim 59, wherein the step of modulating light from the object using an optical grating comprises the step of utilizing an optical grating having a substantially uniform pattern.

64. The method of claim 63, further comprising the steps of:

(a) amplifying the electrical signal before the step of processing, producing an amplified signal;

(b) converting the amplified signal into a complex analog baseband signal;

(c) converting the complex analog baseband signal into a first digital sample sequence representing a real part of the amplified signal; and (d) converting the complex analog baseband signal into a second digital sample sequence representing an imaginary part of the amplified signal.

65. The method of claim 63, further comprising the steps of:

(a) amplifying the electrical signal before the step of processing, producing an amplified signal;

(b) filtering the amplified signal, producing a passband signal;

(c) converting the passband signal into a complex analog baseband signal;

(d) converting the complex analog baseband signal into a first digital sample sequence representing a real part of the passband signal; and (e) converting the complex analog baseband signal into a second digital sample sequence representing an imaginary part of the passband signal.

66. The method of claim 63, wherein the step of processing comprises the steps of:

(a) producing a baseband complex representation of the electrical signal;

(b) phase sampling the baseband complex representation of the electrical signal to determine a time series of phase samples of the baseband complex representation; and (c) determining a first derivative of the time series of the phase samples to determine the indication of the velocity of the object.

67. The method of claim 63, wherein the step of processing comprises the steps of:

(a) sampling the electrical signal, producing a sequence of digital samples;

(b) splitting the sequence of digital samples into a plurality of baseband signal pairs;

(c) separating the plurality of baseband signal pairs into sample packets, according to predefined criteria;

(d) applying an unwrapping algorithm to each sample packet;

(e) rejecting sample packets having a width outside of predefined limits; and (f) determining the indication of the velocity of the object based upon a sample packet that is not rejected.

68. The method of claim 67, further comprising the step of applying a lowpass filter to each baseband signal pair before the step of separating the baseband signal pairs into sample packets.

69. The method of claim 67, further comprising the step of employing a sequence of upper and lower sideband samples derived from the sequence of complex baseband samples for automated control of the method.

70. The method of claim 63, further comprising the steps of:

(a) applying a Hilbert transform to the electrical signal before the digital samples; and (b) using the upper sideband and the lower sideband digital samples to:

(i) determine a frequency associated with a light sensitive detector; and (ii) setting a local oscillator frequency for a baseband demodulator used for determining the indication of the velocity of the object.

71. The method of claim 59, wherein the step of processing comprises the step of utilizing at least one of a digital oscilloscope, a programmed computing device, and an application specific integrated circuit to perform the processing.

72. The method of claim 59, further comprising the steps of:

(a) providing a control system; and (b) using the control system to perform at least one of the following functions:

(i) regulating an amplification gain applied to the electrical signal in response to a varying level of the electrical signal;

(ii) determining a signal-to-noise ratio of the electrical signal for use in regulating a threshold applied to frequency measurements; and (iii) regulating a frequency of a baseband converter local oscillator used in the step of processing, as a function of the velocity of the object.

73. The method of claim 59, wherein the step of modulating light from the object using an optical grating comprises the step of utilizing an optical grating having a substantially non uniform pattern.

74. The method of claim 73, wherein the step of utilizing an optical grating comprises the step of utilizing an optical grating having at least one of:

(a) a plurality of alternating opaque bars and transparent gaps, widths of which vary in a linear progression in a direction perpendicular to a longitudinal extent of the bars and the transparent gaps; and (b) a plurality of alternating opaque bars and transparent gaps, the width of which vary in a non-linear pattern in a direction perpendicular to a longitudinal extent of the bars and the transparent gaps.

75. The method of claim 73, wherein the step of utilizing an optical grating comprises the step of utilizing an optical grating having two substantially identical sections, each with a substantially non-uniform pattern of bar and gap widths, disposed along an axis of motion of the object such that light from the object sequentially traverses said sections.

76. The method of claim 59, wherein the step of modulating light from the object using an optical grating comprises the steps of utilizing a first optical grating to modulate a first light beam from the object, producing first modulated light; and utilizing a second optical grating to modulate a second light beam from the object, producing second modulated light, wherein the first and second optical gratings have a substantially non uniform pattern.

77. The method of claim 76, wherein the step of modulating light from the object using an optical grating further comprises the step of aligning the first and second optical gratings such that image fields of the first and second optical gratings are disposed in series along an axis of motion of the object.

78. The method of claim 76, wherein the step of producing an electrical signal corresponding to an intensity of the modulated light comprises the steps of producing a first electrical signal corresponding to the first modulated light, and producing a second electrical signal corresponding to the second modulated light, further comprising the steps of converting the first electrical signal into a first sequence of digital samples, and converting the second electrical signal into a second sequence of digital samples.

79. The method of claim 78, further comprising the step of amplifying the first electrical signal and the second electrical signal before converting the first electrical signal and the second electrical signal into the first and second sequences of digital samples.

80. The method of claim 78, further comprising the step of filtering the first electrical signal and the second electrical signal before converting the first electrical signal and second electrical signal into the first sequence and second sequence of digital samples, respectively.

81. The method of claim 76, wherein the step of processing comprises the steps of:

(a) convolving the first electrical signal with the second electrical signal to produce a convolution;

(b) generating a cross-correlogram based on the convolution; and (c) determining the indication of the velocity from a peak amplitude of the cross-correlogram.

82. The method of claim 76, further comprising the steps of:

(a) providing a control system; and (b) using the control system to regulate an upper and a lower limit of a time shift in a cross-correlation function in response to a variation in the velocity of the object.

83. A method for determining an indication of a relative velocity associated with an object and one or more other characteristics of an object, comprising the steps of:

(a) directing light from the object along a first collection path;

(b) diverting a portion of the light traveling along the first collection path to a second collection path that is in a different direction than the first collection path;

(c) modulating light traveling along the second collection path as a function of the relative velocity;

(d) producing an electrical signal as a function of an intensity of the modulated light;

(e) processing the electrical signal in the time domain to determine the indication of the relative velocity associated with the object;

(f) providing a time delay integration (TDI) detector disposed to receive the light that is traveling along the first collection path;

(g) using the indication of the relative velocity associated with the object to synchronize the TDI detector with a motion of an image of the object on the TDI detector; and (h) analyzing an output signal from the TDI detector to determine at least one other characteristic of the object.

84. The method of claim 83, wherein the step of modulating the light comprises the step of providing an optical grating having a substantially uniform pitch; and wherein the step of processing the electrical signal to determine the indication of the relative velocity comprises the steps of:

(a) producing a baseband complex representation of the electrical signal;

(b) producing a time series of phase samples from the baseband complex representation; and (c) determining the indication of the relative velocity from a first derivative of the time series of phase samples.

85. The method of claim 83, wherein the step of modulating the light comprises the step of providing an optical grating that modulates the light, further comprising the steps of:

(a) diverting a portion of the light traveling along the second collection path to a third collection path that is in a different direction than the first and second collection paths, (b) providing a second optical grating having a substantially non uniform pitch, the second optical grating being disposed along the third collection path such that the optical grating and the second optical grating are aligned in series along an axis of relative motion associated with the object, the second optical grating modulating light traveling along the third collection path; and (c) producing a second electrical signal as a function of an intensity of the modulated light traveling along the third collection path, wherein the step of processing the electrical signal to determine the indication of the relative velocity associated with the object comprises the steps of:

(i) convolving the electrical signal with the second electrical signal to form a convolution;

(ii) producing a cross-correlogram based on the convolution; and (iii) determining the indication of the relative velocity from a peak amplitude of the cross-correlogram.

86. A method for determining an indication of a velocity and one or more other characteristics associated with a moving object, while there is relative movement between the object and an optical system used to determine the indication of the velocity and the one or more other characteristics, comprising the steps of:

(a) directing light from the object along a first collection path and a second collection path, the first and second collection paths being in a different direction than a direction of the relative movement between the object and the optical system;

(b) modulating light traveling along the first collection path;

(c) producing an electrical signal as a function of an intensity of the modulated light;

(d) processing the electrical signal in the time domain to determine the indication of the relative velocity between the optical system and the object;

(e) dispersing the light that is traveling along the second collection path, producing dispersed light;

(f) providing a time delay integration (TDI) detector disposed to receive the dispersed light;

(g) using the indication of the relative velocity to synchronize the TDI detector with movement of the dispersed light from the object over the TDI detector; and (h) analyzing an output signal from the TDI detector to determine said one or more other characteristics of the object.

87. The method of claim 86, wherein the step of modulating comprises the step of providing an optical grating having a substantially uniform pitch, and wherein the step of processing the electrical signal to determine the indication of the velocity between the optical system and the object comprises the steps of:

(a) creating a baseband complex representation of the electrical signal;

(b) producing a time series of phase samples from the baseband complex representation of the electrical signal; and (c) determining a first derivative of the time series of phase samples to determine the indication of the velocity between the optical system and the object.

88. The method of claim 86, further comprising the steps of:

(a) diverting a portion of the light traveling along the first collection path to a third collection path that is in a different direction than the first and second collection paths, (b) modulating light traveling along the third collection path, producing modulated light;

(c) producing a second electrical signal as a function of an intensity of the modulated light traveling along the third collection path;

(d) convolving the electrical signal and the second electrical signal to produce a cross-correlogram; and (e) determining the indication of the velocity between the optical system and the object from a peak amplitude of the cross-correlogram.

* * * * *

UNITED STATES PATENT AND TRADEMARK OFFICE
CERTIFICATE OF CORRECTION

PATENT NO. : 6,507,391 B2  
DATED : January 14, 2003  
INVENTOR(S) : Chen et al.

Page 1 of 1

It is certified that error appears in the above-identified patent and that said Letters Patent is hereby corrected as shown below:

Column 1,  
Line 6, after "Ser. No. 60/228,076," delete "1"

Column 20,  
Line 56, "(9.842 Ip/mm)" should read -- (9.842 1p/mm) --

Column 31,  
Line 13, "$P_{ush}$" should read -- $P_{usb}$ --  
Line 17, "$P_{isb}$" should read -- $P_{lsb}$ --

Column 34,  
Line 57, after "signals" insert -- from photodetectors 50 and 50a are applied to variable gain amplifiers 52 and 52a --

Column 38,  
Line 63, "produces" should read -- producing --

Column 41,  
Line 37, after "Claim 3" delete "wherein the other" and insert -- further comprising another --

Column 45,  
Line 53, "(IDI)" should read -- (TDI) --

Column 49,  
Line 17, after "the" insert -- step of processing, to generate a sequence of upper sideband and lower sideband --

Signed and Sealed this

Fifth Day of August, 2003

JAMES E. ROGAN  
*Director of the United States Patent and Trademark Office*

UNITED STATES PATENT AND TRADEMARK OFFICE
CERTIFICATE OF CORRECTION

PATENT NO. : 6,507,391 B2  
DATED : January 14, 2003  
INVENTOR(S) : James K. Riley et al.

It is certified that error appears in the above-identified patent and that said Letters Patent is hereby corrected as shown below:

Column 1,  
Line 6, after "Ser. No. 60/228,076," delete "1"

Column 20,  
Line 56, "(9.842 Ip/mm)" should read -- (9.842 1p/mm) --

Column 31,  
Line 13, "$P_{ush}$" should read -- $P_{usb}$ --  
Line 17, "$P_{isb}$" should read -- $P_{lsb}$ --

Column 34,  
Line 57, after "signals" insert -- from photodetectors 50 and 50a are applied to variable gain amplifiers 52 and 52a --

Column 38,  
Line 63, "produces" should read -- producing --

Column 41,  
Line 37, after "Claim 3" delete "wherein the other" and insert -- further comprising another --

Column 45,  
Line 53, "(IDI)" should read -- (TDI) --

Column 49,  
Line 17, after "the" insert -- step of processing, to generate a sequence of upper sideband and lower sideband --

This certificate supersedes Certificate of Correction issued August 5, 2003.

Signed and Sealed this

Second Day of December, 2003

JAMES E. ROGAN  
*Director of the United States Patent and Trademark Office*

UNITED STATES PATENT AND TRADEMARK OFFICE
CERTIFICATE OF CORRECTION

PATENT NO. : 6,507,391 B2
DATED : January 14, 2003
INVENTOR(S) : Riley et al.

It is certified that error appears in the above-identified patent and that said Letters Patent is hereby corrected as shown below:

Column 8,
Line 42, delete "are disposed, to pass" and insert -- (and the support) passing --

Column 15,
Line 27, after "object" insert -- omni-directionally at a longer wavelength $\lambda_2$. Some of these emitted photons are --

Signed and Sealed this

Eleventh Day of May, 2004

JON W. DUDAS
*Acting Director of the United States Patent and Trademark Office*